United States Patent
Wang et al.

(10) Patent No.: US 12,310,793 B2
(45) Date of Patent: May 27, 2025

(54) SYSTEM AND METHOD FOR PHOTOACOUSTIC IMAGING AND ULTRASOUND IMAGING

(71) Applicant: City University of Hong Kong, Kowloon (HK)

(72) Inventors: Lidai Wang, Kowloon (HK); Yachao Zhang, Kowloon (HK)

(73) Assignee: City University of Hong Kong, Kowloon (HK)

( * ) Notice: Subject to any disclaimer, the term of this patent is extended or adjusted under 35 U.S.C. 154(b) by 308 days.

(21) Appl. No.: 17/879,264

(22) Filed: Aug. 2, 2022

(65) Prior Publication Data
US 2024/0041436 A1 Feb. 8, 2024

(51) Int. Cl.
*A61B 8/00* (2006.01)
*A61B 5/00* (2006.01)

(52) U.S. Cl.
CPC .......... *A61B 8/5215* (2013.01); *A61B 5/0095* (2013.01); *A61B 8/4416* (2013.01); *A61B 8/463* (2013.01)

(58) Field of Classification Search
CPC ... A61B 8/5215; A61B 5/0095; A61B 8/4416; A61B 8/463; A61B 5/0035; A61B 5/7425; A61B 8/13; A61B 8/5223; A61B 8/5261; A61B 8/5269; A61B 8/54; A61B 8/5207
See application file for complete search history.

(56) References Cited

U.S. PATENT DOCUMENTS

| | | | |
|---|---|---|---|
| 2004/0122323 A1* | 6/2004 | Vortman | A61N 7/02 600/459 |
| 2018/0020920 A1* | 1/2018 | Ermilov | A61B 5/14546 600/317 |
| 2019/0183349 A1* | 6/2019 | Miyasato | A61B 8/403 |

OTHER PUBLICATIONS

S. Mandal, E. Nasonova, X. L. Dean-Ben, and D. Razansky, "Optimal self-calibration of tomographic reconstruction parameters in whole-body small animal optoacoustic imaging," Photoacoustics, vol. 2, No. 3, pp. 128-136, Sep. 2014.
S. Siregar, R. Nagaoka, I. Ul Haq, and Y. Saijo, "Non local means denoising in photoacoustic imaging," Jpn. J. Appl. Phys., vol. 57, No. 7, p. 07LB06, Jul. 2018.
S. Agrawal, T. Suresh, A. Garikipati, A. Dangi, and S. R. Kothapalli, "Modeling combined ultrasound and photoacoustic maging: Simulations aiding device development and artificial intelligence," Photoacoustics, vol. 24, p. 100304, Dec. 2021.
Y. Lou, W. Zhou, T. P. Matthews, C. M. Appleton, and M. A. Anastasio, "Generation of anatomically realistic numerical phantoms for photoacoustic and ultrasonic breast imaging," J. Biomed. Opt., vol. 22, No. 4, p. 041015, Jan. 2017.

(Continued)

*Primary Examiner* — Bo Joseph Peng
(74) *Attorney, Agent, or Firm* — Renner, Kenner, Greive, Bobak, Taylor & Weber

(57) ABSTRACT

A system for processing photoacoustic and ultrasound imaging data includes processor(s) and memory storing program(s) configured to be executed by the processor(s). The program(s) include instructions for: obtaining ultrasound imaging data representative of an ultrasound image of the object, performing a speed of sound value optimization operation based on the ultrasound imaging data for facilitating image reconstruction, and performing an image reconstruction operation. The ultrasound imaging data is obtained from a system for photoacoustic imaging and ultrasound imaging.

13 Claims, 26 Drawing Sheets

(56) References Cited

OTHER PUBLICATIONS

M. Xu and L. V. Wang, "Analytic explanation of spatial resolution related to bandwidth and detector aperture size in thermoacoustic or photoacoustic reconstruction," Phys. Rev. E, vol. 67, No. 5, p. 056605, May 2003.

P. Wray, L. Lin, P. Hu, and L. V. Wang, "Photoacoustic computed tomography of human extremities," J. Biomed. Opt., vol. 24, No. 2, p. 1, Feb. 2019.

P. J. van den Berg, K. Daoudi, H. J. Bernelot Moens, and W. Steenbergen, "Feasibility of photoacoustic/ultrasound imaging of synovitis in finger joints using a point-of-care system," Photoacoustics, vol. 8, pp. 8-14, Dec. 2017.

J. Aguirre, M. Schwarz, D. Soliman, A. Buehler, M. Omar, and V. Ntziachristos, "Broadband mesoscopic optoacoustic tomography reveals skin layers," Opt. Lett. Vol. 39, Issue 21, pp. 6297-6300, vol. 39, No. 21, pp. 6297-6300, Nov. 2014.

Theramedical, "Introducing: msot invision 512-echo."

R. Rau, D. Schweizer, V. Vishnevskiy, and O. Goksel, "Ultrasound Aberration Correction based on Local Speed-of-Sound Map Estimation," IEEE Int. Ultrason. Symp. IUS Oct. 2019, 2003-2006 (2019).

C. Liu and L. Wang, "Functional photoacoustic microscopy of hemodynamics: a review," Biomed. Eng. Lett. 12(2), 97-124 (2022).

Yachao Zhang, Lidai Wang, Adaptive dual-speed ultrasound and photoacoustic computed tomography, Photoacoustics, vol. 27, 2022, 100380, ISSN 2213-5979, https://doi.org/10.1016/j.pacs.2022.100380.

Y. Zhang and L. Wang, "Video-rate full-ring ultrasound and photoacoustic computed tomography with real-time sound speed optimization," Biomed. Opt. Express 13, 4398-4413 (2022).

S. Na, J.J. Russin, L. Lin, X. Yuan, P. Hu, K.B. Jann, K. Yan, K. Maslov, J. Shi, D.J. Wang, C.Y. Liu, L. V. Wang, Massively parallel functional photoacoustic computed tomography of the human brain, Nat. Biomed. Eng. 2021. (2021) 1-9. https://doi.org/10.1038/s41551-021-00735-8.

L. Lin, P. Hu, X. Tong, S. Na, R. Cao, X. Yuan, D.C. Garrett, J. Shi, K. Maslov, L. V. Wang, High-speed three-dimensional photoacoustic computed tomography for preclinical research and clinical translation, Nat. Commun. 2021 121. 12 (2021) 1-10. https://doi.org/10.1038/s41467-021-21232-1.

L. Li, L. Zhu, C. Ma, L. Lin, J. Yao, L. Wang, K. Maslov, R. Zhang, W. Chen, J. Shi, L. V. Wang, Single-impulse panoramic photoacoustic computed tomography of small-animal whole-body dynamics at high spatiotemporal resolution, Nat. Biomed. Eng. 2017 15. 1 (2017) 1-11. https://doi.org/10.1038/s41551-017-0071.

A. Ron, S. Kumar Kalva, V. Periyasamy, X. Luis Deán-Ben, D. Razansky, A. Ron, V. Periyasamy, D. Razansky, S.K. Kalva, X.L. Deán-Ben, Flash Scanning Volumetric Optoacoustic Tomography for High Resolution Whole-Body Tracking of Nanoagent Kinetics and Biodistribution, Laser Photon. Rev. 15 (2021) 2000484. https://doi.org/10.1002/LPOR.202000484.

R. Ni, A. Villois, X.L. Dean-Ben, Z. Chen, M. Vaas, S. Stavrakis, G. Shi, A. deMello, C. Ran, D. Razansky, P. Arosio, J. Klohs, In-vitro and in-vivo characterization of CRANAD-2 for multi-spectral optoacoustic tomography and fluorescence imaging of amyloid-beta deposits in Alzheimer mice, Photoacoustics. 23 (2021) 100285. https://doi.org/10.1016/J.PACS.2021.100285.

J. Kukačka, S. Metz, C. Dehner, A. Muckenhuber, K. Paul-Yuan, A. Karlas, E.M. Fallenberg, E. Rummeny, D. Justel, V. Ntziachristos, Image processing improvements afford second-generation handheld optoacoustic imaging of breast cancer patients, Photoacoustics. 26 (2022) 100343. https://doi.org/10.1016/J.PACS.2022.100343.

Y. Zhang, Y. Wang, P. Lai, L. Wang, Video-rate dual-modal wide-beam harmonic ultrasound and photoacoustic computed tomography, IEEE Trans. Med. Imaging. 41 (2022) 727-736. https://doi.org/10.1109/TMI.2021.3122240.

B. Lafci, E. Merčep, J.L. Herraiz, X.L. Deán-Ben, D. Razansky, Noninvasive multiparametric characterization of mammary tumors with transmission-reflection optoacoustic ultrasound, Neoplasia. 22 (2020) 770-777. https://doi.org/10.1016/J.NEO.2020.10.008.

Y. Zhang, L. Wang, Video-Rate Ring-Array Ultrasound and Photoacoustic Tomography, IEEE Trans. Med. Imaging. 39 (2020) 4369-4375. https://doi.org/10.1109/TMI.2020.3017815.

S. Qi, Y. Zhang, G. Liu, J. Chen, X. Li, Q. Zhu, Y. Yang, F. Wang, J. Shi, C.S. Lee, G. Zhu, P. Lai, L. Wang, C. Fang, Plasmonic-doped melanin-mimic for CXCR4-targeted NIR-II photoacoustic computed tomography-guided photothermal ablation of orthotopic hepatocellular carcinoma, Acta Biomater. 129 (2021) 245-257. https://doi.org/10.1016/J.ACTBIO.2021.05.034.

S. Li, Q. Deng, Y. Zhang, X. Li, G. Wen, X. Cui, Y. Wan, Y. Huang, J. Chen, Z. Liu, L. Wang, C.-S. Lee, S. Li, X. Li, X. Cui, Y. Wan, J. Chen, C. Lee, Q. Deng, Y. Huang, Z. Liu, Y. Zhang, G. Wen, L. Wang, Rational Design of Conjugated Small Molecules for Superior Photothermal Theranostics in the NIR-II Biowindow, Adv. Mater. 32 (2020) 2001146. https://doi.org/10.1002/ADMA.202001146.

L. He, Y. Zhang, J. Chen, G. Liu, J. Zhu, X. Li, D. Li, Y. Yang, C.S. Lee, J. Shi, C. Yin, P. Lai, L. Wang, C. Fang, A multifunctional targeted nanoprobe with high NIR-II PAI/MRI performance for precise theranostics of orthotopic early-stage hepatocellular carcinoma, J. Mater. Chem. B. 9 (2021) 8779-8792. https://doi.org/10.1039/D1TB01729B.

M. Zha, X. Lin, U.S. Ni, Y. Li, Y. Zhang, X. Zhang, L. Wang, K. Li, An Ester-Substituted Semiconducting Polymer with Efficient Nonradiative Decay Enhances NIR-II Photoacoustic Performance for Monitoring of Tumor Growth, Angew. Chemie Int. Ed. 59 (2020) 23268-23276. https://doi.org/10.1002/ANIE.202010228.

J. Zhang, Y. Zhang, Q. Guo, G. Wen, H. Xiao, S. Qi, Y. Wang, H. Zhang, L. Wang, H. Sun, Photoacoustic/Fluorescence Dual-Modality Probe for Biothiol Discrimination and Tumor Diagnosis in Cells and Mice, ACS Sensors. 7 (2022) 1105-1112. https://doi.org/10.1021/ACSSENSORS.2C00058.

M.A. Lediju Bell, Photoacoustic imaging for surgical guidance: Principles, applications, and outlook, J. Appl. Phys. 128 (2020) 060904. https://doi.org/10.1063/5.0018190.

T. Wei, J. Liu, D. Li, S. Chen, Y. Zhang, J. Li, L. Fan, Z. Guan, C.-M. Lo, L. Wang, K. Man, D. Sun, T. Wei, D. Li, S. Chen, Y. Zhang, J. Li, L. Fan, Z. Guan, L. Wang, D. Sun, J. Liu, C. Lo, K. Man, Development of Magnet-Driven and Image-Guided Degradable Microrobots for the Precise Delivery of Engineered Stem Cells for Cancer Therapy, Small. 16 (2020) 1906908. https://doi.org/10.1002/SMLL.201906908.

D. Li, Y. Zhang, C. Liu, J. Chen, D. Sun, L. Wang, Review of photoacoustic imaging for microrobots tracking in vivo [Invited], Chinese Opt. Lett. 19 (2021) 111701. https://doi.org/10.3788/COL202119.111701.

E. Merčep, N.C. Burton, J. Claussen, D. Razansky, Whole-body live mouse imaging by hybrid reflection-mode ultrasound and optoacoustic tomography, Opt. Lett. 40 (2015) 4643. https://doi.org/10.1364/OL.40.004643.

E. Merčep, J.L. Herraiz, X.L. Dean-Ben, D. Razansky, Transmission-reflection optoacoustic ultrasound (TROPUS) computed tomography of small animals, Light Sci. Appl. 2019 81. 8 (2019) 1-12. https://doi.org/10.1038/s41377-019-0130-5.

M. Cui, H. Zuo, X. Wang, K. Deng, J. Luo, C. Ma, Adaptive photoacoustic computed tomography, Photoacoustics. 21 (2021) 100223. https://doi.org/10.1016/J.PACS.2020.100223.

S. Park, F.J. Brooks, U. Villa, R. Su, M.A. Anastasio, A.A. Oraevsky, Normalization of optical fluence distribution for three-dimensional functional optoacoustic tomography of the breast, Https://Doi.Org/10.1117/1.JBO.27.3.036001. 27 (2022) 036001. https://doi.org/10.1117/1.JBO.27.3.036001.

B.E. Treeby, T.K. Varslot, E.Z. Zhang, J.G. Laufer, P.C. Beard, Automatic sound speed selection in photoacoustic mage reconstruction using an autofocus approach, Https://Doi.Org/10.1117/1.3619139. 16 (2011) 090501. https://doi.org/10.1117/1.3619139.

J. Xia, C. Huang, K. Maslov, M.A. Anastasio, L. V. Wang, Enhancement of photoacoustic tomography by ultrasonic computed tomography based on optical excitation of elements of a full-ring transducer array, Opt. Lett. 38 (2013) 3140. https://doi.org/10.1364/OL.38.003140.

(56) References Cited

OTHER PUBLICATIONS

G. Wen, X. Li, Y. Zhang, X. Han, X. Xu, C. Liu, K.W.Y. Chan, C.S. Lee, C. Yin, L. Bian, L. Wang, Effective Phototheranostics of Brain Tumor Assisted by Near-Infrared-II Light-Responsive Semiconducting Polymer Nanoparticles, ACS Appl. Mater. Interfaces. 12 (2020) 33492-33499. https://doi.org/10.1021/ACSAMI.0C08562/SUPPL_FILE/AMOC08562_SI_001.PDF.

C. Li, L. Huang, N. Duric, H. Zhang, C. Rowe, An improved automatic time-of-flight picker for medical ultrasound tomography, Ultrasonics. 49 (2009) 61-72. https://doi.org/10.1016/J.ULTRAS.2008.05.005.

W. Marczak, Water as a standard in the measurements of speed of sound in liquids, J. Acoust. Soc. Am. 102 (1998) 2776. https://doi.org/10.1121/1.420332.

S. Jeon, W. Choi, B. Park, C. Kim, A Deep Learning-Based Model That Reduces Speed of Sound Aberrations for Improved in Vivo Photoacoustic Imaging, IEEE Trans. Image Process. 30 (2021) 8773-8784. https://doi.org/10.1109/TIP.2021.3120053.

M.S. Hassouna, A.A. Farag, Multi-stencils fast marching methods: a highly accurate solution to the eikonal equation on cartesian domains, IEEE Trans. Pattern Anal. Mach. Intell. 29 (2007) 1563-1574. https://doi.org/10.1109/TPAMI.2007.1154.

C. Cai, X. Wang, K. Deng, J. Luo, C. Ma, Photoacoustic computed tomography for joint reconstruction of initial pressure and sound speed in vivo using a feature coupling method, (2019) 12. https://doi.org/10.1117/12.2531541.

B.E. Treeby, B.T. Cox, k-Wave: MATLAB toolbox for the simulation and reconstruction of photoacoustic wave fields, Https://Doi.Org/10.1117/1.3360308. 15 (2010) 021314. https://doi.org/10.1117/1.3360308.

K. Basak, X. Luis Dean-Ben, S. Gottschalk, M. Reiss, D. Razansky, Non-invasive determination of murine placental and foetal functional parameters with multispectral optoacoustic tomography, Light Sci. Appl. 2019 81. 8 (2019) 1-10. https://doi.org/10.1038/s41377-019-0181-7.

G. S. Jeng et al., "Real-time interleaved spectroscopic photoacoustic and ultrasound (PAUS) scanning with simultaneous fluence compensation and motion correction," Nat. Commun. 2021 121, vol. 12, No. 1, pp. 1-12, Jan. 2021.

J. Robin et al., "Hemodynamic response to sensory stimulation in mice: Comparison between functional ultrasound and optoacoustic imaging," Neuroimage, vol. 237, p. 118111, Aug. 2021.

S. Park, J. Jang, J. Kim, Y. S. Kim, and C. Kim, "Real-time Triple-modal Photoacoustic, Ultrasound, and Magnetic Resonance Fusion Imaging of Humans," IEEE Trans. Med. Imaging, vol. 36, No. 9, pp. 1912-1921, Sep. 2017.

A. Wiacek, K. C. Wang, H. Wu, and M. A. L. Bell, "Photoacoustic-Guided Laparoscopic and Open Hysterectomy Procedures Demonstrated with Human Cadavers," IEEE Trans. Med. Imaging, vol. 40, No. 12, pp. 3279-3292, Dec. 2021.

J. Robin, A. Ozbek, M. Reiss, X. L. Dean-Ben, and D. Razansky, "Dual-Mode Volumetric Photoacoustic and Contrast Enhanced Ultrasound Imaging with Spherical Matrix Arrays," IEEE Trans. Med. Imaging, 2021.

J. Chen et al., "Dual-foci fast-scanning photoacoustic microscopy with 3.2-MHz A-line rate," Photoacoustics, vol. 23, p. 100292, Sep. 2021.

L. Wang, K. Maslov, and L. V. Wang, "Single-cell label-free photoacoustic flowoxigraphy in vivo," Proc. Natl. Acad. Sci. U. S. A., vol. 110, No. 15, pp. 5759-5764, Apr. 2013.

C. Liu, J. Chen, Y. Zhang, J. Zhu, and L. Wang, "Five-wavelength optical-resolution photoacoustic microscopy of blood and lymphatic vessels," https://doi.org/10.1117/1.AP.3.1.016002, vol. 3, No. 1, p. 016002, Jan. 2021.

J. Zhu et al., "Self-Fluence-Compensated Functional Photoacoustic Microscopy," IEEE Trans. Med. Imaging, vol. 40, No. 12, pp. 3856-3866, Dec. 2021.

J. Chen et al., "Confocal visible/NIR photoacoustic microscopy of tumors with structural, functional, and nanoprobe contrasts," Photonics Res. vol. 8, Issue 12, pp. 1875-1880, vol. 8, No. 12, pp. 1875-1880, Dec. 2020.

A. Taruttis, S. Morscher, N. C. Burton, D. Razansky, and V. Ntziachristos, "Fast Multispectral Optoacoustic Tomography (MSOT) for Dynamic Imaging of Pharmacokinetics and Biodistribution in Multiple Organs," PLoS One, vol. 7, No. 1, p. e30491, Jan. 2012.

J. Zhang et al., "Controllable Cleavage of C—N Bond-Based Fluorescent and Photoacoustic Dual-Modal Probes for the Detection of H2S in Living Mice," ACS Appl. Bio Mater., vol. 4, No. 3, pp. 2020-2025, Mar. 2021.

L. Lin et al., "Single-breath-hold photoacoustic computed tomography of the breast," Nat. Commun. 2018 91, vol. 9, No. 1, pp. 1-9, Jun. 2018.

Li et al., "Small near-infrared photochromic protein for photoacoustic multi-contrast imaging and detection of protein Interactions in vivo," Nat. Commun. 2018 91, vol. 9, No. 1, pp. 1-14, Jul. 2018.

C. Yin et al., "Organic semiconducting polymer amphiphile for near-infrared-II light-triggered phototheranostics," Biomaterials, vol. 232, p. 119684, Feb. 2020.

J. Yao and L. V. Wang, "Photoacoustic brain imaging: from microscopic to macroscopic scales," Neurophotonics, vol. 1, No. 1, p. 011003, May 2014.

E. Merčep, G. Jeng, S. Morscher, p. C. Li, and D. Razansky, "Hybrid optoacoustic tomography and pulse-echo ultrasonography using concave arrays," IEEE Trans. Ultrason. Ferroelectr. Freq. Control, vol. 62, No. 9, pp. 1651-1661, Sep. 2015.

X. L. Deán-Ben and D. Razansky, "On the link between the speckle free nature of optoacoustics and visibility of structures in limited-view tomography," Photoacoustics, vol. 4, No. 4, pp. 133-140, Dec. 2016.

D. van de Sompel, L. S. Sasportas, A. Dragulescu-Andrasi, S. Bohndiek, and S. S. Gambhir, "Improving Image Quality by Accounting for Changes in Water Temperature during a Photoacoustic Tomography Scan," PLoS One, vol. 7, No. 10, p. e45337, Oct. 2012.

\* cited by examiner

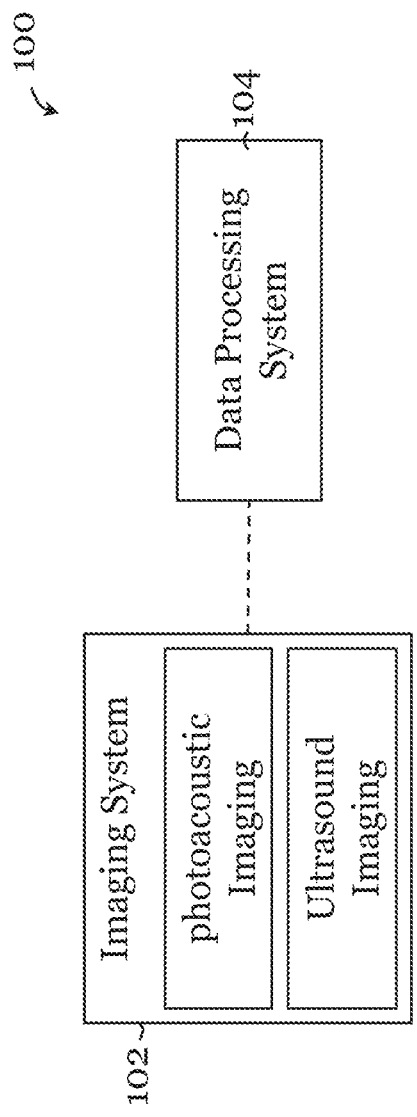
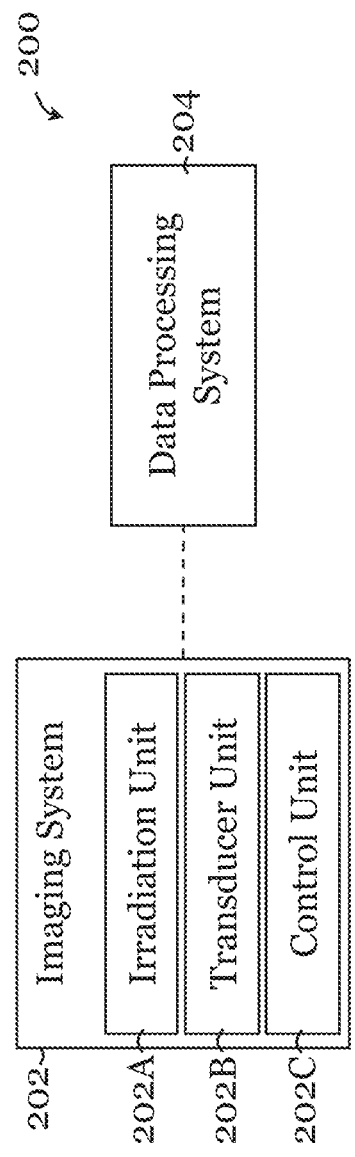

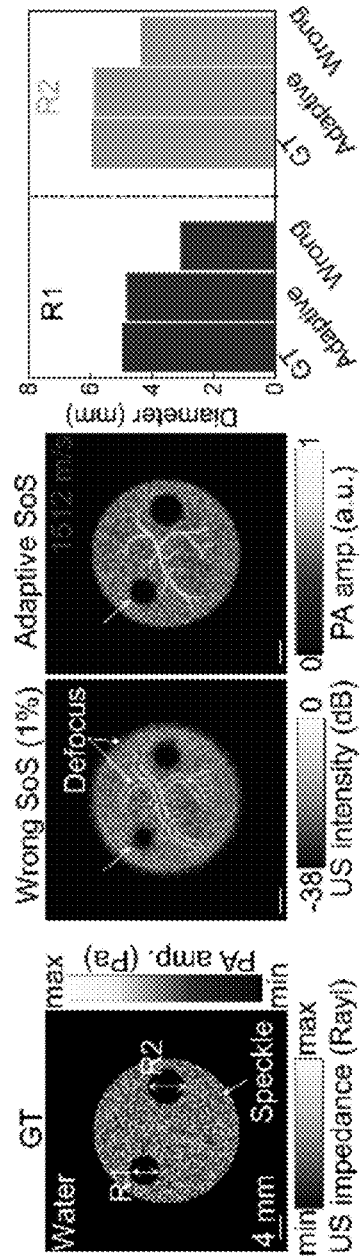
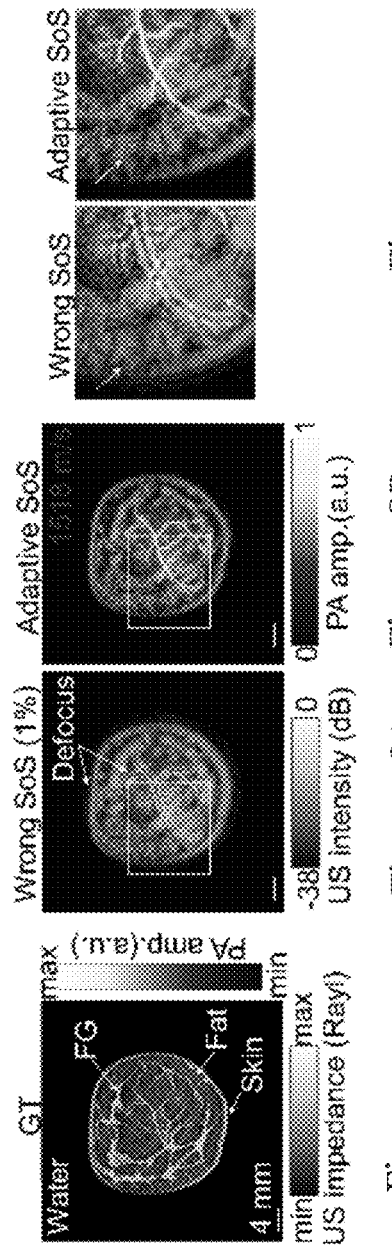
Figure 14
Figure 15A
Figure 15B
Figure 16
Figure 17
Figure 18A
Figure 18B
Figure 19

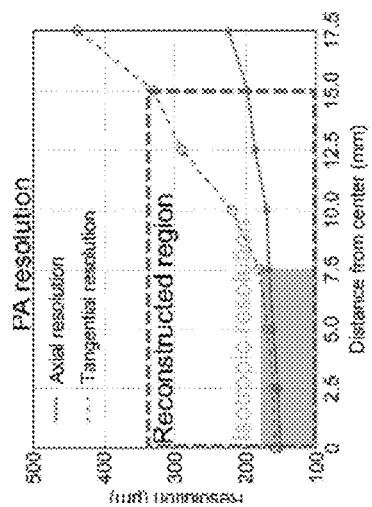
Figure 21B
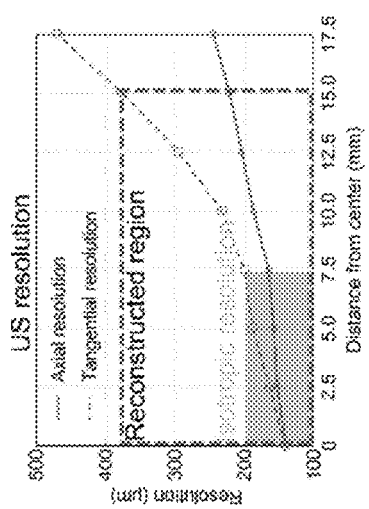
Figure 21A
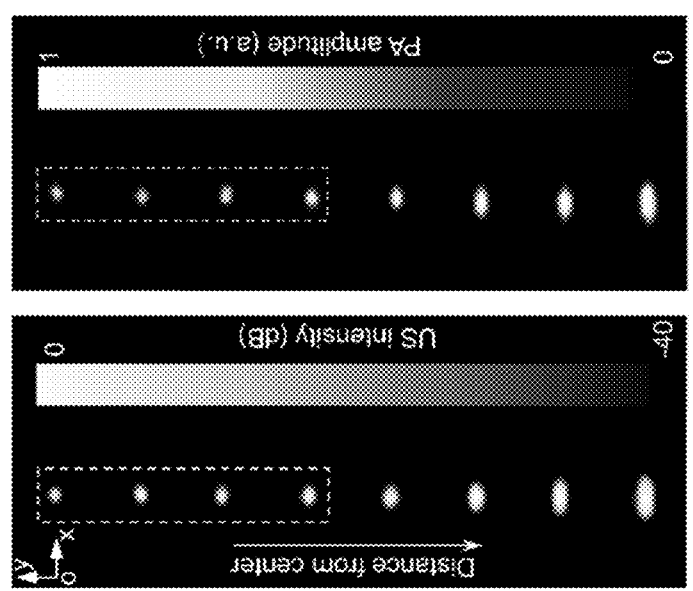
Figure 20B
Figure 20A

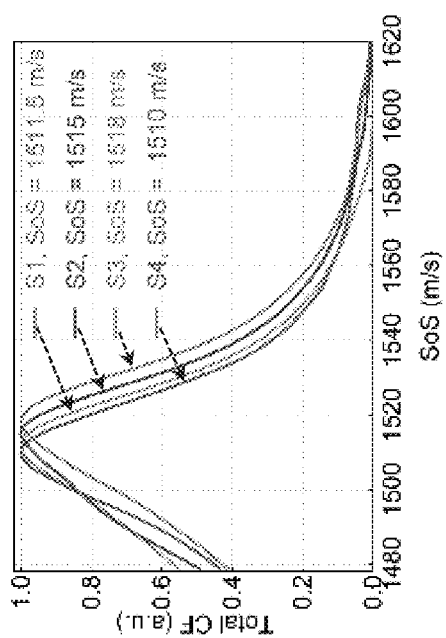
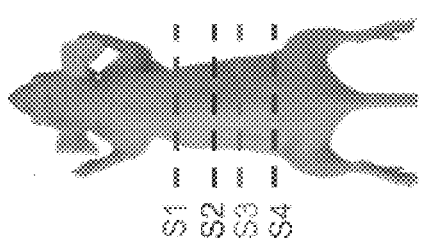
Figure 24A
Figure 24B

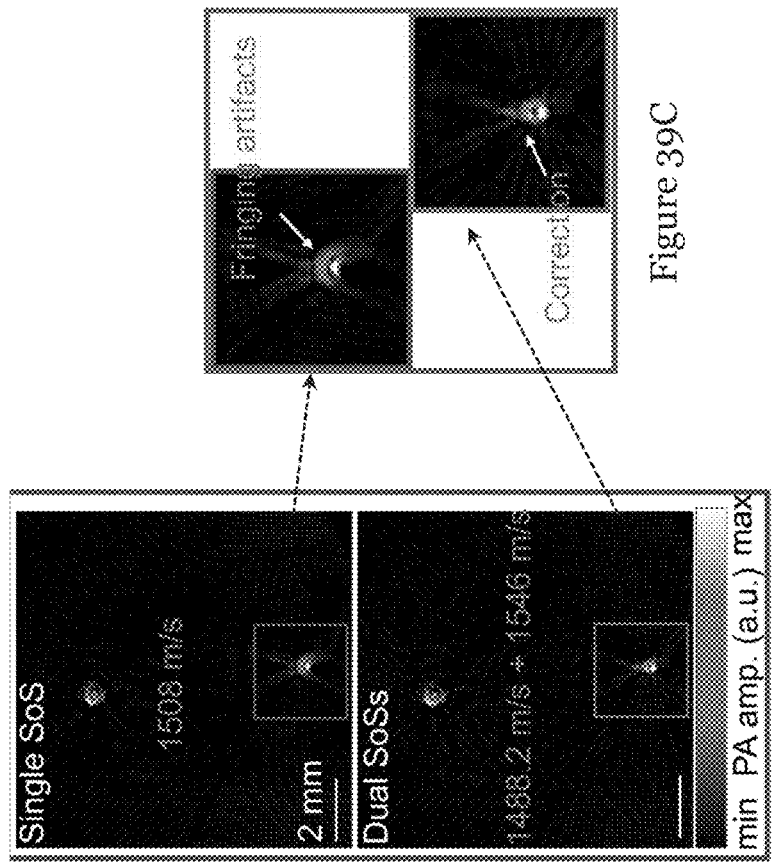
Figure 39C
Figure 39B
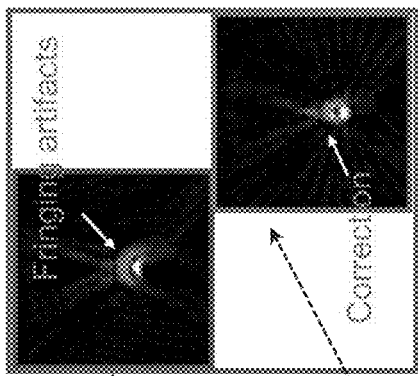
Figure 39A

SYSTEM AND METHOD FOR PHOTOACOUSTIC IMAGING AND ULTRASOUND IMAGING

TECHNICAL FIELD

The invention relates to photoacoustic imaging and ultrasound imaging, in particular hybrid photoacoustic imaging and ultrasound imaging, and related image processing.

BACKGROUND

Ultrasound imaging and photoacoustic imaging (e.g., photoacoustic computed tomography) are imaging modalities commonly used in clinical and preclinical applications. Ultrasound imaging basically involves transmitting ultrasound waves to an object and receiving in response ultrasound waves reflected, scattered, and/or transmitted by the object. The received ultrasound waves (echoes) are processed to generate ultrasound image. On the other hand, photoacoustic imaging operates based on the photoacoustic effect. It basically involves irradiating an object with electromagnetic radiation (e.g., light such as laser), the energy of which is at least partly absorbed by the object to cause a thermoelastic expansion of the object, and in turn, ultrasonic emission by the object. The ultrasonic emission are processed to generate photoacoustic image.

Imaging systems operable to perform both ultrasound imaging and photoacoustic imaging exist. These imaging systems can be used to image an object (e.g., a part of it on the imaging plane) to provide co-registered images with complementary contrasts.

Speed of sound, e.g., speed(s) of sound within the imaged sample, is an important reconstruction parameter for achieving optimal resolution and/or contrast in ultrasound and photoacoustic images. Inaccurate speed of sound value selection in the image reconstruction process may cause feature splitting, fringing artifacts, distortion, blurring, etc. on the images, which lowers quality of the images and potentially reduces usefulness of the images. Problematically, the speed of sound within the imaged sample depends on various factors such as sample size, temperature of the sample, physiological status, etc., and an accurate value of the speed of sound within the imaged sample is often unknown. Some existing techniques for speed of sound determination for image reconstruction require manual adjustment by the operator, which can be slow and subjective hence inaccurate. Some other existing techniques for speed of sound determination for image reconstruction involve complex algorithm and require resource-intensive iterative computation, which can be slow and inefficient.

SUMMARY OF THE INVENTION

In a first aspect of the invention, there is provided a system for processing photoacoustic and ultrasound imaging data. The system comprises one or more processors; and memory storing one or more programs configured to be executed by the one or more processors. The one or more programs comprise instructions for: obtaining ultrasound imaging data representative of an ultrasound image of an object, the ultrasound imaging data being obtained from a system for photoacoustic imaging and ultrasound imaging, e.g., as a result of an operation mode for ultrasound imaging; performing a speed of sound value optimization operation based on the ultrasound imaging data for facilitating image reconstruction; and performing an image reconstruction operation. The object may be an animal (e.g., rat, mouse, mice, rabbit, monkey, etc.), a human, an imaging phantom, a biological tissue, etc.

Optionally, the instructions for performing the speed of sound value optimization operation comprise instructions for processing the ultrasound imaging data to determine an optimal speed of sound value, the optimal speed of sound value is for use in the image reconstruction operation. In one example, this speed of sound value optimization operation corresponds to a first optimization operation.

Optionally, the instructions for processing the ultrasound imaging data to determine an optimal speed of sound value comprise instructions for processing only the ultrasound imaging data in a predetermined region of interest to determine an optimal speed of sound value.

Optionally, the instructions for processing the ultrasound imaging data to determine an optimal speed of sound value comprise instructions for: processing the ultrasound imaging data respectively using each of a plurality of predetermined speed of sound values to determine a plurality of total coherence factor values, each respective one of the plurality of total coherence factor values being associated with the processing of the ultrasound imaging data using a respective one of the predetermined speed of sound values; and determining, based on the plurality of total coherence factor values, a speed of sound value that corresponds to the optimal speed of sound value. Processing of the ultrasound imaging data respectively using each of a plurality of predetermined speed of sound values involves processing the same set of ultrasound imaging data multiple times, each time using a respective predetermined speed of sound value. The multiple times of processing may occur simultaneously or sequentially. The determining of the speed of sound value that corresponds to the optimal speed of sound value based on the plurality of total coherence factor values may include determining from the plurality of total coherence factor values the largest total coherence factor value, and determining the corresponding speed of sound value associated with the largest total coherence factor value as the optimal speed of sound value.

Optionally, the instructions for processing the ultrasound imaging data respectively using each of a plurality of predetermined speed of sound values comprise instructions for: processing the ultrasound imaging data respectively using each of a plurality of predetermined speed of sound values to determine a plurality of coherence factor maps, each respective one of the plurality of coherence factor maps is determined using a respective one of the predetermined speed of sound values; and for each respective one of the plurality of coherence factor maps, determining a respective total coherence factor value based on a sum of the coherence factor values of the coherence factor map. Processing of the ultrasound imaging data respectively using each of a plurality of predetermined speed of sound values involves processing the same set of ultrasound imaging data multiple times, each time using a respective predetermined speed of sound value. The multiple times of processing may occur simultaneously or sequentially.

Optionally, the instructions for determining a speed of sound value based on the plurality of total coherence factor values comprise instructions for: determining a total coherence factor value function based on the plurality of total coherence factor values; and determining a speed of sound value corresponding to an extreme (e.g., maximum) value of the total coherence factor value function, the determined speed of sound value corresponds to the optimal speed of sound value.

Optionally, the instructions for determining a total coherence factor value function comprise instructions for performing an interpolation operation using the plurality of total coherence factor values. The interpolation operation may include a spline interpolation operation, a linear interpolation operation, a polynomial interpolation operation, etc.

Optionally, for each respective one of the coherence factor map, the coherence factor value of each pixel $CF_{v_i}(n)$ can be determined based on $$CF_{v_i}(n) = \frac{\left|\sum_{Rcv=1}^{N_{elm}} \sum_{Tx=1}^{N_{elm}} I(n)\right|^2}{N_{elm} \times \sum_{Rcv=1}^{N_{elm}} \left|\sum_{Tx=1}^{N_{elm}} I(n)\right|^2}$$

where n represents position of the pixel, $v_i$ is the predetermined speed of sound value, Tx and Rcv are transducer elements of the system for photoacoustic imaging and ultrasound imaging that are operated as ultrasound waves transmitters and ultrasound waves receivers respectively, $N_{elm}$ is number of transducer elements in the system for photoacoustic imaging and ultrasound imaging, I(n) is a delayed channel data according to $v_i$ and a distance of flight representative of a distance between the pixel position and the transducer element operated as ultrasound waves receiver.

Optionally, the one or more programs further comprise instructions for: obtaining corresponding photoacoustic imaging data representative of a corresponding photoacoustic image of the object, the photoacoustic imaging data being obtained from the system for photoacoustic imaging and ultrasound imaging, e.g., as a result of an operation mode for photoacoustic imaging.

Optionally, the instructions for performing the image reconstruction operation comprise instructions for: processing the photoacoustic imaging data based on the determined optimal speed of sound value to reconstruct a photoacoustic image of the object. The processing may be automatically performed upon or after determining the optimal speed of sound value.

Optionally, the instructions for performing the image reconstruction operation comprise instructions for: processing the ultrasound imaging data based on the determined optimal speed of sound value to reconstruct an ultrasound image of the object. The processing may be automatically performed upon or after determining the optimal speed of sound value.

Optionally, the instructions for processing the photoacoustic imaging data based on the determined optimal speed of sound value comprise instructions for processing the photoacoustic imaging data using a delay-and-sum beamforming method based on the determined optimal speed of sound value to reconstruct the photoacoustic image of the object. The delay-and-sum beamforming method may be a weighted delay-and-sum beamforming method.

Optionally, the instructions for processing the ultrasound imaging data based on the determined optimal speed of sound value comprise instructions for processing the ultrasound imaging data using a delay-and-sum beamforming method based on the determined optimal speed of sound value to reconstruct the ultrasound image of the object. The delay-and-sum beamforming method may be a weighted delay-and-sum beamforming method.

Optionally, the instructions for processing the photoacoustic imaging data based on the determined optimal speed of sound value comprise instructions for processing only the photoacoustic imaging data in a predetermined region of interest.

Optionally, the one or more programs further comprise instructions for: processing the photoacoustic imaging data using a bandpass filter prior to processing the ultrasound imaging data based on the determined optimal speed of sound value. The bandpass filter may be arranged to provide a passband in about 0 MHz to about 10 MHz, or about 0 MHz to about 8.5 MHz. The bandpass filter may be a Butterworth filter, e.g., a $3^{rd}$ order Butterworth filter.

Optionally, the one or more programs further comprise instructions for: processing the reconstructed photoacoustic image, the processing comprises filtering the reconstructed photoacoustic image.

Optionally, the instructions for processing the ultrasound imaging data based on the determined optimal speed of sound value comprise instructions for processing only the ultrasound imaging data in a predetermined region of interest.

Optionally, the one or more programs further comprise instructions for: processing the ultrasound imaging data using a bandpass filter prior to processing the ultrasound imaging data based on the determined optimal speed of sound value. The bandpass filter may be arranged to provide a passband in about 0 MHz to about 10 MHz, or about 0 MHz to about 8.5 MHz. The bandpass filter may be a Butterworth filter, e.g., a $3^{rd}$ order Butterworth filter.

Optionally, the one or more programs further comprise instructions for: processing the reconstructed ultrasound image, the processing comprises filtering the reconstructed ultrasound image.

Optionally, the instructions for performing the speed of sound value optimization operation comprise instructions for: performing a segmentation operation on the ultrasound imaging data to obtain a plurality of subsets of ultrasound imaging data; and determining for each respective one of the plurality of subsets of ultrasound imaging data, a respective optimal speed of sound value for use in the image reconstruction operation. In one example, this speed of sound value optimization operation corresponds to a second optimization operation.

Optionally, the instructions for performing a segmentation operation on the ultrasound imaging data comprise instructions for: processing the ultrasound imaging data to determine a boundary between two sections of the ultrasound image, e.g., a boundary between the object and a coupling medium (a medium arranged between the object and the transducer elements during imaging); and dividing the ultrasound imaging data into, at least, a first subset of ultrasound imaging data associated with one of the two sections (e.g., the object) and a second subset of ultrasound imaging data associated with another one of the two sections (e.g., the coupling medium). Optionally, the boundary is an endless boundary. Optionally, the ultrasound imaging data may be divided into further subset(s) of the ultrasound imaging data. The coupling medium may be liquid, e.g., water, oil, etc.

Optionally, the instructions for processing the ultrasound imaging data to determine a boundary between two sections of the ultrasound image comprise instructions for: determining a map based on ultrasound signals received by each respective transducer element of the system for photoacoustic imaging and ultrasound imaging of as a result of ultrasound waves detected at the transducer element in response to transmission of ultrasound waves by the transducer element towards the object; and determining the boundary based on the map.

Optionally, the instructions for determining the boundary based on the map comprise instructions for: processing the map to determine first arrival positions of the ultrasound signals; and determining the boundary based on the determined first arrival positions.

The determination of the first arrival positions may be performed automatically. Optionally the determination of the first arrival positions is based on a time-of-flight picker algorithm, e.g., an improved Akaike information criterion picker algorithm.

The determination of the boundary may be based on coordinate transform operation.

Optionally, the instructions for determining respective optimal speed of sound value for each respective one of the plurality of subsets of ultrasound imaging data comprise instructions for: processing the first subset of ultrasound imaging data associated with one of the two sections of the ultrasound image to determine a first optimal speed of sound value associated with the one of the two sections, the first optimal speed of sound value is arranged for use in the image reconstruction operation; and/or processing the second subset of ultrasound imaging data associated with another one of the two sections of the ultrasound image to determine a second optimal speed of sound value associated with another one of the two sections, the second optimal speed of sound value is arranged for use in the image reconstruction operation.

Optionally, the instructions for determining respective optimal speed of sound value for each respective one of the plurality of subsets of ultrasound imaging data comprise instructions for: processing the first subset of ultrasound imaging data associated with the object to determine a first optimal speed of sound value associated with the object, the first optimal speed of sound value is arranged for use in the image reconstruction operation; and determining a second optimal speed of sound value associated with the coupling medium based on a temperature or an average temperature of the coupling medium at the time the ultrasound imaging data is acquired, the second optimal speed of sound value is arranged for use in the image reconstruction operation.

Optionally, the second optimal speed of sound value associated with the coupling medium is determined from a lookup table that maps a plurality of temperatures of the coupling medium with a plurality of speed of sound values.

Optionally, the instructions for processing the first subset of ultrasound imaging data associated with the one of the two sections (e.g., the object) to determine a first optimal speed of sound value associated with the one of the two sections (e.g., the object) comprise instructions for: processing the first subset of ultrasound imaging data respectively using each of a plurality of predetermined speed of sound values to determine a plurality of total coherence factor values, each respective one of the plurality of total coherence factor values being associated with the processing of the first subset of ultrasound imaging data using a respective one of the predetermined speed of sound values; and determining, based on the plurality of total coherence factor values, a speed of sound value that corresponds to the first optimal speed of sound value. Processing of the first subset of the ultrasound imaging data respectively using each of a plurality of predetermined speed of sound values involves processing the same first subset of ultrasound imaging data multiple times, each time using a respective predetermined speed of sound value. The multiple times of processing may occur simultaneously or sequentially. The determining of the speed of sound value that corresponds to the first optimal speed of sound value based on the plurality of total coherence factor values may include determining from the plurality of total coherence factor values the largest total coherence factor value, and determining the corresponding speed of sound value associated with the largest total coherence factor value as the first optimal speed of sound value.

Optionally, the instructions for processing the first subset of ultrasound imaging data respectively using each of a plurality of predetermined speed of sound values comprise instructions for: processing the first subset of ultrasound imaging data respectively using each of a plurality of predetermined speed of sound values to determine to determine a plurality of time of flight maps, each respective one of the plurality of time of flight maps being associated with the processing of the first subset of ultrasound imaging data using a respective one of the predetermined speed of sound values; for each of the plurality of time of flight maps, processing the time of flight map to determine a respective ultrasound image; and for each of the plurality of determined ultrasound images, determining a total coherence factor value based on a sum of coherence factor values of the coherence factor map. Processing of the first subset of ultrasound imaging data respectively using each of a plurality of predetermined speed of sound values involves processing the same first subset of ultrasound imaging data multiple times, each time using a respective predetermined speed of sound value. The multiple times of processing may occur simultaneously or sequentially.

Optionally, the instructions for determining a speed of sound value based on the plurality of total coherence factor values comprise instructions for: determining a total coherence factor value function based on the plurality of total coherence factor values; and determining a speed of sound value corresponding to an extreme (e.g., maximum) value of the total coherence factor value function, the determined speed of sound value corresponds to the first optimal speed of sound value.

Optionally, the instructions for determining a total coherence factor value function comprise instructions for performing an interpolation operation using the plurality of total coherence factor values. The interpolation operation may include a spline interpolation operation, a linear interpolation operation, a polynomial interpolation operation, etc.

Optionally, the instructions for determining a speed of sound value corresponding to an extreme (e.g., maximum) value of the total coherence factor value function comprise instructions for determining a speed of sound value corresponding to an extreme (e.g., maximum) value of the total coherence factor value function by processing only an extreme (peak/trough) portion of the total coherence factor value function.

Optionally, the plurality of time of flight maps are determined based on multi-stencil fast marching method.

Optionally, for each respective one of the plurality of the ultrasound images, the coherence factor value of each pixel can be determined based on $$CF_{SoS_{sample}}(x, y) = \frac{\left|\sum_{Rcv=1}^{N_{elm}} \sum_{Tx=1}^{N_{elm}} I(x, y)\right|^2}{N_{elm} \times \sum_{Rcv=1}^{N_{elm}} \left|\sum_{Tx=1}^{N_{elm}} I(x, y)\right|^2}$$

where (x,y) represents the pixel of the ultrasound image, $SoS_{sample}$ is an predetermined speed of sound value, Tx and Rcv are transducer elements of the system for photoacoustic imaging and ultrasound imaging that are operated as ultrasound waves transmitters and ultrasound waves receivers respectively, $N_{elm}$ is number of transducer elements of the system for photoacoustic imaging and ultrasound imaging, I(x,y) is a delayed channel data calculated from the time of flight map.

Optionally, the one or more programs further comprise instructions for: obtaining corresponding photoacoustic imaging data representative of a corresponding photoacoustic image of the object, the photoacoustic imaging data being obtained from the system for photoacoustic imaging and ultrasound imaging.

Optionally, the instructions for performing the image reconstruction operation comprise instructions for: processing the photoacoustic imaging data based on the determined first and second optimal speed of sound values to reconstruct a photoacoustic image of the object.

Optionally, the instructions for performing the image reconstruction operation comprise instructions for: processing the ultrasound imaging data based on the determined first and second optimal speed of sound values to reconstruct an ultrasound image of the object.

Optionally, the system further comprises: a display operably connected with the one or more processors, the display is arranged to display the reconstructed or processed ultrasound image and the reconstructed or processed photoacoustic image. The display may be arranged to display the reconstructed or processed ultrasound image and the reconstructed or processed photoacoustic image separately and/or combined (e.g., overlaid).

Optionally, the ultrasound imaging data and the corresponding photoacoustic imaging data represent co-registered ultrasound image and photoacoustic image of the object (of the same imaging plane).

Optionally, the instructions for performing the speed of sound value optimization operation comprises: selecting one of the first optimization operation and the second optimization operation for performing the optimization operation. In some examples, the selection may be based on characteristics of the imaging data or performance parameters of the system. In some examples, the selection may be based on user input.

In a second aspect, there is provided a method for processing photoacoustic and ultrasound imaging data. The method comprises obtaining ultrasound imaging data representative of an ultrasound image of an object, the ultrasound imaging data being obtained from a system for photoacoustic imaging and ultrasound imaging, e.g., as a result of an operation mode for ultrasound imaging; performing a speed of sound value optimization operation based on the ultrasound imaging data for facilitating image reconstruction; and performing an image reconstruction operation. The object may be an animal (e.g., rat, mouse, mice, rabbit, monkey, etc.), human, an imaging phantom, a biological tissue, etc.

Optionally, performing the speed of sound value optimization operation comprises: processing the ultrasound imaging data to determine an optimal speed of sound value, the optimal speed of sound value is for use in the image reconstruction operation. In one example, this speed of sound value optimization operation corresponds to a first optimization operation.

Optionally, processing the ultrasound imaging data to determine an optimal speed of sound value comprises processing only the ultrasound imaging data in a predetermined region of interest to determine an optimal speed of sound value.

Optionally, processing the ultrasound imaging data to determine an optimal speed of sound value comprises: processing the ultrasound imaging data respectively using each of a plurality of predetermined speed of sound values to determine a plurality of total coherence factor values, each respective one of the plurality of total coherence factor values being associated with the processing of the ultrasound imaging data using a respective one of the predetermined speed of sound values; and determining, based on the plurality of total coherence factor values, a speed of sound value that corresponds to the optimal speed of sound value. Processing of the ultrasound imaging data respectively using each of a plurality of predetermined speed of sound values involves processing the same set of ultrasound imaging data multiple times, each time using a respective predetermined speed of sound value. The multiple times of processing may occur simultaneously or sequentially. The determining of the speed of sound value that corresponds to the optimal speed of sound value based on the plurality of total coherence factor values may include determining from the plurality of total coherence factor values the largest total coherence factor value, and determining the corresponding speed of sound value associated with the largest total coherence factor value as the optimal speed of sound value.

Optionally, processing the ultrasound imaging data respectively using each of a plurality of predetermined speed of sound values comprises: processing the ultrasound imaging data respectively using each of a plurality of predetermined speed of sound values to determine a plurality of coherence factor maps, each respective one of the plurality of coherence factor maps is determined using a respective one of the predetermined speed of sound values; and for each respective one of the plurality of coherence factor maps, determining a respective total coherence factor value based on a sum of the coherence factor values of the coherence factor map. Processing of the ultrasound imaging data respectively using each of a plurality of predetermined speed of sound values involves processing the same set of ultrasound imaging data multiple times, each time using a respective predetermined speed of sound value. The multiple times of processing may occur simultaneously or sequentially.

Optionally, determining a speed of sound value based on the plurality of total coherence factor values comprises: determining a total coherence factor value function based on the plurality of total coherence factor values; and determining a speed of sound value corresponding to an extreme (e.g., maximum) value of the total coherence factor value function, the determined speed of sound value corresponds to the optimal speed of sound value.

Optionally, determining a total coherence factor value function comprises performing an interpolation operation using the plurality of total coherence factor values. The interpolation operation may include a spline interpolation operation, a linear interpolation operation, a polynomial interpolation operation, etc.

Optionally, for each respective one of the coherence factor map, the coherence factor value of each pixel can be determined based on $$CF_{v_i}(n) = \frac{\left|\sum_{Rcv=1}^{N_{elm}} \sum_{Tx=1}^{N_{elm}} I(n)\right|^2}{N_{elm} \times \sum_{Rcv=1}^{N_{elm}} \left|\sum_{Tx=1}^{N_{elm}} I(n)\right|^2}$$

where n represents the pixel position on the coherence factor map, $v_i$ is the predetermined speed of sound value, Tx and Rcv are the transducer elements operated as ultrasound waves transmitters and ultrasound waves receivers respectively, $N_{elm}$ is the number of transducer elements, I(n) is a delayed channel data according to $v_i$ and a distance of flight representative of a distance between the pixel position and the transducer element operated as ultrasound waves receiver.

Optionally, performing the image reconstruction operation comprises: processing the ultrasound imaging data based on the determined optimal speed of sound value to reconstruct an ultrasound image of the object. The processing may be automatically performed upon or after determining the optimal speed of sound value.

Optionally, the method further comprises: obtaining corresponding photoacoustic imaging data representative of a corresponding photoacoustic image of the object, the photoacoustic imaging data being obtained from the system for photoacoustic imaging and ultrasound imaging, e.g., as a result of an operation mode for photoacoustic imaging.

Optionally, performing the image reconstruction operation comprises: processing the photoacoustic imaging data based on the determined optimal speed of sound value to reconstruct a photoacoustic image of the object. The processing may be automatically performed upon or after determining the optimal speed of sound value.

Optionally, processing the photoacoustic imaging data based on the determined optimal speed of sound value comprises: processing the photoacoustic imaging data using a delay-and-sum beamforming method based on the determined optimal speed of sound value to reconstruct the photoacoustic image of the object. The delay-and-sum beamforming method may be a weighted delay-and-sum beamforming method.

Optionally, processing the ultrasound imaging data based on the determined optimal speed of sound value comprises: processing the ultrasound imaging data using a delay-and-sum beamforming method based on the determined optimal speed of sound value to reconstruct the ultrasound image of the object. The delay-and-sum beamforming method may be a weighted delay-and-sum beamforming method.

Optionally, processing the photoacoustic imaging data based on the determined optimal speed of sound value comprises processing only the photoacoustic imaging data in a predetermined region of interest.

Optionally, the method further comprises: processing the photoacoustic imaging data using a bandpass filter prior to processing the ultrasound imaging data based on the determined optimal speed of sound value. The bandpass filter may be arranged to provide a passband in about 0 MHz to about 10 MHz, or about 0 MHz to about 8.5 MHz. The bandpass filter may be a Butterworth filter, e.g., a $3^{rd}$ order Butterworth filter.

Optionally, the method further comprises: processing the reconstructed photoacoustic image, the processing comprises filtering the reconstructed photoacoustic image.

Optionally, processing the ultrasound imaging data based on the determined optimal speed of sound value comprises processing only the ultrasound imaging data in a predetermined region of interest.

Optionally, the method further comprises: processing the ultrasound imaging data using a bandpass filter prior to processing the ultrasound imaging data based on the determined optimal speed of sound value. The bandpass filter may be arranged to provide a passband in about 0 MHz to about 10 MHz, or about 0 MHz to about 8.5 MHz. The bandpass filter may be a Butterworth filter, e.g., a $3^{rd}$ order Butterworth filter.

Optionally, the method further comprises: processing the reconstructed ultrasound image, the processing comprises filtering the reconstructed ultrasound image Optionally, performing the speed of sound value optimization operation comprises: performing a segmentation operation on the ultrasound imaging data to obtain a plurality of subsets of ultrasound imaging data; and determining for each respective one of the plurality of subsets of ultrasound imaging data, a respective optimal speed of sound value for use in the image reconstruction operation. In one example, this speed of sound value optimization operation corresponds to a second optimization operation.

Optionally, performing a segmentation operation on the ultrasound imaging data comprises: processing the ultrasound imaging data to determine a boundary between two sections of the ultrasound image, e.g., a boundary between the object and a coupling medium (a medium arranged between the object and the transducer elements during imaging) in the ultrasound image; and dividing the ultrasound imaging data into, at least, a first subset of ultrasound imaging data associated with one of the two sections (e.g., the object) and a second subset of ultrasound imaging data associated with another one of the two sections (e.g., the coupling medium). Optionally, the boundary is an endless boundary. Optionally, the ultrasound imaging data may be divided into further subset(s) of the ultrasound imaging data. The coupling medium may be liquid, e.g., water, oil, etc.

Optionally, processing the ultrasound imaging data to determine a boundary between two sections of the ultrasound image comprises: determining a map based on ultrasound signals received by each respective transducer element as a result of ultrasound waves detected at the transducer element in response to the transmission of ultrasound waves by the transducer element towards the object; and determining the boundary based on the map.

Optionally, determining the boundary based on the map comprises: processing the map to determine first arrival positions of the ultrasound signals; and determining the boundary based on the determined first arrival positions.

The determination of the first arrival positions may be performed automatically. Optionally the determination of the first arrival positions is based on a time-of-flight picker algorithm, e.g., an improved Akaike information criterion picker algorithm.

The determination of the boundary may be based on coordinate transform operation.

Optionally, determining respective optimal speed of sound value for each respective one of the plurality of subsets of ultrasound imaging data comprises: processing the first subset of ultrasound imaging data associated with one of the two sections of the ultrasound image to determine a first optimal speed of sound value associated with the one of the two sections, the first optimal speed of sound value is arranged for use in the image reconstruction operation; and/or processing the second subset of ultrasound imaging data associated with another one of the two sections of the ultrasound image to determine a second optimal speed of sound value associated with another one of the two sections, the second optimal speed of sound value is arranged for use in the image reconstruction operation.

Optionally, determining respective optimal speed of sound value for each respective one of the plurality of subsets of ultrasound imaging data comprises: processing the first subset of ultrasound imaging data associated with the object to determine a first optimal speed of sound value associated with the object, the first optimal speed of sound value is arranged for use in the image reconstruction operation; and determining a second optimal speed of sound value associated with the coupling medium based on a temperature or an average temperature of the coupling medium at the time the ultrasound imaging data is acquired, the second optimal speed of sound value is arranged for use in the image reconstruction operation.

Optionally, the second optimal speed of sound value associated with the coupling medium is determined from lookup table that maps a plurality of temperatures of the coupling medium with a plurality of speed of sound values.

Optionally, processing the first subset of ultrasound imaging data associated with one of the two sections (e.g., the object) to determine a first optimal speed of sound value associated with the one of the two sections (e.g., object) comprises: processing the first subset of ultrasound imaging data respectively using each of a plurality of predetermined speed of sound values to determine a plurality of total coherence factor values, each respective one of the plurality of total coherence factor values being associated with the processing of the first subset of ultrasound imaging data using a respective one of the predetermined speed of sound values; and determining, based on the plurality of total coherence factor values, a speed of sound value that corresponds to the first optimal speed of sound value. Processing of the first subset of the ultrasound imaging data respectively using each of a plurality of predetermined speed of sound values involves processing the same first subset of ultrasound imaging data multiple times, each time using a respective predetermined speed of sound value. The multiple times of processing may occur simultaneously or sequentially. The determining of the speed of sound value that corresponds to the first optimal speed of sound value based on the plurality of total coherence factor values may include determining from the plurality of total coherence factor values the largest total coherence factor value, and determining the corresponding speed of sound value associated with the largest total coherence factor value as the first optimal speed of sound value.

Optionally, processing the first subset of ultrasound imaging data respectively using each of a plurality of predetermined speed of sound values comprises: processing the first subset of ultrasound imaging data respectively using each of a plurality of predetermined speed of sound values to determine to determine a plurality of time of flight maps, each respective one of the plurality of time of flight maps being associated with the processing of the first subset of ultrasound imaging data using a respective one of the predetermined speed of sound values; for each of the plurality of time of flight maps, processing the time of flight map to determine a respective ultrasound image; and for each of the plurality of the determined ultrasound images, determining a total coherence factor value based on a sum of coherence factor values of the coherence factor map. Processing of the first subset of ultrasound imaging data respectively using each of a plurality of predetermined speed of sound values involves processing the same first subset of ultrasound imaging data multiple times, each time using a respective predetermined speed of sound value. The multiple times of processing may occur simultaneously or sequentially.

Optionally, determining a speed of sound value based on the plurality of total coherence factor values comprises: determining a total coherence factor value function based on the plurality of total coherence factor values; and determining a speed of sound value corresponding to an extreme (e.g., maximum) value of the total coherence factor value function, the determined speed of sound value corresponds to the first optimal speed of sound value.

Optionally, determining a total coherence factor value function comprises performing an interpolation operation using the plurality of total coherence factor values. The interpolation operation may include a spline interpolation operation, a linear interpolation operation, a polynomial interpolation operation, etc.

Optionally, determining a speed of sound value corresponding to an extreme (e.g., maximum) value of the total coherence factor value function comprises determining a speed of sound value corresponding to an extreme (e.g., maximum) value of the total coherence factor value function by processing only an extreme (peak/trough) portion of the total coherence factor value function.

Optionally, the plurality of time of flight maps are determined based on multi-stencil fast marching method.

Optionally, for each respective one of the plurality of the ultrasound images, the coherence factor value of each pixel can be determined based on $$CF_{SoS_{sample}}(x, y) = \frac{\left|\sum_{Rcv=1}^{N_{elm}} \sum_{Tx=1}^{N_{elm}} I(x, y)\right|^2}{N_{elm} \times \sum_{Rcv=1}^{N_{elm}} \left|\sum_{Tx=1}^{N_{elm}} I(x, y)\right|^2}$$

where (x,y) represents the pixel of the ultrasound image, $SoS_{sample}$ is an predetermined speed of sound value, Tx and Rcv are the transducer elements operated as ultrasound waves transmitters and ultrasound waves receivers respectively, $N_{elm}$ is the number of transducer elements, I(x,y) is a delayed channel data calculated from the time of flight map.

Optionally, the method further comprises: obtaining corresponding photoacoustic imaging data representative of a corresponding photoacoustic image of the object, the photoacoustic imaging data being obtained from the system for photoacoustic imaging and ultrasound imaging, e.g., as a result of an operation mode for photoacoustic imaging.

Optionally, performing the image reconstruction operation comprises processing the photoacoustic imaging data based on the determined first and second optimal speed of sound values to reconstruct a photoacoustic image of the object.

Optionally, performing the image reconstruction operation comprises: processing the ultrasound imaging data based on the determined first and second optimal speed of sound values to reconstruct an ultrasound image of the object.

Optionally, the method further comprises: displaying the reconstructed or processed ultrasound image and the reconstructed or processed photoacoustic image, separately and/or combined (e.g., overlaid).

Optionally, the ultrasound imaging data and the corresponding photoacoustic imaging data represent co-registered ultrasound image and photoacoustic image of the object (of the same imaging plane).

Optionally, performing the speed of sound value optimization operation comprises: selecting one of the first optimization operation and the second optimization operation for performing the optimization operation. In some examples, the selection may be based on characteristics of the imaging data or performance parameters of the system. In some examples, the selection may be based on user input.

In a third aspect, there is provided a non-transitory computer-readable storage medium storing one or more programs configured to be executed by one or more processors, the one or more programs including instructions for performing or facilitating performing of the method of the second aspect.

In a fourth aspect, there is provided a computer program comprising instructions which, when the computer program is executed by a computer, cause or facilitate the computer to carry out method of the second aspect.

In a fifth aspect, there is provided a system for photoacoustic imaging and ultrasound imaging, comprising the system of the first aspect. The system for photoacoustic imaging and ultrasound imaging is operable to perform both photoacoustic imaging and ultrasound imaging, selectively or substantially simultaneously, to obtain photoacoustic imaging data and ultrasound imaging data of the same imaging section of the object.

In a sixth aspect, there is provided a system for photoacoustic imaging and ultrasound imaging, comprising: a laser module operable to irradiate an object with laser radiation; a transducer unit comprising a plurality of transducer elements; and a control unit operably coupled with the irradiation unit and the transducer unit and for controlling operation of the transducer unit. The transducer unit is operable to (i) detect ultrasound waves generated by the object in response to the laser module irradiating the object with the laser radiation, and generate electric signals that form the photoacoustic imaging data based on the detected ultrasound waves; and (ii) transmit ultrasound waves towards the object and, in response, detect ultrasound waves reflected, scattered, and/or transmitted by the object, for facilitating ultrasound imaging, and generate electric signals that form the ultrasound imaging data based on the detected ultrasound waves. The object may be an animal (e.g., rat, mouse, mice, rabbit, monkey, etc.), human, phantom, tissue sample, etc. The system for photoacoustic imaging and ultrasound imaging may be a preclinical imaging system, a clinical imaging system, etc. The system for photoacoustic imaging and ultrasound imaging is operable to perform both photoacoustic imaging and ultrasound imaging, selectively or substantially simultaneously, to obtain photoacoustic imaging data and ultrasound imaging data of the same imaging section of the object.

Optionally, the system further comprises the system of the first aspect. The system of the first aspect may process photoacoustic and ultrasound imaging data regardless of the operation status of the system for photoacoustic imaging and ultrasound imaging. Preferably, the system of the first aspect is operable to process photoacoustic imaging data and/or ultrasound imaging data during operation of the system for photoacoustic imaging and ultrasound imaging, to facilitate real time or substantially real time processing and display of photoacoustic and ultrasound images (or video of multiple images).

Optionally, the laser module comprises a laser source operable to provide laser pulses. The laser source may be a Q-switched Nd:YAG laser source. The laser source may provide laser pulses of one or more wavelengths. The laser pulses may be in a wavelength of about 1064 nm, which can provide high pulse energy and low scattering. The laser pulses may be nanosecond laser pulses. The laser source may have a pulse repetition rate of 20 Hz.

Optionally, the laser module further comprises a laser fiber unit optically coupled with the laser source for directing the laser radiation towards the object. In one example, the laser fiber unit comprises a plurality of laser fiber modules optically coupled with the laser source, the plurality of laser fiber modules are angularly distributed (around the object when the object is being imaged) and are each arranged to direct the laser radiation towards the object. In one example, the laser fiber unit or the plurality of laser fiber modules are arranged to emit the laser radiation at an angle relative to an imaging plane of the object. The angle may be about 40 to about 60 degrees, about 50 to about 70 degrees, about 55 to about 65 degrees, or about 60 degrees.

Optionally, the laser module further comprises a filter and a coupler operably coupled between the laser source and the laser fiber unit.

Optionally, the plurality of transducer elements are angularly distributed (around the object when the object is being imaged). The plurality of transducer elements may be arranged in a ring-shaped array. The plurality of transducer elements may be the same size and/or structure, or a plurality of sizes and/or structures. The plurality of transducer elements may include 256 transducer elements, 512 transducer elements, 1024 transducer elements, etc. The plurality of transducer elements may be angularly distributed (around the object when the object is being imaged, preferably with the object located in a centre or central region surrounded by the transducer elements). The plurality of transducer elements may cover angular range of >300 degrees, e.g., about 360 degrees, around the object.

Optionally, each of the plurality of transducer elements are cylindrically focused in elevational direction.

Optionally, the control unit comprise a data acquisition unit. Optionally, the control unit comprises a multiplexing unit. Optionally the control unit comprises multiple channels for the transducer elements, e.g., one channel for each respective transducer element. Optionally, each of the transducer elements is connected with an amplifier, e.g., one amplifier for each respective transducer element. The gain of the amplifier can be programmed or adjusted.

Optionally, the control unit is operable to selectively operate each of the plurality of transducer elements as ultrasound waves transmitter and ultrasound waves receiver.

Optionally, the control unit is operable to selectively operate the transducer unit in at least one operation mode for photoacoustic imaging and at least one operation mode for ultrasound imaging.

Optionally, in an operation mode for photoacoustic imaging, the control unit controls some or all of the plurality of transducer elements to operate as ultrasound waves receivers to receive the ultrasound waves in response to the laser module irradiating the object with the laser radiation. In some examples, this operation mode for photoacoustic imaging generates a set of photoacoustic imaging data, e.g., for processing by the system of the first aspect.

Optionally, in an operation mode for ultrasound imaging, the control unit selectively and sequentially controls each of the plurality of transducer elements to operate as ultrasound waves transmitter for transmitting the ultrasound waves towards the object, and for each ultrasound wave transmitter, controls some of the plurality of transducer elements as ultrasound waves receivers for receiving the ultrasound waves reflected, scattered, and/or transmitted by the object in response to the transmission of the ultrasound waves towards the object. In some examples, this operation mode for ultrasound imaging generates a set of ultrasound imaging data, e.g., for processing by the system of the first aspect.

Optionally, for each ultrasound wave transmitter, the some of the plurality of transducer elements controlled to operate as ultrasound waves receivers comprise: the transducer element operated as the ultrasound waves transmitter and a plurality of transducer elements adjacent to the transducer element operated as the transmitter. Optionally, the control unit switches off, e.g., temporarily, the remaining plurality of transducer elements not controlled to operate as ultrasound waves receivers.

Optionally, the plurality of transducer elements adjacent to the transducer element operated as the ultrasound waves transmitter are arranged on two sides of the transducer element operated as the ultrasound waves transmitter.

Optionally, the control unit is arranged to implement a first imaging sequence with one or more cycles, and for each of the one or more cycles, the control unit operates the transducer unit in the operation mode for photoacoustic imaging once and operates the transducer unit in the operation mode for ultrasound imaging once. In one example, the first imaging sequence include multiple cycles repeated at 10 Hz.

Optionally, for each of the one or more cycles of the first imaging sequence, the control unit operates the transducer unit in the operation mode for photoacoustic imaging once and then operates the transducer unit in the operation mode for ultrasound imaging once. Optionally, each cycle is about 0.1 seconds.

Optionally, for each of the one or more cycles of the first imaging sequence, the control unit operates the transducer unit in the operation mode for ultrasound imaging once and then operates the transducer unit in the operation mode for photoacoustic imaging once. Optionally, each cycle is about 0.1 seconds.

Optionally, the control unit is arranged to implement a second imaging sequence with one or more cycles, and for each of the one or more cycles of the second imaging sequence, the control unit operates the transducer unit in the operation mode for photoacoustic imaging multiple times and operates the transducer unit in the operation mode for ultrasound imaging once.

Optionally, for each of the one or more cycles of the second imaging sequence, the control unit operates the transducer unit in the operation mode for ultrasound imaging once and then consecutively operates the transducer unit in the operation mode for photoacoustic imaging multiple times. The control unit consecutively may operate the transducer unit in the operation mode for photoacoustic imaging multiple times at a rate of about 20 Hz.

Other features and aspects of the invention will become apparent by consideration of the detailed description and accompanying drawings. Any feature(s) described herein in relation to one aspect or embodiment may be combined with any other feature(s) described herein in relation to any other aspect or embodiment as appropriate and applicable.

Terms of degree such that "generally", "about", "substantially", or the like, are, depending on context, used to take into account manufacture tolerance, degradation, trend, errors, tendency, imperfect practical conditions, etc.

As used herein, unless otherwise specified, "US" refers to ultrasound and "PA" refers to photoacoustic.

BRIEF DESCRIPTION OF THE DRAWINGS

Embodiments of the invention will now be described, by way of example, with reference to the accompanying drawings in which:

FIG. 1 is a schematic diagram of a system including an imaging system and a data processing system in one embodiment;

FIG. 2 is a schematic diagram of a system including an imaging system and a data processing system in one embodiment;

FIG. 14 is an illustration of ground truth of a numerical phantom in a numerical phantom (with two anechoic regions R1, R2) simulation and reconstruction in one embodiment;

FIG. 15A is an illustration of ultrasound and photoacoustic images (overlaid) reconstructed with a suboptimal (wrong) speed of sound value in the numerical phantom simulation and reconstruction;

FIG. 15B is an illustration of ultrasound and photoacoustic images (overlaid) reconstructed with an optimized (adaptive) speed of sound value in the numerical phantom simulation and reconstruction;

FIG. 16 is a graph showing diameters of anechoic regions of the numerical phantom in the reconstructed images of FIG. 15A and FIG. 15B;

FIG. 17 is an illustration of ground truth in a numerical breast phantom simulation and reconstruction in one embodiment;

FIG. 18A is an illustration of ultrasound and photoacoustic images (overlaid) reconstructed with a suboptimal (wrong) speed of sound value in the numerical breast phantom simulation and reconstruction;

FIG. 18B is an illustration of ultrasound and photoacoustic images (overlaid) reconstructed with an optimized (adaptive) speed of sound value in the numerical breast phantom simulation and reconstruction;

FIG. 19 is a zoom in view of the boxes in FIGS. 18A and 18B;

FIG. 20A is an illustration of imaging result of ultrasound imaging of a tungsten wire with a diameter of 20 μm, acquired with the tungsten wire located at different positions, using the imaging system of FIG. 5;

FIG. 20B is an illustration of imaging result of photoacoustic imaging of a tungsten wire with a diameter of 20 μm, acquired with the tungsten wire located at different positions, using the imaging system of FIG. 5;

FIG. 21A is a graph showing measured in-plane axial and tangential resolution of the ultrasound imaging of the tungsten wire as a function of distance from the transducer array center, with the shadowed region showing a range with isotropic resolution;

FIG. 21B is a graph showing measured in-plane axial and tangential resolution of the photoacoustic imaging of the tungsten wire as a function of distance from the transducer array center, with the shadowed region showing a range with isotropic resolution;

FIG. 24A is an illustration of a mice and the cross sections imaged by the imaging system of FIG. 5;

FIG. 24B is a graph showing variation of the total coherence factor, or coherence factor summation (CFS) value, for different calculated average speed of sound value for each of the cross sections illustrated in FIG. 24A;

FIG. 39B is an illustration of the photoacoustic images of the chicken breast phantom of FIG. 39A reconstructed with a single speed of sound value for the entire field of view and reconstructed with two speed of sound values (one for the object another for the coupling medium);

FIG. 39C is a zoom in view of the boxes in FIG. 39B;

DETAILED DESCRIPTION

Figure 3:
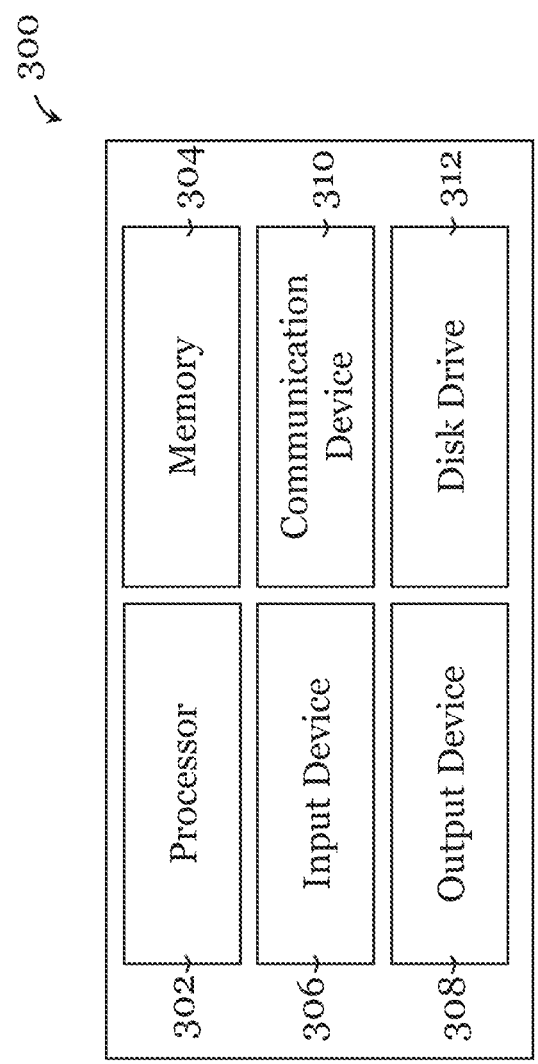
FIG. 3 is a functional block diagram of an information handling system operable as a data processing system in one embodiment.

FIG. 1 shows an example system 100 including an imaging system 102 and a data processing system 104. The imaging system 102 includes necessary hardware, and optionally software, for performing, at least, photoacoustic imaging and ultrasound imaging. The imaging system 102 can be a clinical or preclinical imaging system used for imaging objects such as animals, humans, phantoms, samples, etc. The imaging system 102 may be used to perform photoacoustic imaging only, ultrasound imaging only, or hybrid photoacoustic imaging and ultrasound imaging. Hybrid photoacoustic imaging and ultrasound imaging involves performing photoacoustic imaging and ultrasound imaging, preferably substantially simultaneously, to obtain different types of image data of the same section or part of the object. The data processing system 104 may be used to process the imaging data obtained by the imaging system 102. Specifically the data processing system 104 may be used to process photoacoustic imaging data and ultrasound imaging data for reconstructing photoacoustic and ultrasound images. The data processing system 104 may operate to process imaging data online or offline. In some embodiments, the data processing system 104 may support substantially real-time data processing and image display, during operation of the imaging system 102, to enable video-rate images presentation. The data processing system 104 may obtain imaging data directly or indirectly from the imaging system 102. In some embodiments, the imaging system 102 and the data processing system 104 are incorporated in the same apparatus. In some other embodiments, the imaging system 102 and the data processing system 104 are arranged in different apparatuses. In some embodiments, the data processing system may be implemented at least partly in a computing network, e.g., cloud computing network.

FIG. 2 is a system 200 including an imaging system 202 and a data processing system 204. System 200 can be considered as a specific example of the system too: the imaging system 202 is a specific example of the imaging system 102, and the data processing system 204 is generally the same as the data processing system 104. The following description will focus on the difference of the system 200 over system too.

In this embodiment, the imaging system 202 is arranged to perform photoacoustic imaging and ultrasound imaging. The imaging system 202 includes an irradiation unit 202A, a transducer unit 202B, and a control unit 202C.

The irradiation unit 202A is arranged to irradiate an object to be imaged with electromagnetic radiation such as light. In one embodiment, the irradiation unit 202A includes a laser module operable to irradiate an object with laser radiation, to enable photoacoustic imaging of the object. The laser module may include one or more laser sources. The laser source(s) may be arranged to provide laser pulses, e.g., nanosecond laser pulses. The laser source(s) may be arranged to provide laser pulses at a pulse repetition rate of 10 Hz or more. The laser source(s) may be arranged to provide laser pulses of one or more wavelengths (e.g., 1064 nm, 532 nm, etc.). The laser source(s) may include a Q-switched Nd:YAG laser source. The laser module may further include a laser fiber unit optically coupled with the laser source, optionally via a filter and a coupler in between, for directing the laser radiation towards the object when the object is being imaged. The laser fiber unit may include one or more laser fiber modules optically coupled with the laser source and arranged around the object to direct the laser radiation towards the object when the object is being imaged. In some embodiments, the laser fiber unit includes multiple laser fiber modules angularly distributed around, and optionally equidistant from, the object when the object is being imaged. The laser fiber unit or the laser fiber module(s) may be arranged to emit the laser radiation at an angle relative to an imaging plane of the object. The angle may be about 40 to about 60 degrees, about 50 to about 70 degrees, about 55 to about 65 degrees, or about 60 degrees.

The transducer unit 202B includes multiple transducer elements operable to emit and/or detect ultrasound waves. In some embodiments, one or more of the transducer elements are arranged to emit but not receive ultrasound waves. In some embodiments, one or more of the transducer elements are arranged to receive but not emit ultrasound waves. In some embodiments, one or more of the transducer elements are arranged to both emit and receive (selectively) ultrasound waves. The transducer unit 202B is operable to (i) detect ultrasound waves generated by the object in response to the laser module irradiating the object with the laser radiation, and generate electric signals that form photoacoustic imaging data based on the detected ultrasound waves, and (ii) transmit ultrasound waves towards the object and, in response, detect ultrasound waves reflected, scattered, and/or transmitted by the object, for facilitating ultrasound imaging, and generate electric signals that form ultrasound imaging data based on the detected ultrasound waves. The transducer elements may be arranged in a linear array, a curved (concave) array, or a ring-shaped array. In one embodiment, the transducer elements are arranged angularly distributed around the object when the object is being imaged. The different transducer elements may or may not be the same size and/or structure. In some examples, the transducer unit 202B includes 256 transducer elements, 512 transducer elements, 1024 transducer elements, etc. The transducer elements, arranged in curved or ring-shaped array, may be angularly distributed around the object when the object is being imaged, preferably with the object located in a center or central region surrounded by the transducer elements. The transducer elements, arranged in curved array, may cover an angular range of any number of degrees around the object. At least some of the transducer elements may be cylindrically focused in elevational direction.

The control unit 202C is operably coupled with the irradiation unit 202A and the transducer unit 202B and for controlling operation of the transducer unit 202B and optionally the irradiation unit 202A. The control unit 202C may include a data acquisition unit, a multiplexing unit, etc. The control unit 202C provides multiple channels for the transducer elements, preferably one channel for each respective transducer element. Each of the channels may be provided with an amplifier, the gain of which may be adjusted. The control unit 202C can selectively operate the transducer elements of the transducer unit 202B as ultrasound waves transmitter(s) and ultrasound waves receiver(s), and may selectively operate the transducer unit 202B in one or more operation mode(s) for photoacoustic imaging and one or more operation mode(s) for ultrasound imaging.

In one example operation mode for photoacoustic imaging, the control unit 202C, based on the operation or activation of the irradiation unit 202A, controls some or all of the transducer elements to simultaneously operate as ultrasound waves receivers to receive the ultrasound waves in response to the laser module irradiating the object with the laser radiation (laser pulse). In one example, the control unit 202C controls the transducer elements to simultaneously operate as ultrasound waves receivers for a predetermined duration after the emission of laser pulse by the laser module.

In one example operation mode for ultrasound imaging, the control unit 202C selectively and sequentially controls each of the transducer elements to operate as ultrasound waves transmitter for transmitting the ultrasound waves towards the object, and, for each ultrasound wave transmitter, controls some or all of the transducer elements as ultrasound waves receivers for receiving the ultrasound waves reflected, scattered, and/or transmitted by the object in response to the transmission of the ultrasound waves towards the object by the ultrasound wave transmitter. In a more specific example, the control unit 202C first controls one of the transducer elements to operate as ultrasound waves transmitter and controls some of the transducer elements as ultrasound waves receivers for receiving the ultrasound waves reflected, scattered, and/or transmitted by the object in response to the transmission of the ultrasound waves towards the object by the ultrasound wave transmitter. The control unit 202C then repeats this process for different transducer elements. For each round, the transducer elements controlled to operate as ultrasound waves receivers may include the transducer element that operates as the ultrasound waves transmitter for that round and multiple transducer elements adjacent to it. For each round, transducer elements not controlled to operate as ultrasound waves receivers may be switched off. The multiple transducer elements adjacent to the transducer element that operates as the ultrasound waves transmitter may be arranged on two sides of the transducer element. The operation mode(s) for photoacoustic imaging and the operation mode(s) for ultrasound imaging can be combined to form different imaging sequence.

The imaging system 200 may include other modules not specifically illustrated in FIG. 2. For example, the imaging system 200 may include one or more of: a holder for holding a sample or animal to be imaged; a support for supporting a human body or body part to be imaged; an anesthesia module for providing anesthesia to the animal during imaging; a container for containing a coupling medium (e.g., fluid, e.g., liquid, water/oil) in which the sample or animal to be imaged is partly immersed; a temperature sensor (e.g., thermocouple) for detecting temperature of the coupling medium and/or object being imaged; a movement module (e.g., motorized device) for controlling relative movement (rotation and/or translation) of the holder and the transducers, etc.

FIG. 3 is a functional block diagram of an information handling system 300 in one embodiment. The information handling system 300 can be used as a data processing system (such as data processing system 104, 204) for processing imaging data such as photoacoustic imaging data and ultrasound imaging data, a system for controlling operation of an imaging system (such as imaging system 102, 202). The system 300 may be used to implement one or more of the methods (at least part of it) of the invention. The information handling system generally comprises suitable components necessary to receive, store, and execute appropriate computer instructions, commands, or codes. The main components of the information handling system 300 are a processor 302 and a memory (storage) 304. The processor 302 may include one or more: CPU(s), MCU(s), logic circuit(s), Raspberry Pi chip(s), digital signal processor(s) (DSP), application-specific integrated circuit(s) (ASIC), field-programmable gate array(s) (FPGA), and/or any other digital or analog circuitry/circuitries configured to interpret and/or to execute program instructions and/or to process signals and/or information and/or data. The memory 304 may include one or more volatile memory (such as RAM, DRAM, SRAM), one or more non-volatile memory (such as ROM, PROM, EPROM, EEPROM, FRAM, MRAM, FLASH, SSD, NAND, NVDIMM), or any of their combinations. Appropriate computer instructions, commands, codes, information and/or data may be stored in the memory 304. For example, the memory 304 may store one or more of: photoacoustic imaging data and ultrasound imaging data obtained by an imaging system; photoacoustic imaging data and ultrasound imaging data processed by the system 300; photoacoustic images and ultrasound images processed or reconstructed by the system 300; one or more computer program or computer instructions for implementing or performing a method of processing photoacoustic and ultrasound imaging data (such as but not limit to those described herein); one or more computer program or computer instructions for controlling operation of the imaging system, etc. Optionally, the information handling system 300 further includes one or more input devices 306. Examples of such input device 306 include: keyboard, mouse, stylus, image scanner, microphone, tactile/touch input device (e.g., touch sensitive screen), image/video input device (e.g., camera), etc. The input device 306 may be used to receive user input (e.g., speed of sound selection). Optionally, the information handling system 300 further includes one or more output devices 308. Examples of such output device 308 include: display (e.g., monitor, screen, projector, etc.), speaker, disk drive, headphone, earphone, printer, additive manufacturing machine (e.g., 3D printer), etc. The display may include a LCD display, a LED/OLED display, or any other suitable display, which may or may not be touch sensitive. This display may be used to show the reconstructed and/or processed image and associated data/measurements. The information handling system 300 may further include one or more disk drives 312 which may include one or more: solid state drive, hard disk drive, optical drive, flash drive, magnetic tape drive, etc. A suitable operating system may be installed in the information handling system 300, e.g., on the disk drive 312 or in the memory 304. The memory 304 and the disk drive 312 may be operated by the processor 302. Optionally, the information handling system 300 also includes a communication device 310 for establishing one or more communication links (not shown) with one or more other computing devices such as servers, personal computers, terminals, tablets, phones, watches, IoT devices, or other wireless or handheld computing devices. The communication device 310 may include one or more of: a modem, a Network Interface Card (NIC), an integrated network interface, a NFC transceiver, a ZigBee transceiver, a Wi-Fi transceiver, a Bluetooth® transceiver, a radio frequency transceiver, an optical port, an infrared port, a USB connection, or other wired or wireless communication interfaces. Transceiver may be implemented by one or more devices (integrated transmitter(s) and receiver(s), separate transmitter(s) and receiver(s), etc.). The communication link(s) may be wired or wireless for communicating commands, instructions, information and/or data. In one example, the processor 302, the memory 304, and optionally the input device(s) 306, the output device(s) 308, the communication device(s) 310 and the disk drive(s) 312 are connected with each other through a bus, a Peripheral Component Interconnect (PCI) such as PCI Express, a Universal Serial Bus (USB), an optical bus, or other like bus structure. In one embodiment, at least some of these components may be connected through a network such as the Internet or a cloud computing network. A person skilled in the art would appreciate that the information handling system shown in FIG. 3 is an example only and that the information handling system 300 can in other embodiments have different configurations (e.g., include additional components, has fewer components, etc.).

Figure 4:
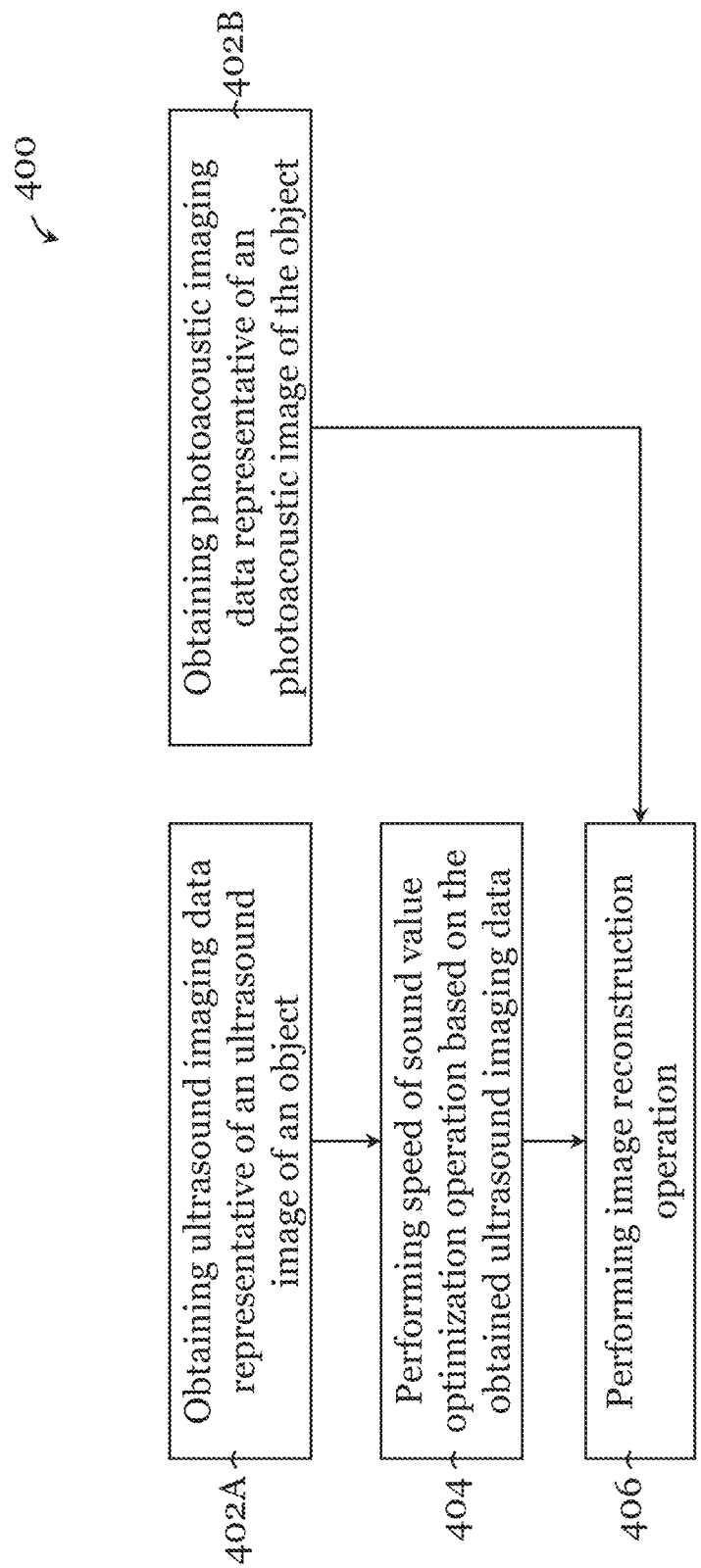
FIG. 4 is a flowchart illustrating a method for processing photoacoustic and ultrasound imaging data in one embodiment.

FIG. 4 illustrates a method 400 for processing photoacoustic and ultrasound imaging data in one embodiment.

Method 400 includes step 402A, in which ultrasound imaging data representative of an ultrasound image of an object is obtained. In one example, the ultrasound imaging data may be obtained directly from the imaging system, optionally as soon as the ultrasound imaging data is acquired, to enable substantially real time image data processing. In another example, the ultrasound imaging data may be retrieved from memory. Method 400 also includes step 402B, in which photoacoustic imaging data representative of an ultrasound image of an object is obtained. In one example, the photoacoustic imaging data may be obtained directly from the imaging system, optionally as soon as the photoacoustic imaging data is acquired, to enable substantially real time image data processing. In another example, the photoacoustic imaging data may be retrieved from memory. The obtaining of the photoacoustic imaging data in step 402B and the obtaining of the ultrasound imaging data in step 402A may be performed at any order (including simultaneously). In one example, the ultrasound imaging data and the photoacoustic imaging data obtained are complementary and they represent co-registered ultrasound image and photoacoustic image of the object (of the same imaging plane). In one example, the ultrasound imaging data and the photoacoustic imaging data obtained need to be further processed to become complementary and co-registered.

After step 402A, the method 400 proceeds to step 404, in which a speed of sound value optimization operation based on the obtained ultrasound imaging data. The speed of sound value optimization operation is arranged to determine one, two, or more speed of sound values for facilitating reconstruction of the ultrasound image and photoacoustic image. In some examples, the method 400 enables selection between different speed of sound value optimization operations for processing different data/images, e.g., based on user input or data characteristics. As mentioned, the speed of sound value(s) is an important reconstruction parameter for achieving optimal resolution and/or contrast in ultrasound and photoacoustic images.

In some embodiments, the speed of sound value optimization operation is arranged to determine a single speed of sound value for use in reconstruction of the ultrasound image and the photoacoustic image. In one example, only the ultrasound imaging data associated with a predetermined region of interest is processed in the determination of the speed of sound value.

In one example, to determine the optimal (single) speed of sound value, the method involves processing the same set of ultrasound imaging data multiple times, sequentially or simultaneously, each time using a respective predetermined speed of sound value, to determine different total coherence factor values each associated with the processing using a respective speed of sound value. In one example, the determination of the total coherence factor values may involve processing the same set of ultrasound imaging data multiple times, sequentially or simultaneously, each time using a respective predetermined speed of sound value, to determine different coherence factor maps each associated with the processing using a respective speed of sound value. Then, a respective total coherence factor value for each respective coherence factor map can be determined based on a sum of the coherence factor values (e.g., magnitudes) of the corresponding coherence factor map. The method further involves, after the total coherence factor values are determined, determining the optimal speed of sound value based on the different total coherence factor values. In one example, the speed of sound value corresponding to the largest total coherence factor value can be determined as the optimal speed of sound value. In another example, a total coherence factor value function is determined based on the different total coherence factor values and a speed of sound value corresponding to an extreme (maximum or minimum, depending on sign convention) value of the total coherence factor value function is determined as the optimal speed of sound value. The total coherence factor value function can be generated by interpolation (e.g., linear, spline, polynomial, etc.). In one example the extreme value can be determined by determining a derivative of the total coherence factor value function.

In some embodiments, the speed of sound value optimization operation is arranged to determine two speed of sound values for use in reconstruction of the ultrasound image and the photoacoustic image. In one example, only the ultrasound imaging data associated with a predetermined region of interest is processed in the determination of the speed of sound values.

In one example, the speed of sound value optimization operation (for two speed of sound values) may include first performing a segmentation operation on the ultrasound imaging data. The segmentation operation may include identifying a boundary between two sections of the ultrasound image. The boundary may be a boundary between the object and a coupling medium (e.g., liquid) arranged between the object and the transducer elements during imaging, a boundary between different sections or parts of the object imaged, etc. The boundary may be endless, straight, curved, etc. The boundary identification may include determining a map based on ultrasound signals received by each respective transducer element (as a result of ultrasound waves detected at the transducer element) in response to the transmission of ultrasound waves by the transducer element towards the object, and then using the map to determine the boundary. In one example, the map can be processed to determine first arrival positions of the ultrasound waves/signals, which indicate presence of boundary. Example methods for determine the first arrival positions include time-of-flight picker algorithm, e.g., an improved Akaike information criterion picker algorithm. The coordinates of the boundary with respect to the image may be determined by performing coordinate transform operation. As a result the ultrasound imaging data will be divided into two subsets each associated with a respective section (e.g., one subset associated with the object, another subset associated with the coupling medium). Each of the two subsets of data will be processed separately to determine respective optimal speed of sound values for use in image reconstruction. In one example, the subset of ultrasound imaging data is processed to determine an optimal speed of sound value associated with the corresponding section. This may apply to one or both subsets. In one example, the optimal speed of sound value associated with the corresponding section can be determined based on a temperature or an average temperature of the corresponding section at the time the ultrasound imaging data is acquired. This may apply to one or both subsets. A lookup table that maps different temperatures with different speed of sound values can be used to facilitate the determination.

In one example, the processing of a subset of the ultrasound imaging data associated with one of the sections may be processed to determine an optimal speed of sound value associated with the corresponding section may involve: processing the same subset of ultrasound imaging data multiple times, sequentially or simultaneously, each time using a respective predetermined speed of sound value, to determine different total coherence factor values each associated with the processing using a respective speed of sound value. In one example, the determination of the total coherence factor values may involve processing the same subset of ultrasound imaging data multiple times, sequentially or simultaneously, each time using a respective predetermined speed of sound value, to determine different time of flight maps each associated with the processing using a respective speed of sound value. The time of flight maps may be determined based on multi-stencil fast marching method. Then, the time of flight maps are each processed to determine a respective ultrasound image. In turn, the ultrasound images are each processed to determine determining a total coherence factor value based on a sum of coherence factor values of the coherence factor map associated with the respective ultrasound image. The method further involves, after the total coherence factor values are determined, determining the optimal speed of sound value for the subset based on the different total coherence factor values. In one example, the speed of sound value corresponding to the largest total coherence factor value can be determined as the optimal speed of sound value for the subset. In another example, a total coherence factor value function is determined based on the different total coherence factor values, and a speed of sound value corresponding to an extreme (maximum or minimum, depending on sign convention) value of the total coherence factor value function is determined as the optimal speed of sound value for the subset. The total coherence factor value function can be generated by interpolation (e.g., linear, spline, polynomial, etc.). In one example the extreme value can be determined by determining a derivative of the total coherence factor value function. The determination of the extreme value (maximum or minimum value, depending on sign convention) can be limited to the extreme portion of the total coherence factor value function. For example, the determination of the extreme value may be performed using a golden section search algorithm.

After the speed of sound value optimization operation in step 404, the method 400 proceeds to step 406, to perform image reconstruction operation. The image reconstruction operation includes reconstructing ultrasound image and photoacoustic image based on the determined speed of sound value(s) using the ultrasound imaging data and photoacoustic imaging data. The reconstruction of the ultrasound image and the reconstruction of the photoacoustic image can be performed separately or simultaneously.

In one example in which the speed of sound value optimization operation determines a single optimal speed of sound value, the ultrasound imaging data, or the part of it associated with a region of interest, can be processed based on the determined optimal speed of sound value to reconstruct an ultrasound image of the object; and the photoacoustic imaging data, or the part of it associated with a region of interest, can be processed based on the determined optimal speed of sound value to reconstruct a photoacoustic image of the object. In the reconstruction, a delay-and-sum beamforming method, or its variant, can be used to process the ultrasound imaging data and/or the photoacoustic imaging data based on the determined optimal speed of sound value. Optionally, prior to image reconstruction, the ultrasound imaging data and/or the photoacoustic imaging data may be pre-processed, e.g., filtered.

In one example in which the speed of sound value optimization operation determines a two optimal speed of sound values (for different regions/sections), each subset of the ultrasound imaging data, or the part of it associated with a region of interest, can be processed based on the corresponding determined optimal speed of sound value to reconstruct the corresponding part of the ultrasound image of the object; and each corresponding subset of the photoacoustic imaging data, or the part of it associated with a region of interest, can be processed based on the corresponding determined optimal speed of sound value to reconstruct the corresponding part of the photoacoustic image of the object. In the reconstruction, for each subset or section, a delay-and-sum beamforming method, or its variant, can be used to process the ultrasound imaging data and/or the photoacoustic imaging data based on the respective determined optimal speed of sound value. Optionally, prior to image reconstruction, the ultrasound imaging data and/or the photoacoustic imaging data may be pre-processed, e.g., filtered.

After the photoacoustic and ultrasound images are reconstructed (optionally pre-processed and/or post-processed), they are presented on a display for view and optionally manipulation by an operator of the data processing system. The photoacoustic and ultrasound images can be displayed separately, at the same time or one at a time, or displayed in an overlaid manner (optionally with color representation).

The following description provides specific examples on the implementation of the systems 100, 200 and method 400 of the invention. It should be appreciated that these embodiments are presented to facilitate understanding of one or more aspects of the invention and that the invention is not limited to these specific examples (and their application(s) and advantage(s)).

Example 1

The inventors of the invention have devised, through research, experiments, and/or trials, that full-ring (transducers arranged in a ring-shaped array) dual-modal ultrasound and photoacoustic imaging can provide complementary contrasts, high spatial resolution, full view angle, and/or deep penetration, and are suitable for pre-clinical and clinical applications. The inventors of the present invention have realized that high-quality video-rate dual-modal imaging and imaging processing may be difficult in these systems because the intensive data acquisition results in data processing burden and the object-dependent speed of sound variation could affect image quality during reconstruction.

The inventors of the invention have devised, in this example, systems and methods associated with full-ring ultrasound and photoacoustic computed tomography with real-time optimization of the speed of sound value used for imaging processing/reconstruction. The inventors of the invention have devised, in this example, a speed of sound optimization method that enables real-time, e.g., video-rate, speed of sound compensation in dual-modal ultrasound and photoacoustic imaging as well as ultrasound and photoacoustic computed tomography.

Figure 5:
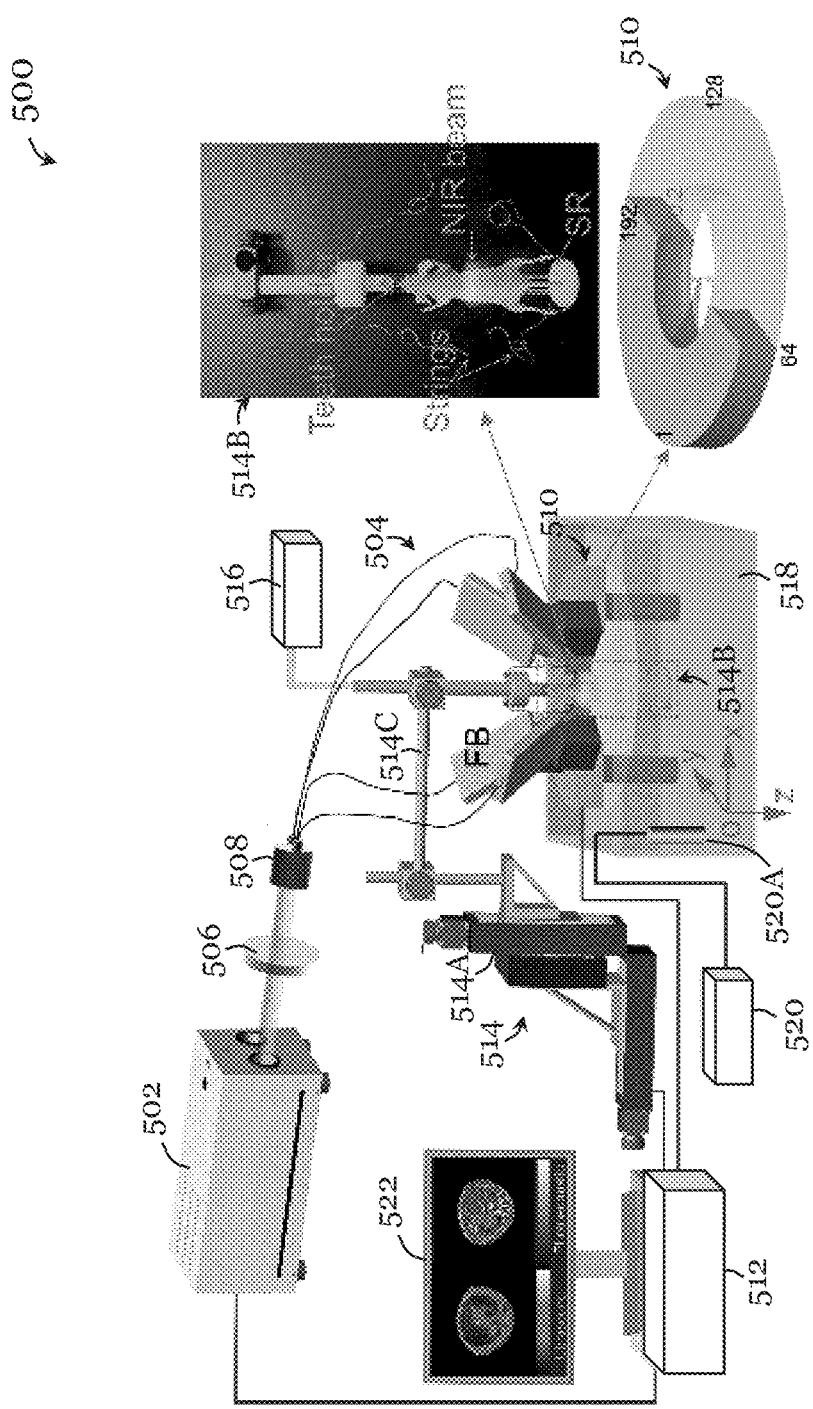
FIG. 5 is a schematic diagram of an experiment setup of an imaging system in one embodiment, with a close up view of the animal holder portion and an illustration of the transducer array.

FIG. 5 shows an experiment setup of an imaging system 500 in this example.

The imaging system 500 includes an irradiation unit with a laser module arranged to irradiate an object to be imaged with the laser radiation, to facilitate photoacoustic excitation. The laser module includes a laser source 502, a laser fiber unit 504, a filter 506 arranged in the path of the laser emission path of the laser source 502 for filtering the laser radiation emitted by the laser source 502, and a coupler 508 arranged to optically couple the laser radiation emitted by the laser source 502 into the laser fiber unit 504. In this example, the laser source 502 is Q-switched Nd: YAG laser (Spectra-Physics, Santa Clara, CA, USA) that can provide nanosecond laser pulses (e.g., 5 ns to 8 ns laser pulses) at 20 Hz. The laser source 502 can selectively or simultaneously provide two laser wavelengths of 532 nm and 1064 nm. The laser fiber unit 504 includes four optical fiber bundles arranged to be distributed, angularly, around a holder that holds the object (an animal in this example) during imaging. Each of the optical fiber bundles are arranged in a substantially cuboidal housing. A lower or distal end of each housing or optical fiber bundle includes a 32 mm×1 mm rectangular window. The lower or distal end is oriented at 60° relative to an imaging plane (of the object). In this setup, the optical fiber bundles of the laser fiber unit 504 are fixed and mounted near (above) the ultrasound transducer unit 510.

The imaging system 500 also includes a transducer unit 510. The transducer unit 510 includes multiple transducer elements controlled and operable to selectively transmit and receive ultrasound. The transducer unit 510, or each transducer element, is operable to (i) detect ultrasound waves generated by the object in response to the laser module irradiating the object with the laser radiation, and generate electric signals that form photoacoustic imaging data based on the detected ultrasound waves, and (ii) transmit ultrasound waves towards the object and, in response, detect ultrasound waves reflected, scattered, and/or transmitted by the object, for facilitating ultrasound imaging, and generate electric signals that form ultrasound imaging data based on the detected ultrasound waves. In this setup the transducer unit 510 includes 256 transducer elements, angularly spaced apart and arranged in a ring-shaped array, to facilitate full-view in-plane acoustic (e.g., ultrasound) detection. Each of the transducer elements is 14 mm×0.88 mm, has a radius of 40 mm, and is cylindrically focused in the elevational direction with an acoustic numerical aperture (NA) of 0.2. Each transducer element of the transducer unit 510 has a central frequency of 6.25 MHz and a two-way (transmit and receive) bandwidth of 58.4% and a one-way (receive) bandwidth of 76.8%.

The imaging system 500 also includes a control unit. The control unit includes a data acquisition unit 512. In this example, the data acquisition unit 512 is Vantage 256 data acquisition unit (Verasonics Inc.). The data acquisition unit 512 includes 256 channels, each connected and mapped to a respective one of the transducer element in the transducer unit 510 to facilitate high-speed dual-modal imaging. Each of the channels has an independent amplifier with a tunable gain of up to 54 dB. The data acquisition unit 512 is operable to sample the ultrasound and photoacoustic signals at 25 MHz and 14 bits resolution. The control unit controls the transducer elements in the transducer unit 510 to operate as ultrasound transmitter and ultrasound receiver selectively and can electrically disconnect or turn off the transducer elements.

The control unit is further operably connected with the laser source 502 for synchronization of operation. The control unit may receive a laser trigger signal and, in response, controls the transducer elements to operate as ultrasound receivers to receive broadband ultrasound generated by the object in response to the laser module irradiating the object with the laser radiation. In one example, the control unit may control operation or activation of the laser source 502.

The imaging system 500 also includes a motorized object holder assembly 514 arranged to hold or support an object to be or being imaged. The motorized object holder assembly 514 includes a motorized control device 514A, an object (animal) holder 514B, and a frame 514C drivingly coupling the animal holder 514B with the motorized control device 514A. The motorized control device 514A is arranged to move the animal holder 514B linearly, up and down, via the frame 514C, to move the animal held (e.g., vertically held) by the holder with reference of the transducer unit 510 for imaging different sections of the animal. The motorized control device 514A may include a stepper motor. The animal holder 514B is a 3D-printed animal holder for trunk imaging. The enlarged view of the animal holder 514B shows that the holder includes a middle frame portion, a bottom support plate (SR) mounted to the bottom of the frame rod and includes a hole that allows a tail of an animal to pass through, strings for securing the animal's paws/limbs to the holder 514B, a teeth holder for supporting the teeth of the animal, and a top hollow tube mounted to the top of the frame rod and through which anesthesia can be provided to the animal to sedate it during imaging. The hollow tube also includes a clamp for fixing the animal's nose and/or mouth. The length of the middle frame portion is adjustable (e.g., telescopic rod) to accommodate animals of different sizes. The enlarged view of the animal holder 514B also shows an example position of the near infrared laser beam (NIR beam) provided by the laser module. An anesthesia unit with an anesthesia source 516 may be fluidly coupled with the frame 514C and the animal holder 514B to deliver suitable dosage of anesthesia to the animal during imaging (to reduce movement) when the animal is held by the holder 514B. The motorized control device 514A, hence the movement of the holder 514B, may be controlled by the control unit 512. The motorized control device 514A, hence the movement of the to holder 514B, may provide movement signals to the control unit for synchronization of operation of the system 500.

The imaging system 500 also includes a container 518 for containing coupling medium in which the object to be or being imaged is partly immersed. In one example, the container 518 contains a coupling fluid/liquid, which, during imaging, is to be arranged between the object (the part of it) to be or being imaged and the transducer elements of the transducer unit 510. To image different sections of the object, the animal holder 514B can be moved up and down relative to the transducer unit 510. A temperature sensor 520 with a thermocouple 520A immersed in the coupling fluid may be used to detect or monitor temperature of the coupling medium during imaging.

A data processing system 522 for processing imaging data obtained from the imaging system 500 may be provided. The data processing system 522 may be in data communication with the control unit or the data acquisition unit 512 to receive the ultrasound imaging and photoacoustic imaging data. In this embodiment, the data processing system 522 may be considered as part of the imaging system 500. The data processing system 522 may be used to implement, at least partly, the methods in this example.

Figure 6:
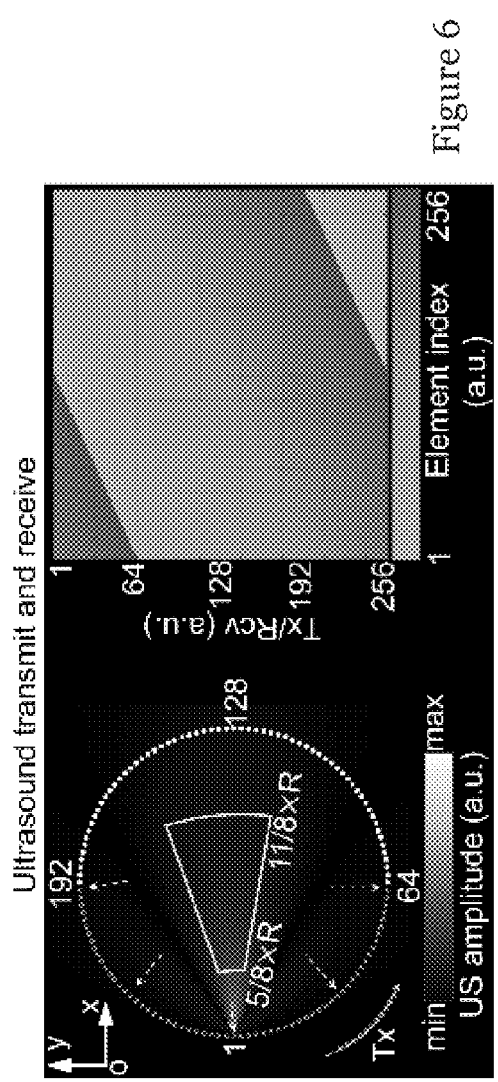
FIG. 6 is an illustration of an ultrasound imaging transmit and receive sequence in one embodiment for use in the imaging system of FIG. 5.
Figure 7:
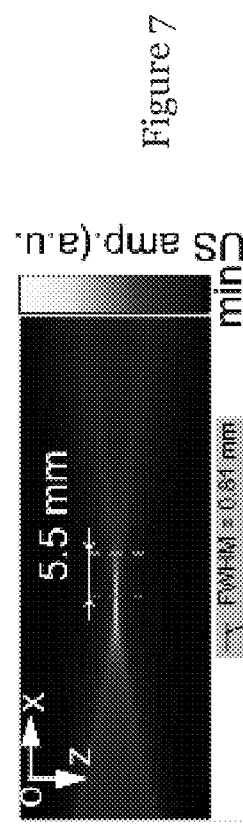
FIG. 7 is an illustration of a simulated acoustic field in the x-z plane for the ultrasound imaging transmit and receive sequence of FIG. 6.
Figure 8:
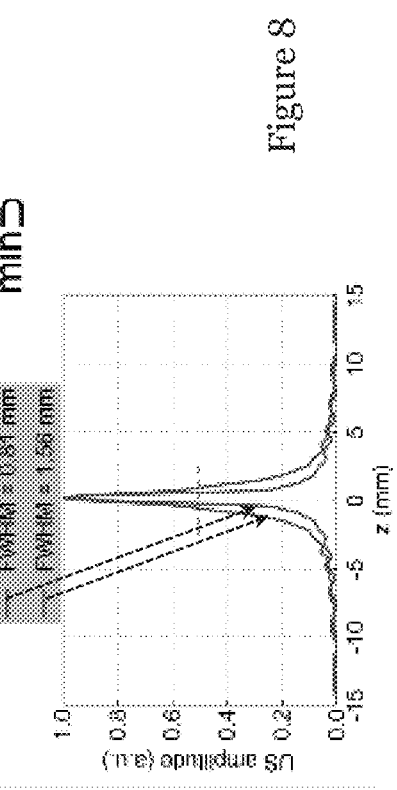
FIG. 8 is a graph of line profiles at the center and off-center from 5.5 mm of the acoustic field of FIG. 7.

FIG. 6 shows an example ultrasound imaging transmit and receive sequence for use in the imaging system 500. This sequence is based on sequential active excitation (ultrasound transmission) of each transducer element and corresponding parallel detection (ultrasound detection) by half of the transducer elements. FIG. 6 also shows an acoustic simulation at the 1$^{st}$ position (transducer element 1), with fan-shaped region defined by the white solid line defining the reconstruction region at one transmission event. The skilled person understands that the fan-shaped region for different transmitters (different transducer elements as transmitter) will be different. In one example, to perform ultrasound imaging, a synthetic transmit aperture (STA) approach is used to collect the ultrasound signals. The transducer elements in the ring-array are sequentially excited with a 1-cycle sinusoidal pulse to transmit ultrasound waves, at a 250 µs interval between every transmission. For each respective excitation/transmission, back-scattered ultrasound signals are detected by 128 transducer elements substantially simultaneously (with little or no time delay). For each respective excitation/transmission, the respective 128 transducer elements (including the emitting element) as receivers are on the same side as the emitting element, and the respective remaining 128 transducer elements are electronically switched off to reduce interference. FIG. 7 shows a simulated acoustic field in the x-z plane for the transmission event in FIG. 6. FIG. 8 shows line profiles at the center and off-center from 5.5 mm of the acoustic field of FIG. 7.

Figure 9:
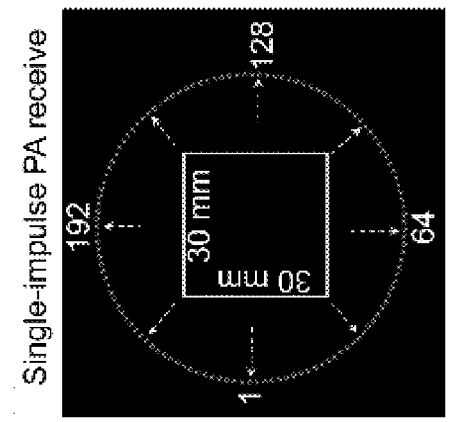
FIG. 9 is an illustration of photoacoustic imaging ultrasound receive sequence in one embodiment for use in the imaging system of FIG. 5.

FIG. 9 shows an example photoacoustic imaging ultrasound receive sequence for use in the imaging system 500. In one example, to perform photoacoustic imaging, a 1064 nm laser pulse is irradiated on the object and all 256 transducer elements operate as detectors after each laser pulse, e.g., in ~50 is after each laser pulse. As mentioned, the laser trigger is used to synchronize the control unit and hence the operation of the transducer unit. FIG. 9 also show a square region (mm×mm) defined by the white solid line defining the reconstruction region at one/each transmission event. The skilled person understands that the square region for different transmitters (different transducer elements as transmitter) will be different.

Figure 10:
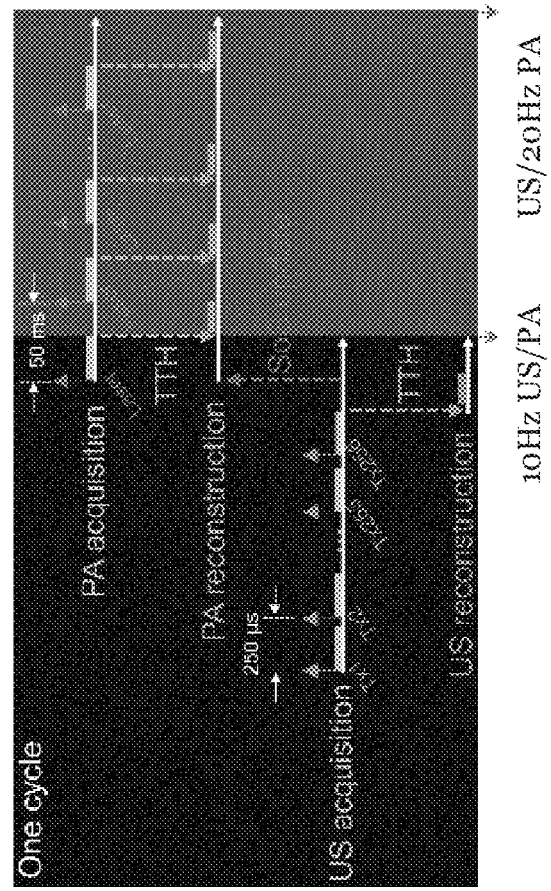
FIG. 10 is an illustration of timing sequence for ultrasound and photoacoustic imaging, image reconstruction, speed of sound determination, and laser trigger in one embodiment, with two imaging modes shown: (1) 10 Hz ultrasound and photoacoustic imaging (video-rate) and (2) single-shot ultrasound and 20 Hz photoacoustic imaging.

FIG. 10 shows a timing sequence for dual-modal ultrasound and photoacoustic imaging, image reconstruction, speed of sound determination, and laser trigger using the system 500 in one embodiment. As shown in FIG. 10, the dual-modal imaging speed may depend on one or more of: the time interval between ultrasound excitations/transmission (250 µs×255), the Q-switched delay (200 µs), the photoacoustic acquisition time (50 µs), and the laser pulse repetition rate (20 Hz). In this example, the system 500 can alternate between ultrasound and photoacoustic imaging up to 10 Hz.

FIG. 10 shows two imaging modes. The first mode is a 10 Hz ultrasound and photoacoustic imaging (video-rate) mode. In this mode, in each cycle or period, one round of ultrasound imaging is first performed (each transducer acts as transmitter once) following by one round of photoacoustic imaging (transmit one laser pulse). In this mode, the after the ultrasound imaging is performed, the obtained ultrasound imaging data can be used to perform a speed of sound value optimization operation to determine an optimal speed of sound value for use in reconstruction of the ultrasound and photoacoustic images. The second mode is a single-shot ultrasound imaging and 20 Hz photoacoustic imaging mode. In this mode, in each cycle or period, one round of ultrasound imaging is first performed (each transducer acts as transmitter once) following by multiple rounds of photoacoustic imaging (consecutively transmit multiple laser pulses). The multiple rounds of photoacoustic imaging is performed at a rate of 20 Hz.

The inventors of the invention have realized that compensation for the heterogeneous and time-variant speed of sound (SoS), while can improve the ultrasound and photoacoustic image quality following reconstruction, may significantly increase the computation time and/or computation resource requirement. The inventors of the invention have also realized that such compensation often requires manual input/operator intervention.

In this example, a speed of sound value optimization operation that involves computing and compensating for the average speed of sound in the field of view is provided. This approach may enable real-time reconstruction of quality ultrasound and photoacoustic images at a video rate.

In this example, the optimal speed of sound (to be used in image reconstruction) is adaptively computed using the coherence factor (CF) of the ultrasound signals. The coherence factor is defined as the ratio between the total coherent energy and the total incoherent energy and it increases when the phase aberration is shrinking. An accurate speed of sound can minimize the phase aberration in image reconstruction. In this example, the optimal speed of sound is determined via searching the maximum coherence factor value of the ultrasound image. The coherence factor value $CF_{v_i}(n)$ can be determined from $$CF_{v_i}(n) = \frac{\left|\sum_{Rcv=1}^{N_{elm}} \sum_{Tx=1}^{N_{elm}} I(n)\right|^2}{N_{elm} \times \sum_{Rcv=1}^{N_{elm}} \left|\sum_{Tx=1}^{N_{elm}} I(n)\right|^2} \qquad (1)$$

where n represents the reconstructed pixel position, $v_i$ is an estimated speed of sound, Tx and Rcv are the transmitting and receiving transducer elements, $N_{elm}$ is the number of transducer elements, I(n) is the delayed channel data according to the $v_i$ and the distance of flight (DoF).

To find the optimal speed of sound value, a series of coherence factor maps can be obtained and their coherence factor summation (CFS) values can be calculated at different predetermined speed of sound. Interpolation such as spline interpolation can then be applied to generate, based on the coherence factor summation values, a coherence factor summation value function or curve to localize the optimal speed of sound. The optimal speed of sound can be determined from $$S\hat{o}S = \arg\max_{SoS} f(CFS) \qquad (2)$$

where $f$ is the interpolation operator.

Considering the directivity of the ultrasound transducer elements, the reconstruction is limited or reduced to a fan shaped region (FIG. 6). To accelerate the computation, a look-up table of the distance of flight can be predetermined and stored in the memory. The distance of flight look-up table ($N_y \times N_x \times N_{elm}$) includes a 3D matrix that defines the distance between each reconstructed pixel to each receiving transducer element (transducer element that acts as receiver for the corresponding acquisition). $N_y \times N_x$ is the image size.

After determining the optimal speed of sound value, the ultrasound and photoacoustic images can be reconstructed using a weight-based delay-and-sum method as disclosed in Y. Zhang, Y. Wang, P. Lai, and L. Wang, "*Video-rate Dual-modal Wide-beam Harmonic Ultrasound and Photoacoustic Computed Tomography,*" *IEEE Trans. Med. Imaging*, 2021. The raw ultrasound and photoacoustic imaging data can be preprocessed using a $3^{rd}$-order digital Butterworth bandpass filter (0.05-8.5 MHz). For the photoacoustic image reconstruction, the reconstruction region or image size is 30 mm×30 mm (FIG. 9), and the raw data are truncated by half. Within this region, the resolution is better than 380 μm. In addition, the confined reconstruction region reduces the computational burden and facilitates real-time imaging.

After reconstruction, the ultrasound image is further processed using envelope detection, logarithmic compression, and median filter, based on the teachings in Y. Zhang and L. Wang, "*Video-Rate Ring Array Ultrasound and Photoacoustic Tomography,*" IEEE Trans. Med. Imaging, vol. 39, no. 12, pp. 4369-4375, December 2020. For the photoacoustic image, a nonlocal means filter based on the teachings in Siregar, R. Nagaoka, I. Ul Haq, and Y. Saijo, "*Non local means denoising in photoacoustic imaging,*" Jpn. J. Appl. Phys., vol. 57, no. 7, p. 07LB06, July 2018, contrast-limited adaptive histogram equalization (CLAHE), and a vessel filter algorithm based on the teachings in E. Merčep, J. L. Herraiz, X. L. Deán-Ben, and D. Razansky, "*Transmission-reflection optoacoustic ultrasound (TROPUS) computed tomography of small animals,*" Light. Sci. Appl., vol. 8, no. 1, pp. 2047-7538, December 2019 are applied to further process the photoacoustic image. To enhance the visibility, a snake-based active contour algorithm based on the teachings in K. Basak, X. Luís Deán-Ben, S. Gottschalk, M. Reiss, and D. Razansky, "*Non-invasive determination of murine placental and foetal functional parameters with multispectral optoacoustic tomography,*" Light Sci. Appl. 2019 81, vol. 8, no. 1, pp. 1-10, August 2019 is applied to segment the region of interest. To maintain fidelity, the quantified parameters are determined from the reconstructed images without contrast enhancement. The above data processing steps are implemented in MATLAB (2019b, MathWorks, USA) program on a computer (Inter Core i7@2.60 GHz, 16 GB of RAM, NVIDIA GeForce RTX 2060).

Simulations are performed on the ultrasound and photoacoustic imaging with tspeed of sound optimization operation of this example. In particular, simulations are performed using the k-Wave toolbox to show how the speed of sound values are calculated, using two different numerical phantoms, a simple numerical phantom illustrated in FIG. 14 and a to numerical breast phantom illustrated in FIG. 17. In the simulation, the coupling medium between the phantom and the transducer element is water with a speed of sound of 1500 m/s and a density of moo kg/m$^3$. For the simple numerical phantom, to generate acoustic heterogeneity, random Gaussian noises are added to the acoustic impedances in the hypoechoic region of the simple numerical phantom. The average speed of sound is 1538 m/s and the standard deviation is 39.4 m/s. The maximal acoustic impedance is 1.7 MRayl. For the numerical breast phantom, it is modified from a clinical magnetic resonance angiography (MRA) breast data set. Anatomical structures including fibroglandular, fat, and skin can be visualized. The acoustic impedances is modified from 1.5 MRayl to 1.7 MRayl. For photoacoustic imaging simulation, numerical vessel structures are added to both phantoms. For ultrasound imaging simulation, a 1-cycle sinusoidal pulse is sequentially transmitted from each respective transducer elements. The pulse is modulated with the Hanning window before being sent to the transducer element. Respective 128 contiguous transducer elements simultaneously receive echoes after each transmission. In the photoacoustic imaging simulation, the blood vessels are assigned an initial pressure, and all 256 transducer elements receive the signals. The sampling frequency is set to 53.2566 MHz for both ultrasound and photoacoustic imaging. The total running steps are 3600 for ultrasound imaging simulation and 1800 for photoacoustic imaging simulation. The computational grid consists of 1200×1200 pixels including a perfectly-matched layer (damping block). The pixel size is 100 μm on each side. A frequency-dependent acoustic attenuation ($\alpha=0.75f^{1.5}$) is added in the simulation. The simulations are performed using a graphics processing unit (GPU).

FIGS. 11 to 19 illustrate the simulation result.

Figures 11, 12, 13:
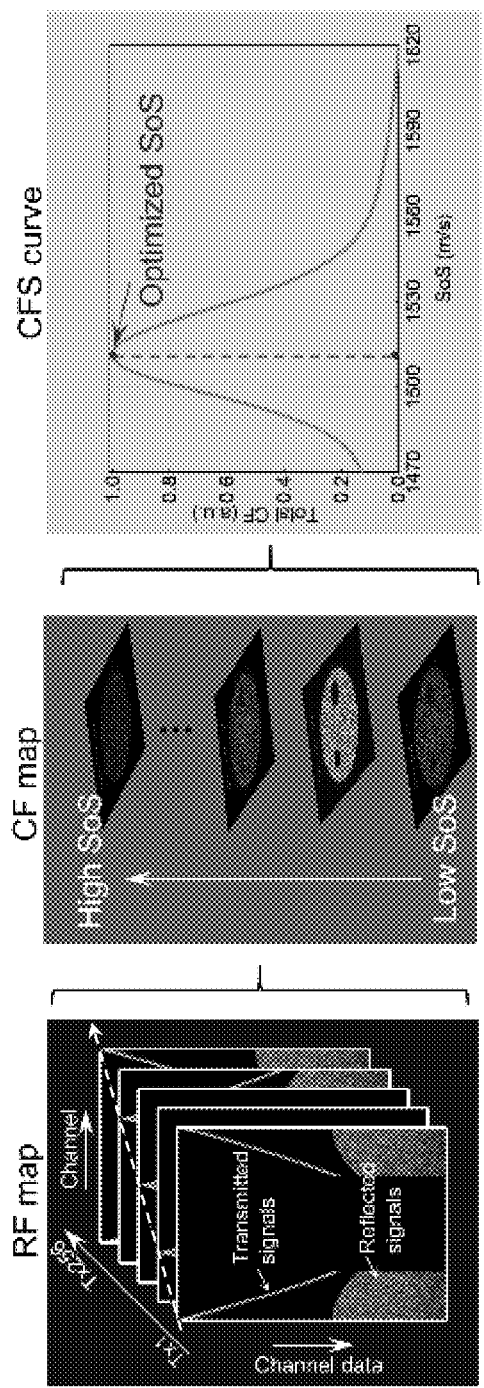
FIG. 11 is an illustration of transducer channel data maps (RF maps) obtained from a simulation on ultrasound and photoacoustic imaging with speed of sound value optimization in one embodiment.
FIG. 12 is an illustration of pixel-based coherence factor maps (CF maps) each calculated using a respective speed of sound value in the simulation on ultrasound and photoacoustic imaging with speed of sound value optimization in one embodiment.
FIG. 13 is a graph showing a plot of the total coherence factor, or coherence factor summation (CFS) value, for different speed of sound values in the simulation on ultrasound and photoacoustic imaging with speed of sound value optimization in one embodiment.

FIGS. 11 to 13 illustrate how the optimal speed of sound is determined in this simulation example.

FIG. 11 shows the transducer received channel data maps (RF maps) obtained from ultrasound imaging simulation. As shown in Figure ii, the transmitted and reflected signals can be identified. The transducer element is sequentially excited along the dashed arrow. As 128 elements on the opposite side of the transmitter transducer element are switched off while the 128 transducer elements on the same side as the transmitter transducer element are operated to receive ultrasound signals, only directly transmitted and phantom-reflected signals can be seen in FIG. 11.

FIG. 12 shows the pixel-based coherence factor maps each calculated using a respective predetermined speed of sound value (e.g., from low to high). Since only one speed of sound value is used for each map, the speed of sound value can also be referred to as an average speed of sound value.

FIG. 13 shows a graph of the total coherence factor, or coherence factor summation (CFS) value, for different speed of sound values in the simulation. The total coherence factors or coherence factor summation values can be determined from the coherence factor maps as mentioned above. The total coherence factors or coherence factor summation values can be interpolated to create the coherence factor summation curve, as mentioned above. The coherence factor summation curve has a peak. The speed of sound value that corresponds to the peak is the optical speed of sound value.

FIGS. 14 to 16 illustrate the simulation (including reconstruction) results for the simple numerical phantom. FIG. 14 shows the simple numerical phantom (ground truth "GT") which contains two anechoic regions with different diameters and other details described above. FIG. 15A illustrates overlaid ultrasound and photoacoustic images of the simple numerical phantom reconstructed with a wrong or suboptimal speed of sound value whereas FIG. 15B illustrates overlaid ultrasound and photoacoustic images of the simple numerical phantom reconstructed with an optimal speed of sound value determined based on coherence factor summation value curve above. FIG. 16 shows the diameters of the anechoic regions reconstructed with the wrong speed of sound value ("wrong") and optimized speed of sound value ("adaptive") respectively.

FIGS. 17 to 19 illustrate the simulation (including reconstruction) results for the numerical breast phantom. FIG. 17 shows the numerical breast phantom (ground truth "GT") with details described above (FG refers to fibroglandular). FIG. 18A illustrates overlaid ultrasound and photoacoustic images of the numerical breast phantom reconstructed with a wrong or suboptimal speed of sound value whereas FIG. 18B illustrates overlaid ultrasound and photoacoustic images of the numerical breast phantom reconstructed with an optimal speed of sound value determined based on coherence factor summation value curve above. FIG. 19 are zoom in views of the white boxes in FIGS. 18A and 18B respectively.

Generally, a predetermined speed of sound value, in particular one that chosen manually, may be suboptimal for use in image reconstruction due to variations in anatomical structures, sizes, physiological statuses of the object, and temperature. Using a suboptimal speed of sound value for image reconstruction may cause image distortion or blurred boundaries. See for example FIGS. 15A and 18A, which show distorted and split photoacoustic imaging features. An optimized speed of sound value, such as one determined using the method in this example, can effectively reduce these distortions. See for example FIGS. 15B and 18B. FIG. 16 further shows that the diameters of the two anechoic regions in the numerical phantom are properly corrected with the adaptive (optimized) speed of sound value determined using the method in this example. FIG. 19 further shows that some anatomical structures, such as the fibroglandular (FG) and fat, can be distinguished more clearly using the adaptive (optimized) speed of sound value determined using the method in this example.

Figures 22, 23A, 23B:
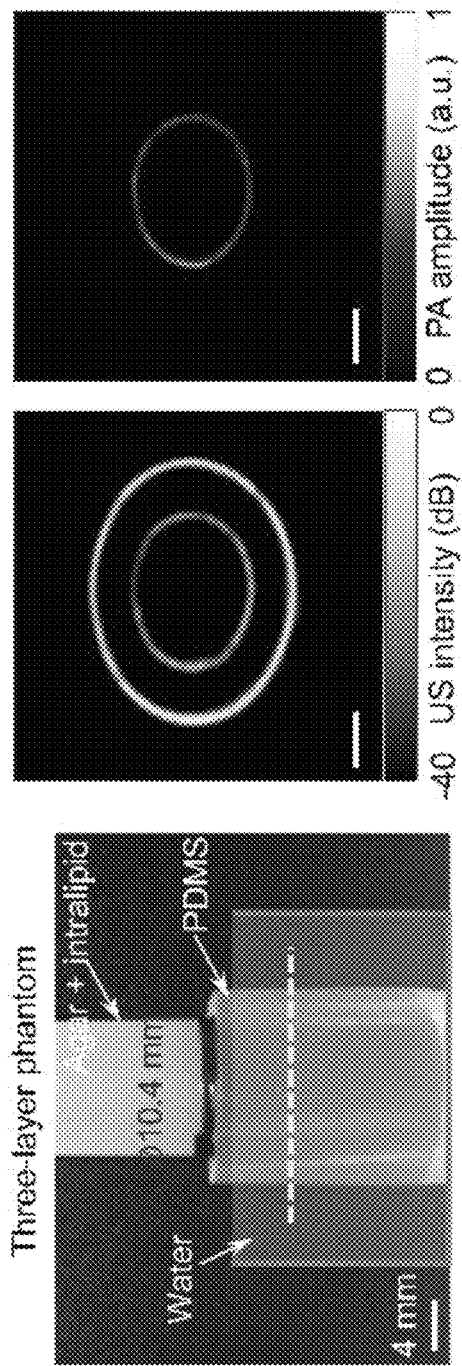
FIG. 22 is a photograph of a three-layer coupling media phantom imaged by the imaging system of FIG. 5.
FIG. 23A is an illustration of an ultrasound image of the three-layer coupling media phantom imaged by the imaging system of FIG. 5, reconstructed using an optimized (adaptive) speed of sound value.
FIG. 23B is an illustration of a photoacoustic image of the three-layer coupling media phantom imaged by the imaging system of FIG. 5, reconstructed using the optimized (adaptive) speed of sound value.

Performance characterizations are performed on the imaging system 500. In this example, to characterize the system, axial, tangential, and elevational resolutions are characterized (FIGS. 7, 8, and 20A-21B). To determine the reconstructed region with acceptable spatial resolution, the spatial resolution is measured by imaging a 20 μm diameter tungsten wire at different positions. Further, to validate the accuracy of ultrasound and photoacoustic reconstruction using the adaptive speed of sound value, a three-layer phantom (FIG. 22) is fabricated. As shown in FIG. 22, for the three-layer phantom, the innermost portion/layer is a cylinder with a diameter of 10.4 mm and made of agar-water gel (6% w/w) with 0.9% (v/v) intralipid, the middle portion/layer is thin (<0.1 mm) black tape, and the outermost portion/layer is a hollow cylinder with a diameter of 15 mm and made of tissue-mimic polydimethylsiloxane (PDMS). Because of the acoustic heterogeneity, the multi-layer/portion phantom and the surrounding water have an impedance mismatch.

FIGS. 20A to 23B illustrate the performance characterizations result.

FIG. 20A shows imaging result of ultrasound imaging of the tungsten wire with 20 μm diameter, acquired with the tungsten wire located at different positions, using the imaging system 500. FIG. 20B shows imaging result of photoacoustic imaging of the tungsten wire with 20 μm diameter, acquired with the tungsten wire located at different positions, using the imaging system 500. In this example the tungsten wire with 20 μm diameter is small enough to be regarded as a spatial point source. FIG. 21A shows the measured in-plane axial and tangential resolution of the ultrasound image as a function of distance from the center of the transducer array to the edge. FIG. 21B shows the measured in-plane axial and tangential resolution of the photoacoustic image as a function of distance from the center of the transducer array to the edge. In FIGS. 21A and 21B, the shadowed regions show a range with isotropic resolution (these regions correspond to the region shown in dashed lines boxes in FIGS. 20A and 20B).

In this example, to shorten the processing time, the ultrasound image reconstruction region is limited to a fan-shaped region at each transmit/receive event and the photoacoustic image reconstruction region is limited to a rectangle (square) region at each laser pulse. The region size is determined by the sensitivity of the acoustic field (FIG. 6) and the spatial resolution (FIGS. 20A to 21B). In this example, the maximal photoacoustic image reconstruction region is 30 mm×30 mm. The results also show that the system can provide a nearly isotropic resolution within a region of 15 mm×15 mm. The center portion has the highest resolution, which is 140.3 μm for ultrasound imaging and 151.7 μm for photoacoustic imaging in the axial direction, and 141.5 μm for ultrasound imaging and 158.9 μm for photoacoustic imaging in the tangential direction.

The speed of sound optimization method is further validated in in vitro experiments performed using the three-layer phantom of FIG. 22. Detailed construction of the phantom is described above. For the in vitro validation, the three-layer phantom is imaged using system 500 and the rod diameter in the innermost layer/portion is measured. In this example, although there exists acoustic mismatch between different layers/portions in the phantom and the coupling medium (water), substantially undistorted images can be reconstructed and a correct rod size can be determined by using the optimized speed of sound value in the reconstruction. FIG. 23A shows the ultrasound image reconstructed using the optimized speed of sound value whereas FIG. 23B shows the photoacoustic image reconstructed using the optimized speed of sound value.

To further verify the performance of the system 500, dual-modal ultrasound and photoacoustic imaging experiment of animal anatomy and dynamics is performed. In the imaging experiment, adult six-week-old female nude mice (BALB/c mouse, ~28 g) are used for in vivo mice trunk imaging using the system 500. During the imaging experiment, the mice is supported by the animal holder 514B and is anesthetized with ~2% vaporized isoflurane at 0.8 L/min. The mice is immersed in water (as coupling medium) in the container 518, and the scanning cross-section positions can be adjusted by the motorized control device 514A moving the holder 514B relative to the transducer elements. The temperature of the water in the container 518 is maintained at 30° C. and monitored with a temperature sensor 520 with a thermocouple 520A.

Two different imaging speeds, 10 Hz and 20 Hz, are used respectively to image the anatomy and dynamics of the mice using the system 500. For the 10 Hz imaging operation, co-registered ultrasound and photoacoustic images are obtained (with image reconstruction using the optimized speed of sound value) from the upper thoracic cavity to the pelvic cavity with a 1-mm step size in the elevational scanning direction. Further, ultrasound and photoacoustic images at the cross-section of the thoracic cavity and the abdominal cavity are continuously recorded. For the 20 Hz imaging operation, one ultrasound image is obtained and used to optimize the speed of sound value at the beginning, then multiple photoacoustic images are continuously recorded (with image reconstruction using the optimized speed of sound value). The wavelength of laser pulses used for photoacoustic imaging is 1064 nm and the laser fluence on the skin is approximately 15.9 mJ/cm$^2$. The hemodynamics in the heart wall of the mice are visualized and analyzed with the 20 Hz photoacoustic imaging. 16 seconds (320 frames) are recorded in the thoracic cavity. A region of interest on the heart wall is selected and segmented from the photoacoustic images. Displacement induced by the heartbeat and respiration are calculated. The change in displacement form a time trace. The Fourier analysis of the time trace shows the respiration and heartbeat frequencies. In the spectral analysis, a second-order high-pass filter (0.15 Hz cutoff frequency) is used to remove low-frequency interferences. To calculate the main artery maps, every pixel of the time-lapsed photoacoustic images are processed using the Fourier analysis. The magnitude at the heart-beat frequency is computed and used to encode each pixel with pseudo-colors.

FIGS. 24A to 27B illustrate the results of the dual-modal ultrasound and photoacoustic imaging experiment of animal anatomy and dynamics (non-invasive imaging of the body of the mice).

Figure 25:
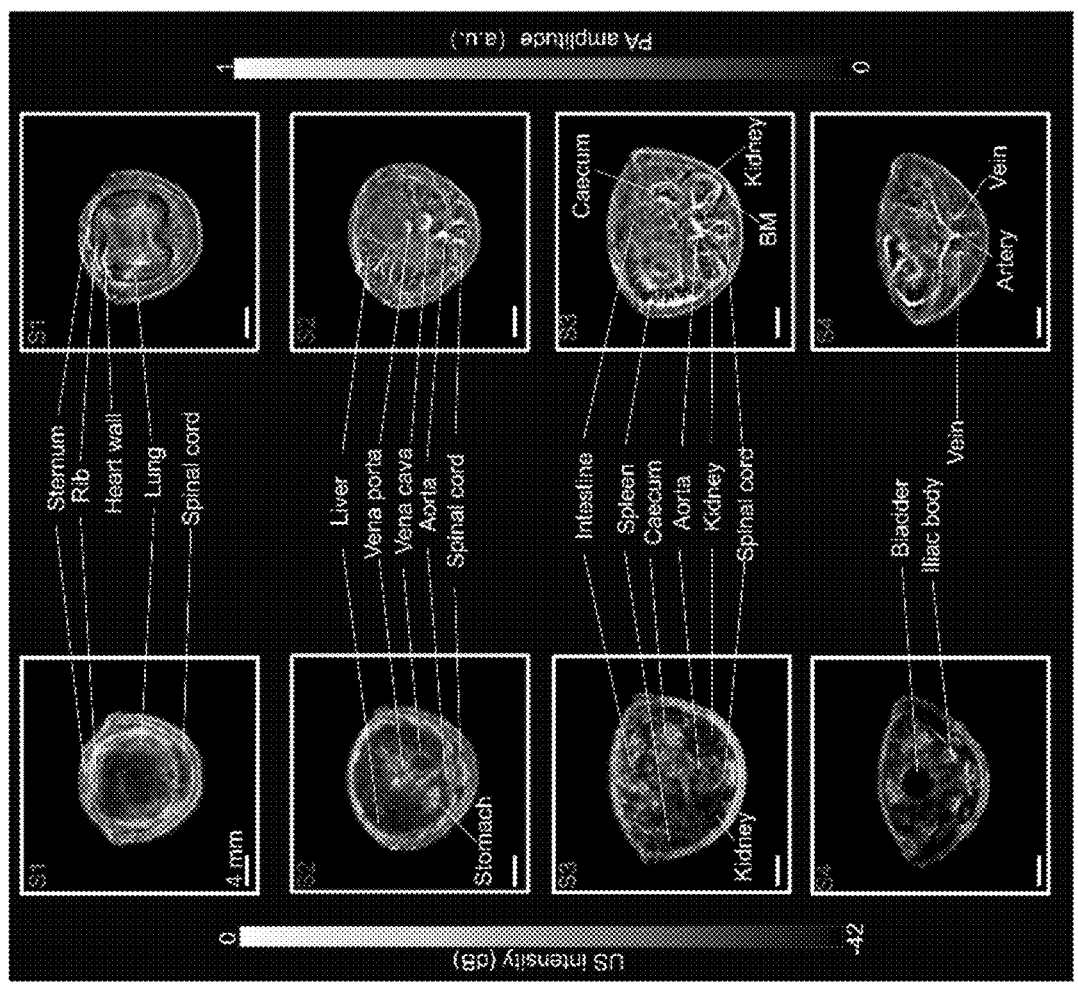
FIG. 25 is an illustration of images of representative ultrasound and photoacoustic images of cross sections of the mice of FIG. 24A imaged by the imaging system of FIG. 5 and reconstructed using respective optimized speed of sound value.

FIGS. 24A to 25 relate to imaging of the animal anatomy. FIG. 24A illustrates a mice and four example cross sections of the mice, from the upper thoracic cavity to the pelvic cavity, imaged by the imaging system 500. At each cross-section, the mice is first imaged with one round of ultrasound imaging to optimize the speed of sound value, and then continuously imaged with multiple rounds of photoacoustic imaging at 20 Hz for 16-seconds (320 frames). FIG. 24B shows the variations of the total coherence factor, or coherence factor summation (CFS) value, for different calculated average speed of sound value for each of the cross sections illustrated in FIG. 24A. The optimized speed of sound value for each respective cross section is the speed of sound value corresponding to the peak of the CFS value curve. FIG. 25 shows representative cross-section images (ultrasound and photoacoustic images) imaged with the system 500 (in the S3 photoacoustic image, BM refers to backbone muscles). Although not illustrated, a comparison is performed on photoacoustic images at the liver region reconstructed with the optimized speed of sound value (1515 m/s) and a wrong speed of sound value (1510 m/s), and it is believed that the differences in images reconstructed using these values (with a 0.3% difference) may not be readily differentiated by naked eye hence the optimal value can be easily missed. The reconstruction results show that the speed of sound optimization method in this example can minimize blurring and artifacts of the blood vessel features. Referring to FIG. 25, the dual-modal ultrasound and photoacoustic imaging provides complementary contrasts and different anatomical details: the vessels (heart wall in the thoracic cavity, abdominal aorta, vena cava, and vena porta in the abdominal cavity) and vascularized organs (liver, kidney, and spleen in the abdominal cavity) are more prominently shown in the photoacoustic images; some other organs, for example, the stomach (Abdominal cavity), the bladder, and the iliac body (Pelvic cavity) are unobservable in photoacoustic images but more prominently shown in the ultrasound images.

Figure 26A:
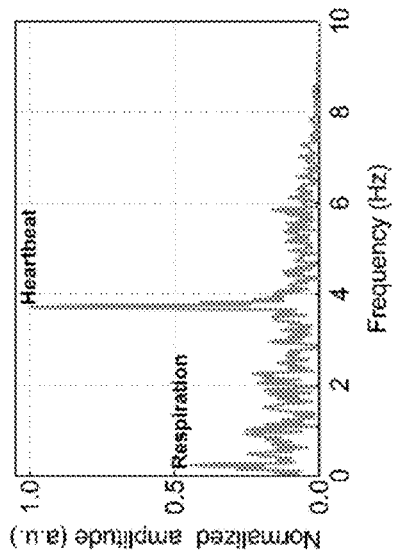
FIG. 26A is an illustration of dynamic imaging of the heart (heart wall motion) of the mice of FIG. 24A using the imaging system of FIG. 5, showing monitoring of respiration and heartbeat of the mice.
Figure 26B:
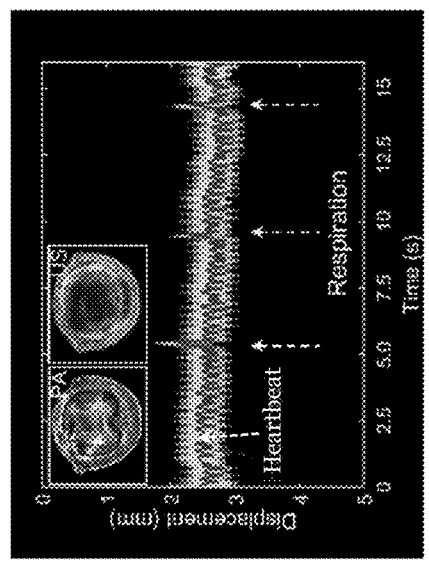
FIG. 26B is a graph showing the respiratory and heartbeat frequencies in FIG. 26A obtained by Fourier transform.

FIGS. 26A to 27B relate to imaging of the animal dynamics. FIG. 26A illustrates dynamic imaging of the heart (heart wall motion along the solid line marked on the inset photoacoustic image) of the mice using the imaging system 500, and shows associated respiration and heartbeats. The traces of the heart wall motion are highlighted with solid lines. FIG. 26B shows a result of Fourier transform of the heart wall displacement, which reveals the respiratory and heartbeat frequencies. In this example, as the 20 Hz photoacoustic imaging speed is higher than the Nyquist sampling rate of the mice heartbeat under anesthetic conditions, the respiration and heartbeat motions can be recorded. Through temporal spectral analysis, the respiration frequency of 0.2 Hz and the heartbeat frequency of 3.7 Hz are extracted from the photoacoustic images.

Figure 27A:
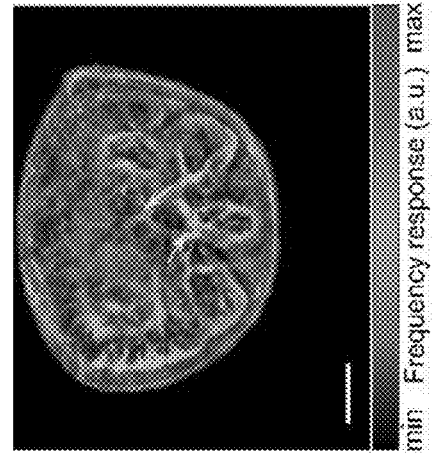
FIG. 27A is an illustration of an arterial map with the heartbeat frequency in the liver region of the mice.
Figure 27B:
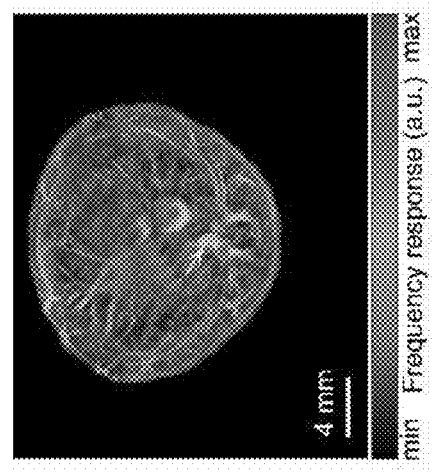
FIG. 27B is an illustration of an arterial map with the heartbeat frequency in the kidney region of the mice.

FIGS. 27A and 27B illustrate arterial maps encoded with the heartbeat frequency in the liver region and the kidney region respectively. Using the detected heartbeat frequency, 16 seconds of photoacoustic imaging data at the cross-sections of the liver and the kidney are processed. As shown in FIGS. 27A and 27B, the arteries with heart rate-synchronized pulsation can be separated from others.

Although not illustrated, to demonstrate the 10 Hz ultrasound and photoacoustic imaging performance, two different cross-sections from the upper thoracic cavity to the abdominal cavity are monitored. Each cross-section records 16.2 seconds of co-registered ultrasound and photoacoustic images (162 frames for each). The speed of sound value is updated when the cross-sectional position changes. Both the ultrasound and photoacoustic images are reconstructed using the matched/optimal speed of sound value. A whole-body scanning from the upper thoracic cavity to the pelvic cavity can be performed with high speed and high image quality.

To demonstrate that the system 500 can be used in clinical applications, dual-modal ultrasound and photoacoustic imaging of human fingers is performed. In this example, the system 500 can optimize the speed of sound value in real-time so the image quality is robust even when unknown acoustic coupling media is used. In this example, the coupling media (water) temperature is set to 23° C. that corresponds to a 1491.3 m/s speed of sound value. Different finger diameters further induce variation in the average speed of sound value. Co-registered ultrasound and photoacoustic images data of the joints in the five fingers are acquired. The optimal average speed of sound values are calculated using the above-mentioned method in real-time and then used in the ultrasound and photoacoustic image reconstructions. The optical wavelength for photoacoustic imaging is 1064 nm and the laser fluence on the skin is approximately 12.7 mJ/cm$^2$.

Figure 28:
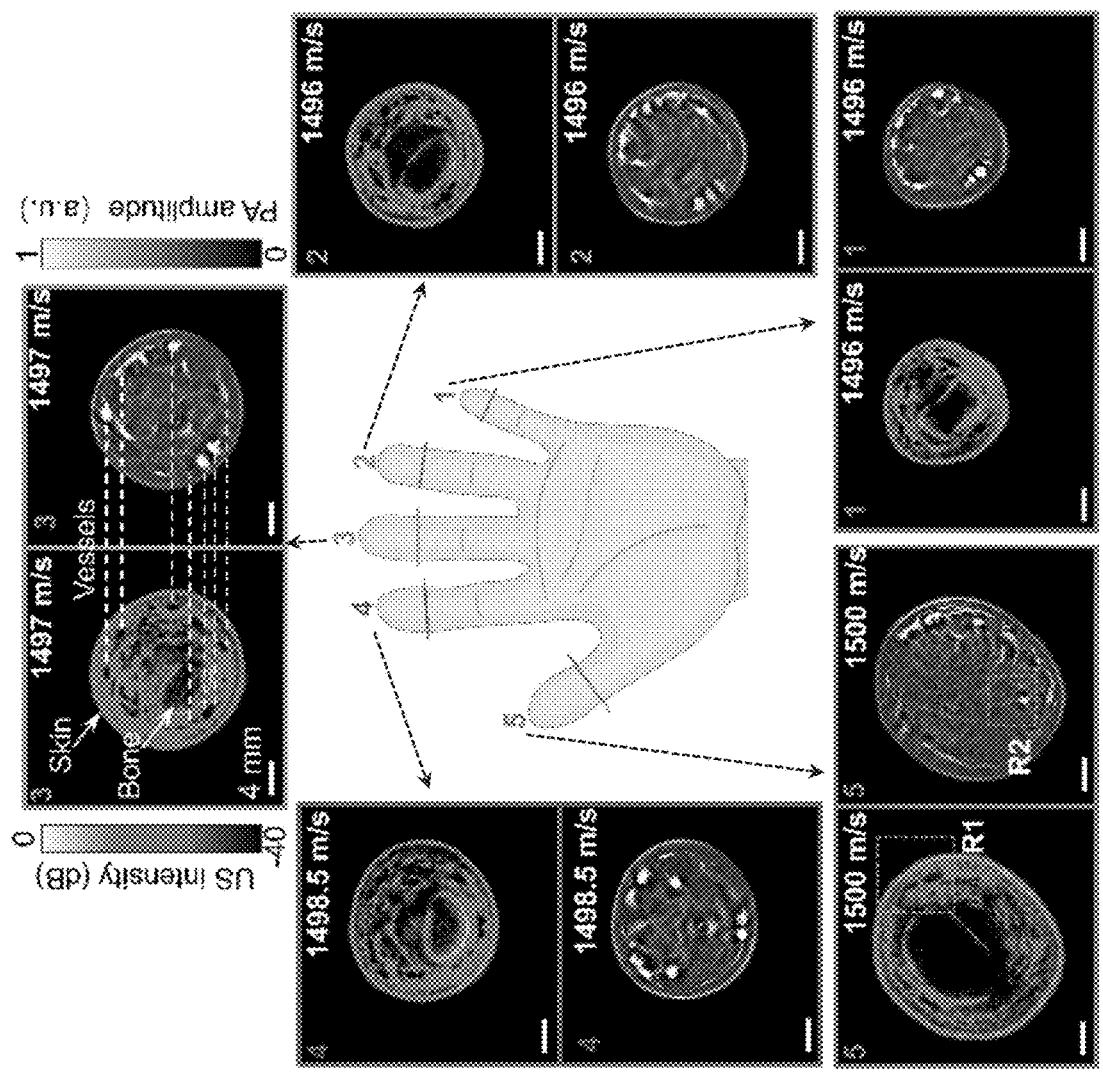
FIG. 28 is an illustration of images of representative ultrasound and photoacoustic images of cross sections of human fingers obtained using the imaging system of FIG. 5, each reconstructed using respective optimized speed of sound value.
Figure 29B:
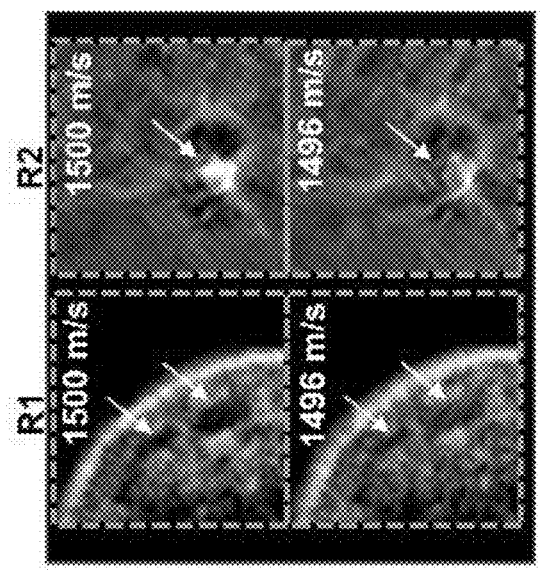
FIG. 29B is an illustration of comparison of the differences in the ultrasound and photoacoustic images of the thumb reconstructed using the optimized speed of sound value for the little finger and the ultrasound and photoacoustic images of the thumb reconstructed using the optimized speed of sound value for the thumb.

FIGS. 28 to 29B illustrate the human fingers imaging result.

FIG. 28 shows representative ultrasound and photoacoustic images of cross sections of human fingers obtained using the imaging system 500, each reconstructed using respective optimized speed of sound value. The white dashed lines at the top inset images illustrate that the high photoacoustic signals from blood vessels correspond to anechoic regions in the ultrasound images. The co-registered ultrasound and photoacoustic images exhibit rich features, such as the skin, blood vessels, and bones.

Figure 29A:
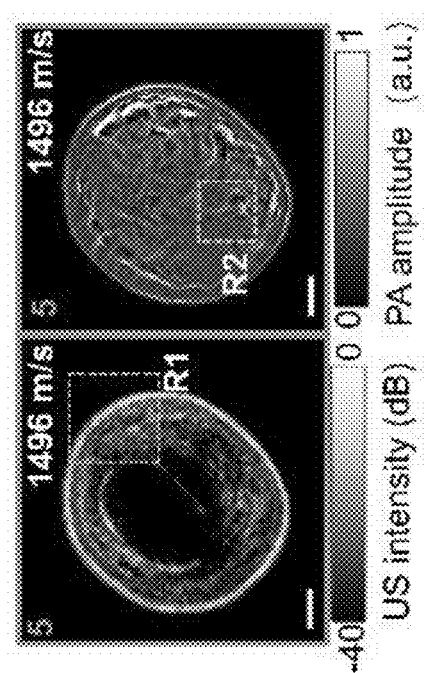
FIG. 29A is an illustration of ultrasound and photoacoustic images of the thumb reconstructed using the optimized speed of sound value for the little finger.

FIG. 29A shows ultrasound and photoacoustic images of the thumb reconstructed using the optimized speed of sound value for the little finger (i.e., not optimized for the thumb). FIG. 29B shows a comparison of the differences in the ultrasound and photoacoustic images of the thumb reconstructed using the optimized speed of sound value for the little finger and the ultrasound and photoacoustic images of the thumb reconstructed using the optimized speed of sound value for the thumb. The part of the thumb shown correspond to the dashed box regions R1, R2 in FIG. 29A.

From FIG. 28 it can be seen that although the speed of sound value is dependent on the object size, coupling medium temperature, and possibly the physiological status of the object/human being imaged, the system 500 in this example can provide robust high-quality images for the finger joints. Different fingers, assuming they are generally round in cross section, have different diameters. The average speed of sound value of the little finger is 1496 m/s, which is smaller than the speed of sound value of the thumb at 1500 m/s. As shown in FIGS. 29A and 29B, the thumb features show larger distortions if the speed of sound value optimized for the little finger is used in its reconstruction.

In this example, the system 500 can enable full view dual-contrast (ultrasound and photoacoustic) imaging with high speed and optimized speed of sound for image reconstruction. Co-registered ultrasound and photoacoustic images provide complementary contrasts can reveal features that are not readily distinguishable by a single modality. One of the features of this example is real-time speed of sound value optimization in dual-modal imaging reconstruction. The automatic speed of sound calculation or optimization operation and can rapidly determine the optimal speed of sound value. The automatic speed of sound calculation or optimization operation reduces the reconstruction time by avoiding subjective variability (due to manual input) and/or avoiding time-consuming iteration (by computer). In this example, the speed of sound optimization uses only the ultrasound data, hence optical fluence attenuation has little effect on its accuracy. The system in this example is suitable for scenarios that require real-time processing and displaying, for example, evaluating vascular perfusion function, investigating pharmacokinetics and pharmacodynamics spanning different organs, or intraoperative monitoring. The high imaging speed enables whole-body imaging and continuously collecting of dynamic physiological information. The system can support fast dual-contrast imaging. Imaging speed can be improved by selective and parallel images reconstruction. Taking advantage of the co-registered dual-modal imaging data, the optimal speed of sound value can be determined by maximizing the constructive interference in the ultrasound image, which is relatively efficient, robust, and insensitive to noises.

Example 2

The inventors of the invention have devised, through research, experiments, and/or trials, that another method to perform image reconstruction in dual-modal ultrasound and photoacoustic imaging and imagine processing would be to use multiple (e.g., two) speed of sound values, which could achieve better image quality over the use of a single speed of sound value in the entire imaging field for reconstruction. In this method, the field of ultrasonic propagation has to be divided into multiple (e.g., two) compartments, with each compartment assigned a respective speed of sound value for reconstruction.

The inventors of the invention have realized, through research, experiments, and/or trials, that the use of two speed of sound values poses two technical challenges. The first challenge concerns how the compartments can be segmented efficiently. The second challenge is how the optimal speed of sound values for the different compartments. The inventors of the invention have appreciated that the use of manual segmentation of the compartments or manual visual tuning the speed of sound values can be time-consuming and subjective hence inaccurate.

Without loss of generality, the inventors of the invention have devised, in this example, systems and methods associated with ultrasound and photoacoustic computed tomography that can automatically segment two compartments and determine the optical speed of sound values for image reconstruction. The inventors of the invention have devised, in this example, a speed of sound optimization method that enables automatic speed of sound compensation using two speed of sound values in dual-modal ultrasound and photoacoustic imaging as well as ultrasound and photoacoustic computed tomography.

Figure 30:
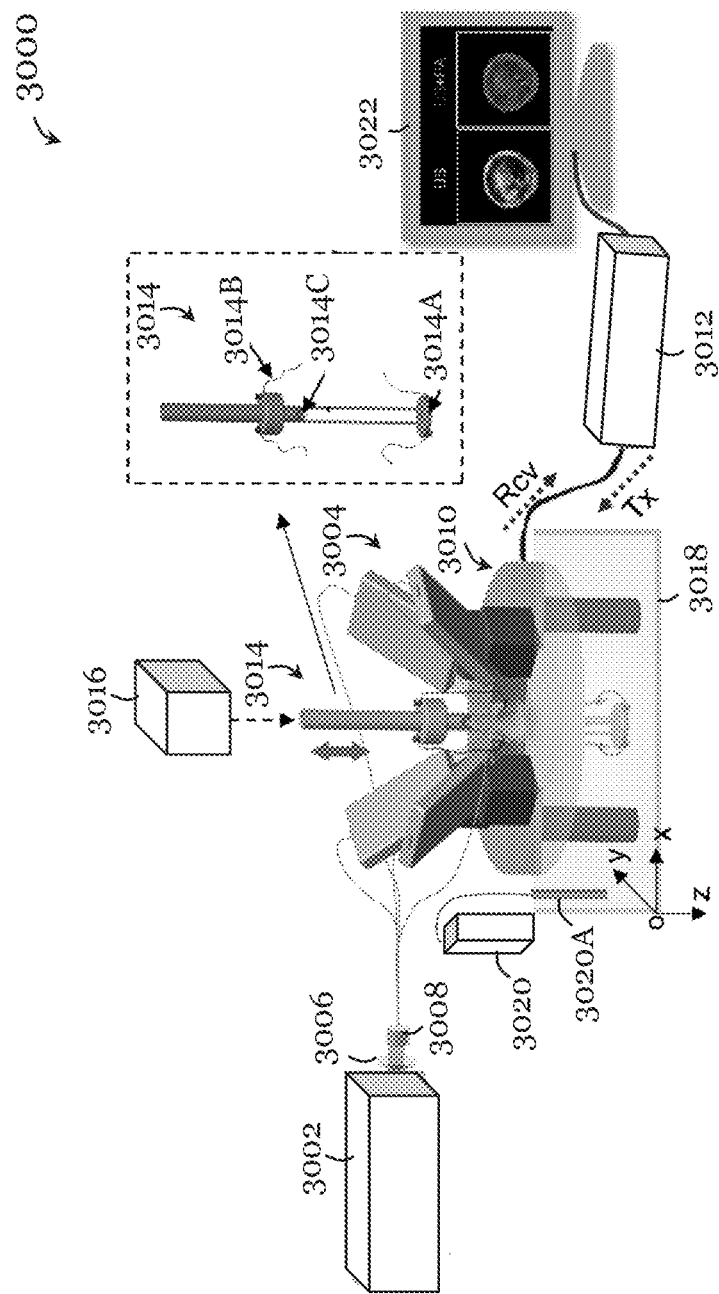
FIG. 30 is a schematic diagram of an experiment setup of an imaging system in one embodiment, with a close up view of the animal holder.

FIG. 30 shows an experiment setup of an imaging system 3000 in this example.

The imaging system 3000 includes an irradiation unit with a laser module arranged to irradiate an object to be imaged with the laser radiation, to facilitate photoacoustic excitation. The laser module includes a laser source 3002, a laser fiber unit 3004, a filter 3006 arranged in the path of the laser emission path of the laser source 3002 for filtering the laser radiation emitted by the laser source 3002, and a coupler 3008 arranged to optically couple the laser radiation emitted by the laser source 3002 into the laser fiber unit 3004. In this example, the laser source 3002 is Q-switched Nd: YAG laser (Spectra-Physics, Santa Clara, CA, USA) that can provide nanosecond laser pulses (e.g., 5 ns to 8 ns laser pulses) at 20 Hz. The laser source 3002 can provide laser wavelength of 1064 nm. The laser fiber unit 3004 includes four optical fiber bundles arranged to be distributed, angularly, around a holder that holds the object (an animal in this example) during imaging. Each of the optical fiber bundles are arranged in a substantially cuboidal housing. A lower or distal end of each housing or optical fiber bundle includes a 32 mm×1 mm rectangular window. The lower or distal end is oriented at 60° relative to an imaging plane (of the object). In this setup, the optical fiber bundles of the laser fiber unit 3004 are fixed and mounted near (above) the ultrasound transducer unit 3010, to provide uniform illumination.

The imaging system 3000 also includes a transducer unit 3010. The transducer unit 3010 includes multiple transducer elements controlled and operable to selectively transmit and receive ultrasound. The transducer unit 3010, or each transducer element, is operable to (i) detect ultrasound waves generated by the object in response to the laser module irradiating the object with the laser radiation, and generate electric signals that form photoacoustic imaging data based on the detected ultrasound waves, and (ii) transmit ultrasound waves towards the object and, in response, detect ultrasound waves reflected, scattered, and/or transmitted by the object, for facilitating ultrasound imaging, and generate electric signals that form ultrasound imaging data based on the detected ultrasound waves. In this setup, the transducer unit 3010 includes 256 transducer elements, angularly spaced apart and arranged in a ring-shaped array, to facilitate full-view in-plane acoustic (e.g., ultrasound) detection. Each of the transducer elements is cylindrically focused in the elevational direction with an acoustic numerical aperture (NA) of 0.2, a radius of 40 mm, a pitch of 0.98 mm, and an elevation size of 14 mm. Each transducer element of the transducer unit 3010 has a central frequency of 6.25 MHz, a two-way (transmit and receive) bandwidth of 58.4% and a one-way (receive) bandwidth of 76.8%.

The imaging system 3000 also includes a control unit. The control unit includes a data acquisition unit 3012. In this example, the data acquisition unit 3012 is Vantage-256 data acquisition unit (Verasonics Inc.). The data acquisition unit 3012 includes 256 channels, each connected and mapped to a respective one of the transducer element in the transducer unit 3010 to facilitate high-speed dual-modal imaging. Each of the channels has an independent amplifier with a tunable gain of up to 54 dB. The data acquisition unit 3012 is operable to sample the ultrasound and photoacoustic signals at 25 MHz and 14 bits resolution. The control unit controls the transducer elements in the transducer unit 3010 to operate as ultrasound transmitter and ultrasound receiver selectively and can electrically disconnect or turn off the transducer elements.

The control unit is further operably connected with the laser source 3002 for synchronization of operation. The control unit may receive a laser trigger signal and, in response, controls the transducer elements to operate as ultrasound receivers to receive broadband ultrasound generated by the object in response to the laser module irradiating the object with the laser radiation. In one example, the control unit may control operation or activation of the laser source 3002.

The imaging system 3000 also includes an object (animal) holder 3014 arranged to hold or support an object to be or being imaged. The enlarged view of the animal holder 3014 shows that the holder includes a frame with a top hollow tube portion through which anesthesia can be provided to the animal to sedate it during imaging, a middle frame portion, and a bottom support plate 3014A with a hole in that allows a tail of an animal to pass through and mounted to the bottom of the frame rod. Strings 3014B for securing the animal's paws/limbs to the holder 3014 are provided at a lower portion of the hollow tube portion and at the bottom support plate. A teeth holder 3014C for supporting the teeth of the animal is arranged at a lower end of the hollow tube portion. An anesthesia unit with an anesthesia source 3016 may be fluidly coupled with the animal holder 3014 (via the hollow tube portion) to deliver suitable dosage of anesthesia to the animal during imaging (to reduce movement) when the animal is held by the holder 3014.

The imaging system 3000 also includes a container 3018 for containing coupling medium in which the object to be or being imaged is partly immersed. In one example, the container 3018 contains a coupling fluid/liquid, which, during imaging, is to be arranged between the object (the part of it) to be or being imaged and the transducer elements of the transducer unit 3010. To image different sections of the object, the animal holder 3014 can be moved up and down relative to the transducer unit 3010. The movement can be performed by a motorized control device (not illustrated) or manually. A temperature sensor 3020 with a thermocouple 3020A immersed in the coupling fluid may be used to detect or monitor temperature of the coupling medium during imaging.

A data processing system 3022 for processing imaging data obtained from the imaging system 3000 may be provided. The data processing system 3022 is in data communication with the control unit or the data acquisition unit 3012 to receive the ultrasound imaging and photoacoustic imaging data. In this embodiment, the data processing system 3022 may be considered as part of the imaging system 3000. The data processing system 3022 may be used to implement, at least partly, the methods in this example.

Figure 31:
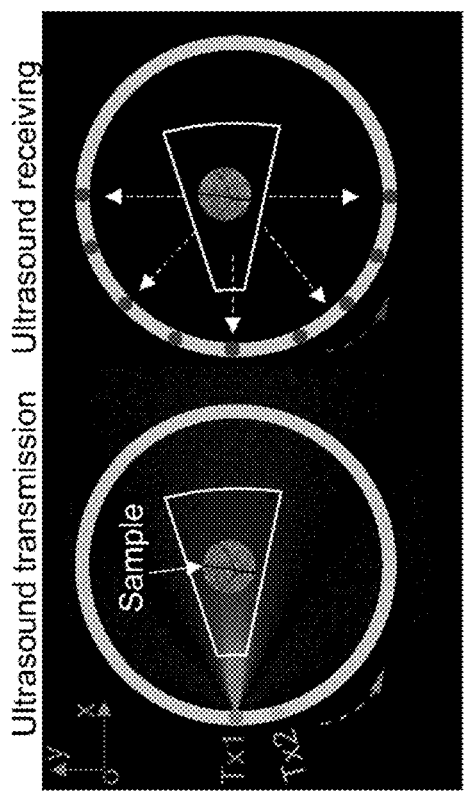
FIG. 31 is an illustration of an ultrasound imaging transmit and receive sequence in one embodiment for use in the imaging system of FIG. 30.

FIG. 31 shows an example ultrasound imaging transmit and receive sequence for use in the imaging system 3000. This sequence is based on sequential active excitation (ultrasound transmission) of each transducer element and corresponding parallel detection (ultrasound detection) by half of the transducer elements. FIG. 31 also shows an acoustic simulation at the 1st position (transducer element 1), with fan-shaped region defined by the white solid line defining the reconstruction region at one transmission event. The skilled person understands that the fan-shaped region for different transmitters (different transducer elements as transmitter) will be different. In one example, to perform ultrasound imaging, a synthetic transmit aperture (STA) approach is used to collect the ultrasound signals. The transducer elements in the ring-array are sequentially excited with a 1-cycle sinusoidal pulse to transmit ultrasound waves, at a 250 µs interval between every transmission. For each respective excitation/transmission, back-scattered ultrasound signals (pulse-echo signals) are detected by 128 transducer elements substantially simultaneously (with little or no time delay). For each respective excitation/transmission, the respective 128 transducer elements (including the emitting element) as receivers are on the same side as the emitting element, and the respective remaining 128 transducer elements are electronically switched off to reduce interference.

Figure 32:
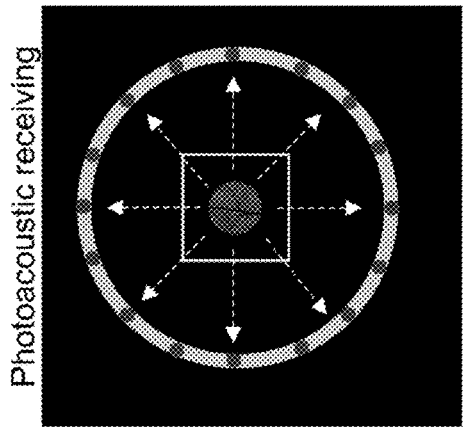
FIG. 32 is an illustration of photoacoustic imaging ultrasound receive sequence in one embodiment for use in the imaging system of FIG. 30.

FIG. 32 shows an example photoacoustic imaging ultrasound receive sequence for use in the imaging system 3000. In one example, to perform photoacoustic imaging, a 1064 nm laser pulse is irradiated on the object and all 256 transducer elements operate as detectors after each laser pulse, e.g., in ~50 is after each laser pulse. FIG. 32 also show a square region defined by the white solid line defining the reconstruction region at one/each transmission event. The skilled person understands that the square region for different transmitters (different transducer elements as transmitter) will be different.

Figure 33:
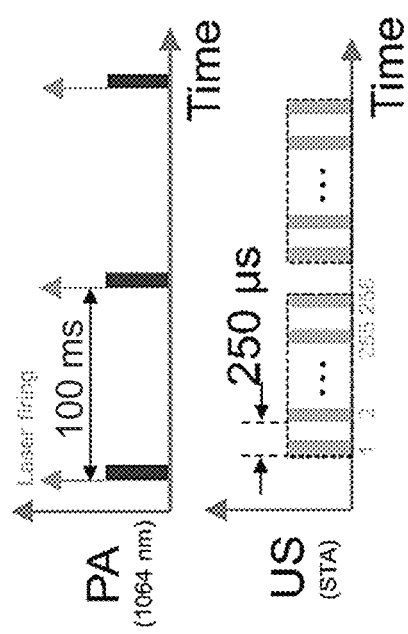
FIG. 33 is an illustration of timing sequence for ultrasound and photoacoustic imaging in one example.

FIG. 33 shows a timing sequence for dual-modal ultrasound and photoacoustic imaging using the system 3000 in one embodiment. As shown in FIG. 33, at each cycle of the sequence, one round of photoacoustic imaging (one laser pulse) is performed and then one round of ultrasound imaging (each transducer element transmits once) is performed. As a result, ultrasound and photoacoustic signals are obtained in an interleaved manner. In this example, the system 3000 can alternate between ultrasound and photoacoustic imaging up to 10 Hz, to achieve a 10 Hz ultrasound and photoacoustic frame rate.

In this example, a speed of sound value optimization operation that involves a segmentation operation and then a speed of sound values determination operation for each of the segments is provided. An image reconstruction operation may be performed after the speed of sound value optimization operation.

Figure 34:
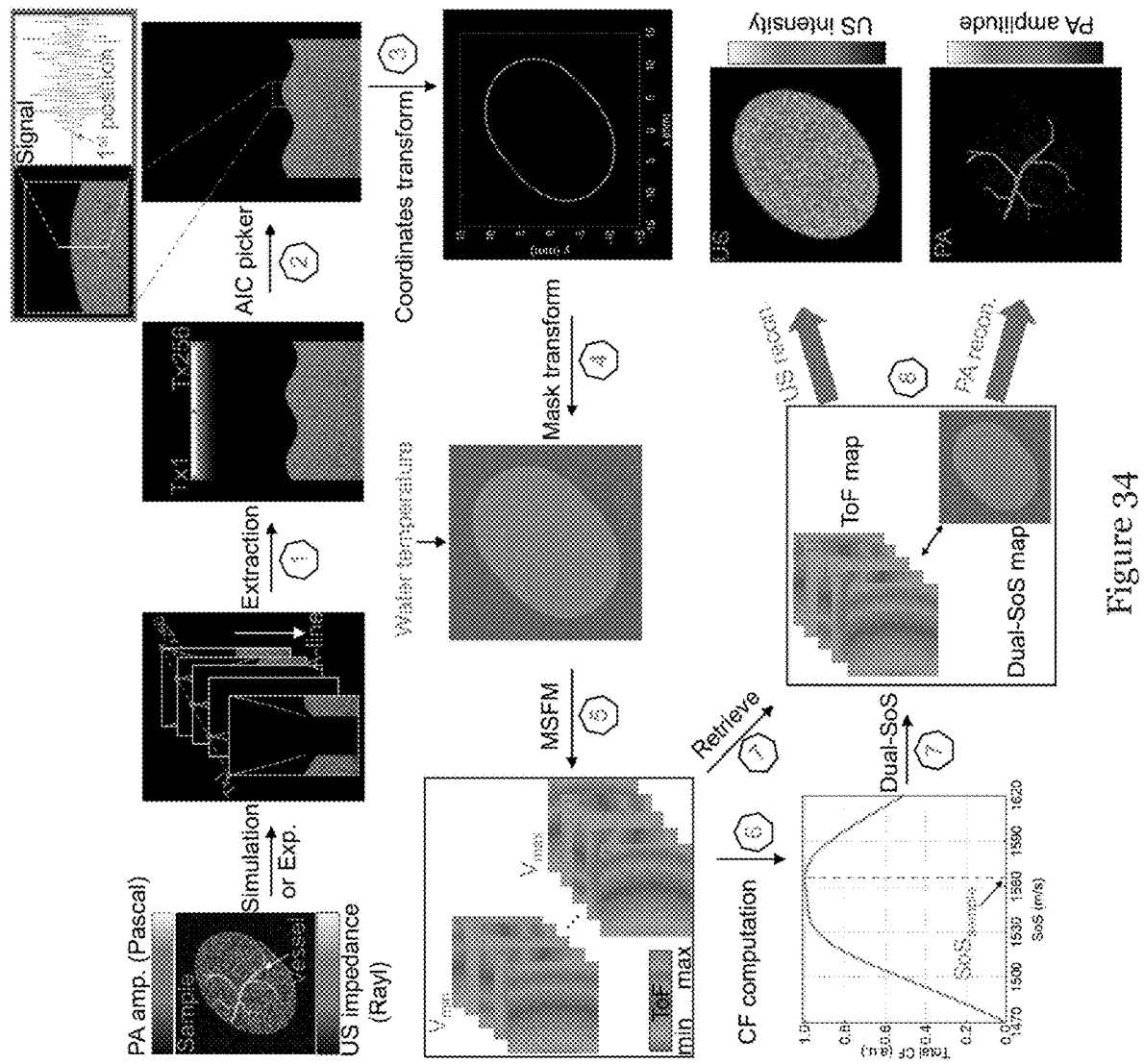
FIG. 34 is an illustration of a method for processing photoacoustic and ultrasound imaging data, e.g., obtained from the imaging system of FIG. 30 in one embodiment.

FIG. 34 shows an example method for processing photoacoustic and ultrasound imaging data obtained from the imaging system 3000. The method includes the speed of sound value optimization operation and the image reconstruction operation.

In this example, the segmentation operation uses a segmentation method that can automatically separate the sample object from the coupling medium in the ultrasound image. First, in step 1, at each ultrasound transmit/receive event, an A-line signal received by the transmitting transducer element is extracted. By the end of one round of ultrasound imaging, the 256 A-line signals are combined to form a transmission (Tx) map. In step 2, the first ultrasound arrival positions are detected using an improved Akaike information criterion (AIC) picker algorithm, based on the teachings in C. Li, L. Huang, N. Duric, H. Zhang, C. Rowe, *An improved automatic time-of-flight picker for medical ultrasound tomography*, Ultrasonics. 49 (2009) 61-72. The first arrival positions (see signal plot in top right corner of FIG. 34) represent the boundary between the sample and the coupling medium. In the algorithm, a temporal window S with a length $$N = \left(\frac{2R}{SoS_{water}} \times f_s\right)$$

is determined on each A-line signal, where R is the radius of the ring-shaped transducer array, $SoS_{water}$ is the speed of sound of the coupling medium (water), and $f_s$ is the sampling frequency. The AIC values are calculated as $$AIC(k) = k \times \log(\text{var}(S(1, k))) + (N - k + 1) \times \log(\text{var}(s(k+1, N))) \quad (3)$$

$$\text{var}(S(i, j)) = \frac{1}{j-i} \sum_{p=i}^{j} (S(p) - \bar{S}(i, j))^2, \ 1 \le i < j \le N$$

where k ($1 \leq k < N$) divides the temporal window S into S (1,k) and S(k+1, N), var is the variance function, $\overline{S}(i,j)$ is the mean value in the range of i to j. An Akaike weight $W_k$ at the $k^{th}$ position is determined as:

$$W_k = \frac{e^{(-\Delta_k/2)}}{\sum_{p=1}^{N-1} e^{(-\Delta_p/2)}} \quad (4)$$

where $\Delta_k$ is AIC(k)−min(AIC).

Then, in step 3, the first arrival positions on the transmission channel $Tx_i$ are determined as $$P_{first}^{Tx_i} = \sum_{p=1}^{N-1} W_p \times p, \quad (5)$$

The distance ($d_{Tx_i}$) from the transmission element to the nearest point on the sample surface is $$\frac{1}{2} \times P_{first}^{Tx_i} \times \frac{1}{fs} \times SoS_{water}.$$

Therefore, 256 pairs of coordinates on the boundary between the sample object and the coupling medium can be obtained by coordinate transformation as $$X_{Tx_i} = \left(R - \frac{1}{2} \times P_{first}^{Tx_i} \times \frac{1}{fs} \times SoS_{water}\right) \times \cos\theta_{Tx_i} \quad (6)$$

$$Y_{Tx_i} = \left(R - \frac{1}{2} \times P_{first}^{Tx_i} \times \frac{1}{fs} \times SoS_{water}\right) \times \sin\theta_{Tx_i}$$

where $\theta_{Tx_i}$ is the azimuth angle of the transmission channel $Tx_i$.

In step 4, the 256 pairs of coordinates form a closed loop to segment two compartments. A mask mapping the different segments can thus be determined.

Figure 35B:
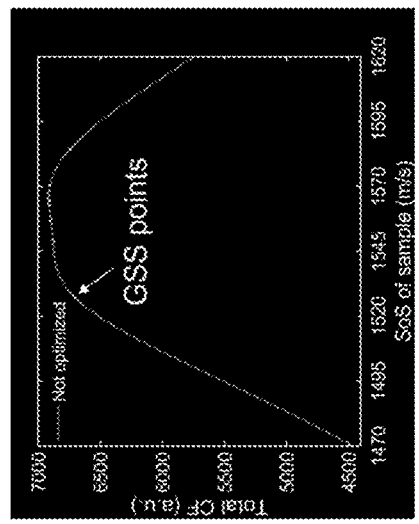
FIG. 35B is an illustration showing a golden section search method for searching for optimal speed of sound for use in image reconstruction.
Figure 35A:
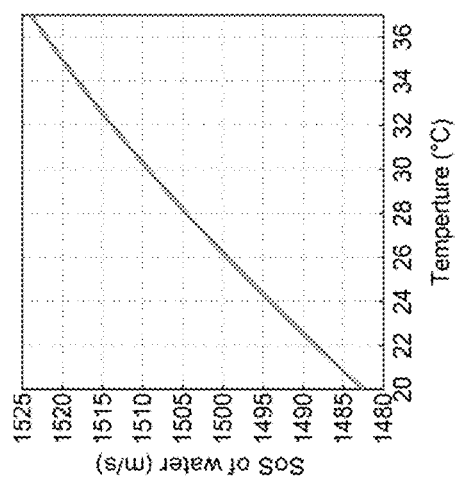
FIG. 35A is a graphs showing the speed of sound in water at different temperatures.

In this example, the speed of sound (SoS) value in the coupling medium (water) can be determined based on its temperature (at the time of imaging). To this end, the system 3000 uses a temperature sensor 3020 to measure the water temperature during imaging. The relationship between the speed of sound value for water and the temperature of the water is shown in FIG. 35A. In this example, the speed of sound value for the coupling medium (water) can be readily determined by referencing the relationship which is predetermined.

The inventors of the invention have realized that when correct or optimal speed of sound value(s) are used in image reconstruction, the ultrasound signals can be coherently summed up.

In this example, to determine the correct speed of sound in the sample, the maximum coherence factor (CF) of the ultrasound signals at different predetermined speed of sound values are determined.

In step 5, a multi-stencil fast marching (MSFM) method, based on the teachings in S. Jeon, W. Choi, B. Park, C. Kim, *A Deep Learning-Based Model That Reduces Speed of Sound Aberrations for Improved in Vivo Photoacoustic Imaging, IEEE Trans. Image Process.* (2021) 8773-8784, is applied to calculate a series of time of flight (ToF) maps under different predetermined speed of sound values. Each ToF map may correspond to a respective speed of sound value. In this example, the MSFM method considers acoustic refraction in the propagation path and calculates the shortest ToF between the transducer element and the reconstructed pixel by solving the eikonal equation:

$$|\nabla T(x, y)| = \frac{1}{SoS(x, y)} \quad (7)$$

where T is the ToF at the reconstructed pixel (x,y).

Then, in step 6, ultrasound images are reconstructed using different ToF maps (one ultrasound image for each ToF map) and the total coherence factor values of the reconstructed images are computed. In this example, the coherence factor value is determined from $$CF_{SoS_{sample}}(x, y) = \frac{\left|\sum_{Rcv=1}^{N_{elm}} \sum_{Tx=1}^{N_{elm}} I(x, y)\right|^2}{N_{elm} \times \sum_{Rcv=1}^{N_{elm}} \left|\sum_{Tx=1}^{N_{elm}} I(x, y)\right|^2} \quad (8)$$

where $SoS_{sample}$ is a predetermined speed of sound value, Rcv and Tx are the transmission and receiving transducer element indexes, $N_{elm}$ is the number of transducer elements, I(x,y) is the delayed channel data calculated from the ToF map. Finally, the optimal speed of sound for the sample/object is determined from $$\hat{SoS}_{sample} = \arg\max_{SoS_{sample}} f(CFS) \quad (9)$$

where CFS is the total coherence factor summation (CFS) of all pixels, and $f$ is an interpolation function. The interpolation function may be a spline interpolation function.

In this example, a golden section search (GSS) approach, i.e., a golden section search algorithm, is applied to accelerate the processing speed in steps 5 and 6. Compared with a uniform step searching method, the golden section search algorithm can reduce the number of calculations of ToF maps and coherence factors. As an example, when searching for extreme value in the speed of sound value range of 1470 m/s to 1620 m/s, the golden section search method only needs to calculate 16 speed of sound values to achieve 1 m/s accuracy, which is 4.75 times more efficient than the uniform-step method. FIG. 35B shows the result of the golden section search (GSS) approach (in dots) and the result of the uniform step search results (in a line).

Referring back to FIG. 34, after the segmentation operation is performed, and the optimized speed of sound values for the different segments are determined, an image reconstruction operation for reconstructing the ultrasound and photoacoustic images is performed.

In this example, in step 7, the two optimized speed of sound values are applied to the mask to form an optimized speed of sound value map. The optimized ToF maps and the optimized speed of sound value map are used in the image reconstruction operation. In this example, in step 8, the ultrasound and photoacoustic images are reconstructed using a weight-based delay-and-sum beamformer method. One example of the weight-based delay-and-sum beamformer method is disclosed in Y. Zhang, Y. Wang, P. Lai, L. Wang, *Video-rate dual-modal wide-beam harmonic ultrasound and photoacoustic computed tomography, IEEE Trans. Med. Imaging.* 41 (2022) 727-736. The ultrasound image reconstruction at each transmission is confined to a fan-shaped region (FIG. 31). The reconstruction region for the photoacoustic image is a square-shaped region with 30×30 mm² in this example (FIG. 32). Before applying the weight-based delay-and-sum beamformer method to perform reconstruction, the ultrasound and photoacoustic data are pre-processed using a $3^{rd}$-order Butterworth bandpass filter (0.05~8.5-MHz). After reconstruction of the images with weight-based delay-and-sum beamformer method, the ultrasound images are further processed using envelope detection and logarithmic compression to enlarge the display range. For a fair comparison, only the bipolar photoacoustic images without vascularization filtering and contrast-stretching are processed. All these image reconstruction steps are implemented in MATLAB (2019b, MathWorks, USA) on a computer (Inter Core i7@2.60 GHz, 16 GB of RAM, NVIDIA GeForce RTX 2060).

Figure 36:
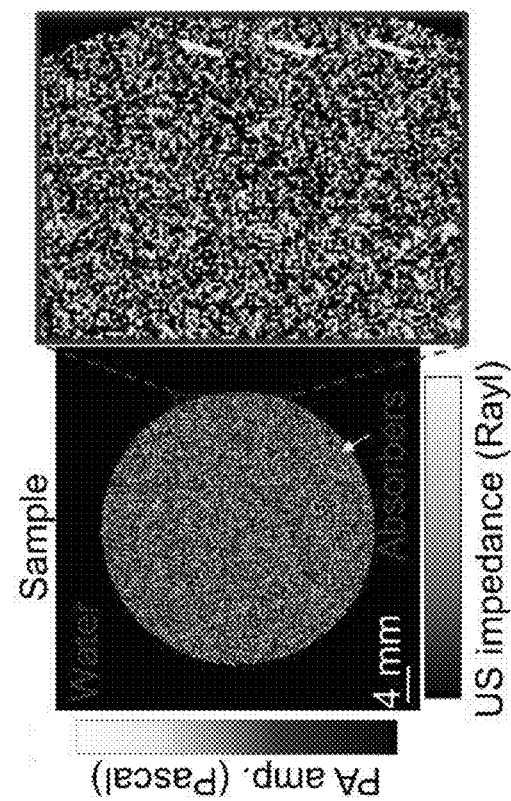
FIG. 36 is an illustration of a numerical phantom in a numerical phantom simulation and reconstruction in one embodiment.

Simulations are performed on the ultrasound and photoacoustic imaging with the speed of sound optimization operation of this example. The simulations are performed using the k-Wave toolbox. The simulated element number and parameters of the transducer elements are the same as those used in example 1. In the simulation, the aperture effect is neglected to ensure that the blurry errors are only caused by inaccurate speed of sound value(s). The coupling medium (water) has a speed of sound of 1500 m/s and a density of 1000 kg/m³. FIG. 36 shows the numerical phantom used in this simulation. The numerical phantom has a circular region with a mm diameter and an speed of sound of 1538±39.4 m/s (mean±standard deviation). The maximal acoustic impedance is 1.7 MRayl. For the ultrasound imaging simulation, 1 cycle sinusoidal pulses are sequentially transmitted from the 256 elements. The receiving sequence is the same as described with reference to FIGS. 30 to 31. In the photoacoustic imaging simulation, a group of absorbers is uniformly distributed in the circular region. Each absorber has a diameter of 0.1 mm and a unit initial pressure. The sampling frequency is set at 53.2566 MHz. The computational grid consists of 1200×1200 pixels and the pixel size is 0.1 mm. An acoustic attenuation ($\alpha=0.75f^{1.5}$) is added in the simulation. The simulations are performed using a graphics processing unit (GPU).

Figure 37:
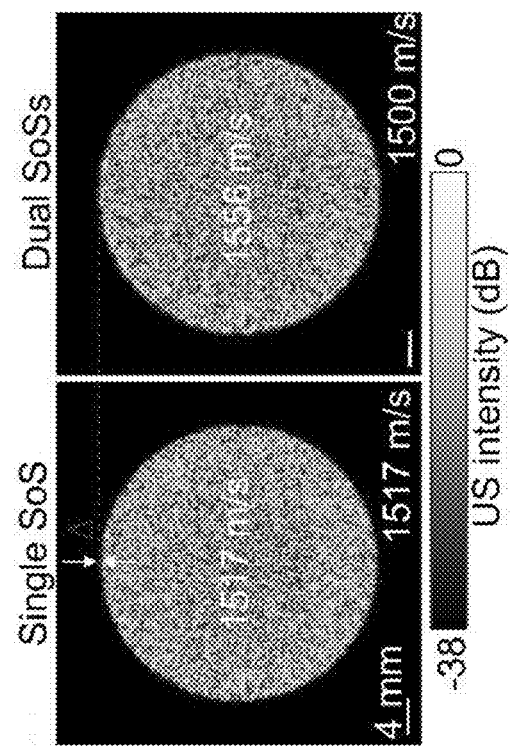
FIG. 37 is an illustration of the ultrasound images of the numerical phantom of FIG. 36 reconstructed with a single speed of sound value for the entire field of view and reconstructed with two speed of sound values (one for the phantom simulated object, another for the coupling medium)
Figure 38:
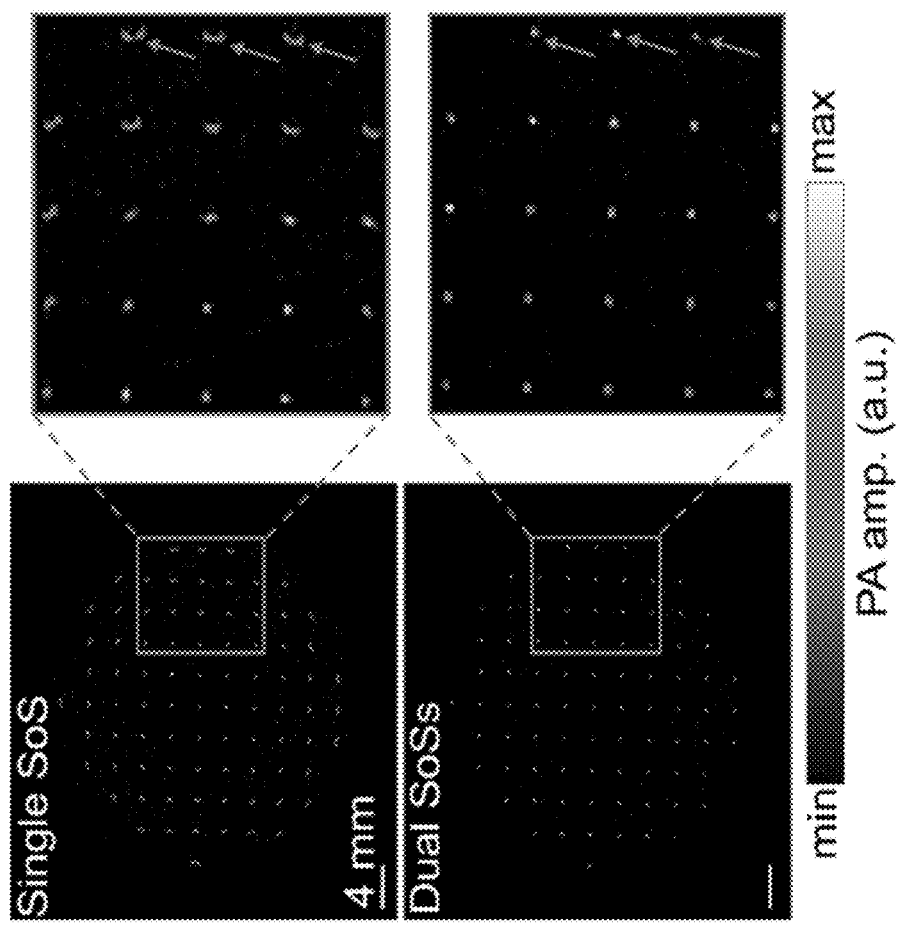
FIG. 38 is an illustration of the photoacoustic images of the numerical phantom of FIG. 36 reconstructed with a single speed of sound value for the entire field of view and reconstructed with two speed of sound values (one for the phantom simulated object, another for the coupling medium FIG. 39A is a photograph of a chicken breast phantom imaged by the imaging system of FIG. 30.

FIGS. 36 to 38 illustrate the simulation result. FIG. 36 shows the numerical phantom used in the simulation. FIG. 37 shows ultrasound image of the numerical phantom of FIG. 36 reconstructed with a single speed of sound value for the entire field of view and ultrasound image of the numerical phantom of FIG. 36 reconstructed with two speed of sound values (one for the phantom simulated object, another for the coupling medium) respectively. FIG. 38 shows corresponding photoacoustic image of the numerical phantom of FIG. 36 reconstructed with a single speed of sound value for the entire field of view and corresponding photoacoustic image of the numerical phantom of FIG. 36 reconstructed with two speed of sound values (one for the phantom simulated object, another for the coupling medium) respectively.

In the simulation of FIGS. 37 and 38, the single speed of sound value used for reconstruction is manually determined via visual assessment of the photoacoustic image sharpness, a technique commonly employed in photoacoustic image reconstruction. In this simulation the single speed of sound value is selected to be 1517 m/s to keep most absorbers in focus (FIG. 38). As shown in the result of FIG. 38, for the photoacoustic image reconstructed using the single speed of sound value, some absorbers close to the boundary are still split, which is unavoidable to keep the center area in focus. The fringing effect is also obtained and is mainly induced by the large acoustic impedance mismatch between the biological tissue and the coupling medium.

In the simulation of FIGS. 37 and 38, the two speed of sound values (one for the phantom simulated object, another for the coupling medium) are determined using the method described above. In particular the speed of sound value for the coupling medium is determined based on the detected temperature of the coupling medium at the time of the imaging, and the speed of sound value for the phantom simulated object is determined based on the coherent factor, or total coherent factor value, calculation. The two speed of sound values are determined to be 1500 m/s for the coupling medium and 1556 m/s for the phantom simulated object/sample. As shown in the result of FIG. 38, for the photoacoustic image reconstructed using the two speed of sound values, almost all absorbers are well reconstructed and in focus, hence the image quality is better than the image reconstructed using one speed of sound value. In this simulation, the single speed of sound approach result underestimates the size of the phantom simulated object/sample whereas the dual speed of sound approach can reduce this error.

Phantom experiments are further conducted with the system 3000 to validate and characterize the ultrasound and photoacoustic imaging with the speed of sound optimization operation of this example. In this experiment, a chicken breast tissue is placed into a container made of fluorinated ethylene propylene (FEP) with a wall thickness of 0.2 mm. One pencil lead (0.7 mm) is inserted into the chicken breast while another pencil lead (0.3 mm) is placed near the edge, to act as absorber. During imaging, the coupling medium (water) temperature is set to 21.9°. The water, fluorinated ethylene propylene (FEP), and chicken breast tissue induced acoustic impedance mismatch. The cavity in the chicken breast further increases acoustic heterogeneity. The laser wavelength of 1064 nm is used for photoacoustic imaging.

FIG. 39A to 39C illustrate the chicken breast phantom experiment result. FIG. 39A shows the chicken breast phantom used in the experiment. The chicken breast phantom includes the chicken breast tissue, the absorber, and the FEP described above. FIG. 39B shows photoacoustic image of the chicken breast phantom of FIG. 39A reconstructed with a single speed of sound value for the entire field of view and photoacoustic image of the chicken breast phantom of FIG. 39A reconstructed with two speed of sound values (one for the object, another for the coupling medium). FIG. 39C is a zoom in view of the boxes in FIG. 39B.

In the experiment of FIGS. 39A to 39C, the single speed of sound value used for reconstruction is manually determined via visual assessment of the photoacoustic image sharpness. In this experiment the single speed of sound value is selected to be 1508 m/s to keep most absorbers in focus. As shown in the result of FIGS. 39B and 39C, for the photoacoustic image reconstructed using the single speed of sound value, the absorber (pencil lead) near the center is suitable reconstructed but the absorber (pencil lead) near the boundary is split and fringing artifacts can be observed.

In the simulation of FIGS. 39A to 39C, the two speed of sound values (one for the object, another for the coupling medium) are determined using the method described above. In particular the speed of sound value for the coupling medium (water) is determined based on the detected temperature of the coupling medium at the time of the imaging, and the speed of sound value for the phantom simulated object is determined based on the coherent factor, or total coherent factor value, calculation. The two speed of sound values are determined to be 1488.2 m/s for the coupling medium (water) and 1546 m/s for the object/biological tissue. As shown in the result of FIGS. 39B and 39C, for the photoacoustic image reconstructed using the two speed of sound values, the absorbers are well reconstructed and in focus, with less artifacts, hence the image quality is better than the image reconstructed using one speed of sound value.

To further verify the performance of the system 3000, dual-modal ultrasound and photoacoustic imaging of animal anatomy is performed. In the imaging experiment, adult six-week-old female nude mice (BALB/c mouse, ~28 g) are used for in vivo imaging using the system 3000. During the imaging experiment, the mice is supported by the animal holder 3014 and is anesthetized with ~2% vaporized isoflurane at 0.8 L/min. The mice is immersed in water (as coupling medium) in the container 3018, and the scanning cross-section positions can be adjusted by the motorized control device (not shown) moving the holder 3014 relative to the transducer elements. The temperature of the water in the container 3018 is maintained at 30° C. and monitored with a temperature sensor 3020 with a thermocouple 3020A. The wavelength for photoacoustic imaging is 1064 nm (optical attenuation in tissue is relatively low at this wavelength) and the laser fluence on the skin is approximately 11 mJ/cm$^2$. In this experiment, the imaging is performed at the cross-section of the liver in the abdominal cavity of the mice.

FIGS. 40 to 47 the results of the dual-modal ultrasound and photoacoustic imaging experiment of animal anatomy and dynamics (non-invasive imaging of the body of the mice).

Figures 40, 41:
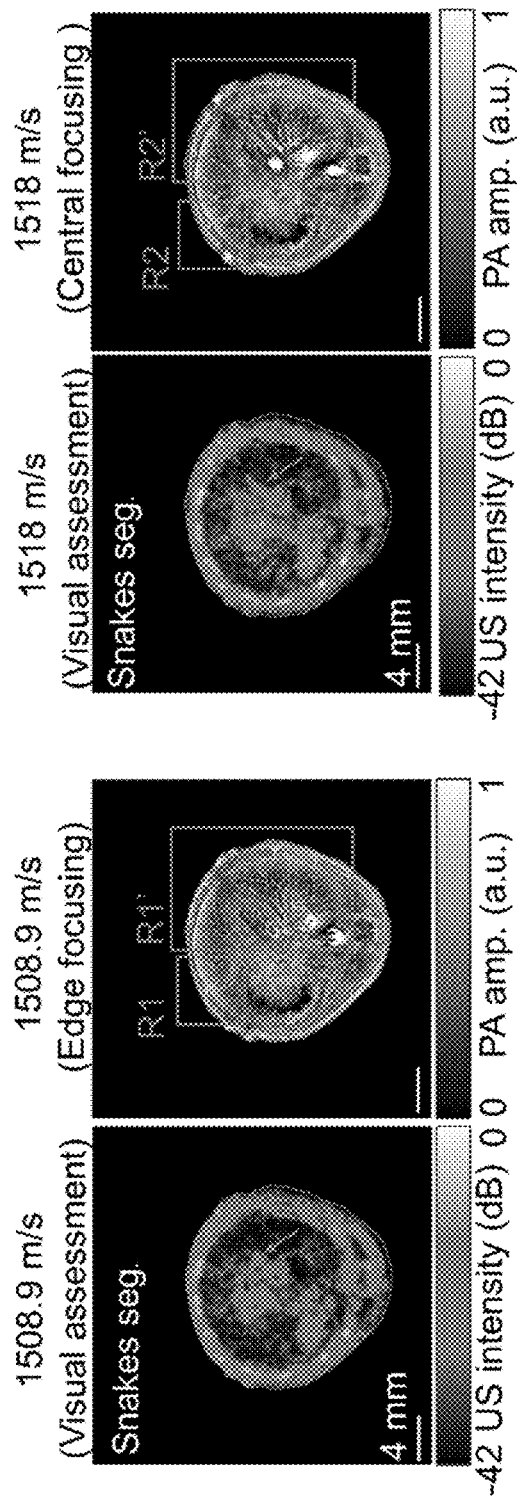
FIG. 40 is an illustration of ultrasound and photoacoustic images of a mice (liver region) imaged by the imaging system of FIG. 30, reconstructed using a single manually selected speed of sound value.
FIG. 41 is an illustration of ultrasound and photoacoustic images of the mice (liver region) imaged by the imaging system of FIG. 30, reconstructed using another single manually selected speed of sound value.

FIGS. 40 and 41 illustrate results of reconstruction using a single speed of sound value. FIG. 40 illustrates ultrasound and photoacoustic images of the liver region of the mice imaged by the imaging system 3000 of FIG. 30 and reconstructed using a single manually selected speed of sound value. FIG. 41 illustrates ultrasound and photoacoustic images of the liver region of the mice imaged by the imaging system 3000 of FIG. 30 and reconstructed using another single manually selected speed of sound value. In each of these two single speed of sound reconstructions, the single speed of sound is each selected by visual assessment of the sharpness of prominent features.

The speed of sound selected for reconstruction of the images in FIG. 40 is 1508.9 m/s to keep the main boundary vessels in focus. The speed of sound selected for reconstruction of the images in FIG. 41 is 1518 m/s to keep the central vascular features in focus. In the processing of the images in FIGS. 40 and 41, to suppress the background noises in the ultrasound and photoacoustic images, the biological tissue boundary is segmented using a snake-based active contour algorithm, based on the teaching of K. Basak, X. Luís Deán-Ben, S. Gottschalk, M. Reiss, D. Razansky, *Non-invasive determination of murine placental and foetal functional parameters with multispectral optoacoustic tomography, Light Sci. Appl.* 2019 81. 8 (2019) 1-10. The snake-based active contour algorithm requires user manipulation and initial guess, and hence is time-consuming and is subject hence inaccurate.

Figures 42, 43, 44, 45:
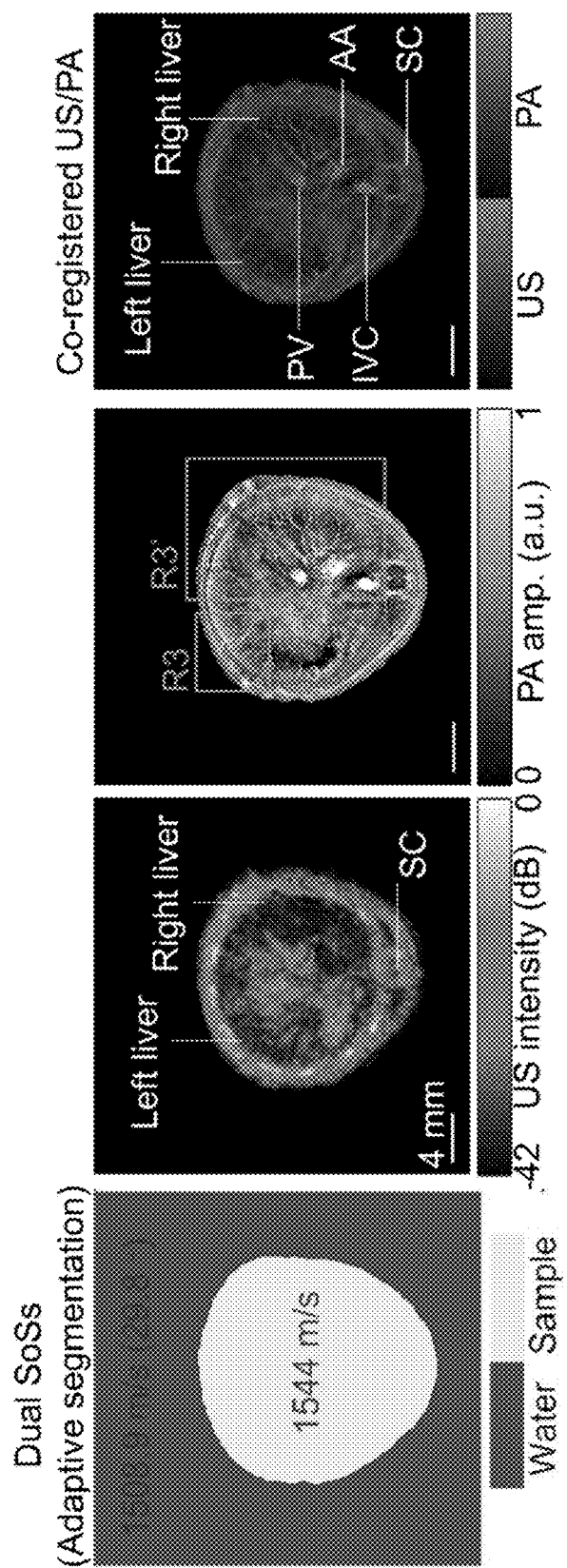
FIG. 42 is an illustration of a mask for the images of the mice produced by an automatic two-compartment segmentation using the method of FIG. 34.
FIG. 43 is an illustration of an ultrasound image of the mice (liver region) imaged by the imaging system of FIG. 30, reconstructed using two optimized speed of sound values.
FIG. 44 is an illustration of a photoacoustic image of the mice (liver region) imaged by the imaging system of FIG. 30, reconstructed using two optimized speed of sound values.
FIG. 45 is an illustration of overlaid ultrasound image in FIG. 43 and photoacoustic image of FIG. 44, which are co-registered.

FIGS. 42 to 45 illustrate results of image reconstruction using two speed of sound values, one for each section (one for the coupling medium, one for the animal), based on the speed of sound value optimization operation and the image reconstruction operation of FIG. 34. FIG. 42 shows a segmentation mask for the images of the mice produced by an automatic two-compartment segmentation operation in the method of FIG. 34. FIG. 43 shows an ultrasound image of the liver region of the mice imaged by the imaging system 3000 of FIG. 30 and reconstructed using two optimized speed of sound values whereas FIG. 43 shows a corresponding photoacoustic image of the liver region of the mice imaged by the imaging system 3000 of FIG. 30 and reconstructed using the two optimized speed of sound values. FIG. 45 shows the ultrasound image in FIG. 43 and the photoacoustic image of FIG. 44 overlaid. The two images are naturally co-registered as they are obtained from the dual-modal imaging system 3000. FIG. 45 shows various anatomical features such as abdominal aorta (AA), inferior vena cava (IVC), portal vein (PV), and spinal cord (SC).

The use of the method in FIG. 34, which determines two optimized speed of sound values for the two sections, does not only provide automatic contour segmentation but also enhance imaging quality for both ultrasound and photoacoustic images. The use of the segmentation mask (FIG. 42) can suppress the background noises for the ultrasound and photoacoustic images, preferably without the operator's intervention. By comparing the results in FIGS. 40 and 41 obtained using a single speed of sound value with the results in FIGS. 43 and 44 obtained using two speed of sound values, it can be seen that the results in FIGS. 40 and 41 cannot achieve global improvement in imaging quality as the central vessels are blurred or the boundary has fringing effects. The overlaid ultrasound and photoacoustic images in FIG. 45 show co-registered high-quality dual-contrast images of the internal organs. This indicates that the system 3000 can provides accurate registration of images independent of breathing induced movement and heart movement of the animal during imaging.

Figure 47:
FIG. 47 is a zoom in view of the boxes (R1', R2', R3') in FIGS. 40, 41, and 44 respectively.
Figure 46:
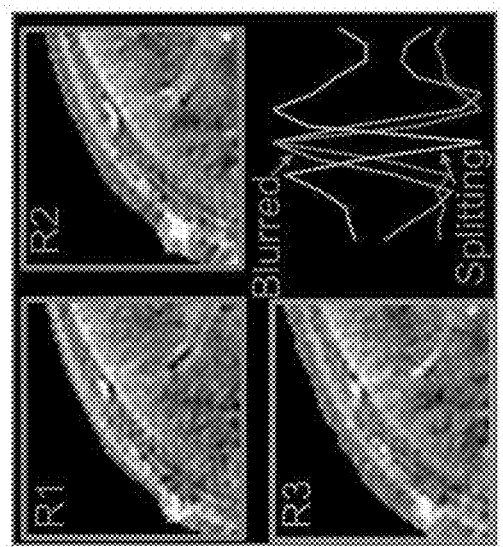
FIG. 46 is a zoom in view of the boxes (R1, R2, R3) in FIGS. 40, 41, and 44 respectively.

FIGS. 46 and 47 are zoom in view of the boxes (R1, R2, R3; R1', R2', R3') in FIGS. 40, 41, and 44 respectively. As shown in FIGS. 46, and 47, the method that uses two speed of sound values in image reconstruction can keep both the boundary (R3) and the central vessels (R3') in focus while internal organs, such as the liver, can be identified.

In this example, the system can enable high-quality ultrasound and photoacoustic imaging with co-registered dual-contrasts in deep penetration. The system employs adaptive image processing, including automatic sample segmentation and dual speed of sound values determination and image reconstructing. The ultrasound image data assisted segmentation method is independent of mice size and physiological status, for example, respiration. After completing the segmentation, acoustic propagation can be modelled for image reconstruction. The adaptive dual-speed optimization, i.e., the determination of two optimized speed of sound values, avoids subjective uncertainty and is more efficient. In one example, about 14 minutes is used to determine the optimized speed of sound values and reconstruct the ultrasound and photoacoustic images based on the method of FIG. 34. In some instances, if the mice being imaged are fixed in the elevational position, the temperature of the coupling medium (water) reaches equilibrium, and the physiological status if the mice is stable, the ToF map can be calculated only once to achieve real-time display. With a suitable data processing system, and optionally efficiency improving algorithms such as the GSS method, the method in this example can achieve real-time image processing, reconstruction, and display. The system provides good imaging quality from various aspects, including (1) the ring-shaped transducer elements array offers a full 360 degrees view angle, (2) the system can acquire data at video rate (which mitigates motion artifacts), (3) the dual speed of sound values reconstruction reduces split or fringing artifacts, etc.

The method in FIG. 34 can be implemented automatically or semi-automatically, without or with less user input/intervention required.

The above disclosure has provided various examples and embodiments of the invention. Some embodiments provide a full-ring ultrasound and photoacoustic computed tomography system. In some examples the system may realize high-quality ultrasound and photoacoustic imaging with co-registered dual-contrasts in deep penetration. Some embodiments provide adaptive image reconstruction algorithms. The adaptive image reconstruction algorithms can include a single speed of sound value based image reconstruction. The adaptive image reconstruction algorithms can include a two speed of sound values based image reconstruction. The speed of sound values selection and/or determination in these adaptive image reconstruction algorithms may be automatically determined without manual operator intervention. The single speed of sound value based image reconstruction can achieve real-time images processing and display. The dual speed of sound values based image reconstruction method can provide a higher image quality and faster than existing iterative computation method. In some embodiments, the speed of sound values can be automatically determined based on the ultrasonic pulse-echo signals. In some embodiments, the dual speed of sound values based image reconstruction algorithm also includes a boundary segmentation operation. The boundary segmentation operation can be performed automatically without or with little user intervention and accurately.

Although not required, the embodiments described with reference to the Figures can be implemented as an application programming interface (API) or as a series of libraries for use by a developer or can be included within another software application, such as a terminal or computer operating system or a portable computing device operating system. Generally, as program modules include routines, programs, objects, components and data files assisting in the performance of particular functions, the skilled person will understand that the functionality of the software application may be distributed across a number of routines, objects and/or components to achieve the same functionality desired herein.

It will also be appreciated that where the methods and systems of the invention are either wholly implemented by computing system or partly implemented by computing systems then any appropriate computing system architecture may be utilized. This will include stand-alone computers, network computers, dedicated or non-dedicated hardware devices. Where the terms "computing system" and "computing device" are used, these terms are intended to include (but not limited to) any appropriate arrangement of computer or information processing hardware capable of implementing the function described.

It will be appreciated by persons skilled in the art that numerous variations and/or modifications may be made to the invention as shown in the specific embodiments to provide other embodiments of the invention. The described embodiments of the invention should therefore be considered in all respects as illustrative, not restrictive. One or more of the illustrated methods can be performed using at least partly one or more of the illustrated systems/devices. One or more of the illustrated methods can be performed using systems/devices not specifically illustrated. One or more of the illustrated systems/devices can at least partly implement one or more of the illustrated methods. One or more of the illustrated systems/devices may not implement one or more of the illustrated methods. Example optional features of various aspects of the invention are set forth in the summary section. Some embodiments of the invention may include one or more of the optional features. Some embodiments of the invention may lack one or more of the optional features. The data processing method embodiments can be applied to process complementary photoacoustic and ultrasound imaging data obtained from imaging systems not specifically described. The systems and methods of the invention can be used for imaging different objects such as but not limited to animal, human, phantom, sample, etc. In some embodiments, methods of the invention can be performed online in substantially real time In some embodiments, methods of the invention can be performed offline.

The invention claimed is:

1. A system for processing photoacoustic and ultrasound imaging data, comprising:
   one or more processors; and
   memory storing one or more programs configured to be executed by the one or more processors, the one or more programs including instructions for:
      obtaining ultrasound imaging data representative of an ultrasound image of an object, the ultrasound imaging data being obtained from a system for photoacoustic imaging and ultrasound imaging;
      performing a speed of sound value optimization operation based on the ultrasound imaging data for facilitating image reconstruction; and
      performing an image reconstruction operation;
   wherein the instructions for performing the speed of sound value optimization operation comprise instructions for:
      performing a segmentation operation on the ultrasound imaging data to obtain a plurality of subsets of ultrasound imaging data; and
      determining, for each respective one of the plurality of subsets of ultrasound imaging data, a respective optimal speed of sound value for use in the image reconstruction operation;
   wherein the instructions for performing a segmentation operation on the ultrasound imaging data comprise instructions for:
      processing the ultrasound imaging data to determine a boundary between two sections of the ultrasound image; and
      dividing the ultrasound imaging data into, at least, a first subset of ultrasound imaging data associated with one of the two sections and a second subset of ultrasound imaging data associated with another one of the two sections;
   wherein the instructions for determining respective optimal speed of sound value for each respective one of the plurality of subsets of ultrasound imaging data comprise instructions for:
      processing the first subset of ultrasound imaging data associated with the one of the two sections to determine a first optimal speed of sound value associated with the one of the two sections, the first optimal speed of sound value is arranged for use in the image reconstruction operation; and/or
      processing the second subset of ultrasound imaging data associated with another one of the two sections to determine a second optimal speed of sound value associated with another one of the two sections, the second optimal speed of sound value is arranged for use in the image reconstruction operation;
   wherein the instructions for processing the first subset of ultrasound imaging data associated with the one of the two sections to determine a first optimal speed of sound value associated with the one of the two sections comprise instructions for:
  processing the first subset of ultrasound imaging data respectively using each of a plurality of predetermined speed of sound values to determine a plurality of total coherence factor values, each respective one of the plurality of total coherence factor values being associated with the processing of the first subset of ultrasound imaging data using a respective one of the predetermined speed of sound values; and
  determining, based on the plurality of total coherence factor values, a speed of sound value that corresponds to the first optimal speed of sound value.

2. The system of claim 1, wherein the instructions for performing the speed of sound value optimization operation comprise instructions for processing the ultrasound imaging data to determine an optimal speed of sound value for use in the image reconstruction operation.

3. The system of claim 1, wherein the instructions for processing the ultrasound imaging data to determine a boundary between two sections of the ultrasound image comprise instructions for:
  determining a map based on ultrasound signals received by each respective transducer element of the system for photoacoustic imaging and ultrasound imaging as a result of ultrasound waves detected at the transducer element in response to transmission of ultrasound waves by the transducer element towards the object; and
  determining the boundary based on the map.

4. The system of claim 3, wherein the instructions for determining the boundary based on the map comprise instructions for:
  processing the map to determine first arrival positions of the ultrasound signals; and
  determining the boundary based on the determined first arrival positions.

5. The system of claim 1,
  wherein the two sections include the object and a coupling medium respectively, and
  wherein the instructions for determining respective optimal speed of sound value for each respective one of the plurality of subsets of ultrasound imaging data comprise instructions for:
  processing the first subset of ultrasound imaging data associated with the object to determine a first optimal speed of sound value associated with the object, the first optimal speed of sound value is arranged for use in the image reconstruction operation; and
  determining a second optimal speed of sound value associated with the coupling medium based on a temperature or an average temperature of the coupling medium at the time the ultrasound imaging data is acquired, the second optimal speed of sound value is arranged for use in the image reconstruction operation.

6. The system of claim 1, wherein the instructions for processing the first subset of ultrasound imaging data respectively using each of a plurality of predetermined speed of sound values comprise instructions for:
  processing the first subset of ultrasound imaging data respectively using each of a plurality of predetermined speed of sound values to determine to determine a plurality of time of flight maps, each respective one of the plurality of time of flight maps being associated with the processing of the first subset of ultrasound imaging data using a respective one of the predetermined speed of sound values;
  for each of the plurality of time of flight maps, processing the time of flight map to determine a respective ultrasound image; and
  for each of the plurality of determined ultrasound images, determining a total coherence factor value based on a sum of coherence factor values of the coherence factor map.

7. The system of claim 6, wherein the instructions for determining a speed of sound value based on the plurality of total coherence factor values comprise instructions for:
  determining a total coherence factor value function based on the plurality of total coherence factor values; and
  determining a speed of sound value corresponding to an extreme value of the total coherence factor value function, the determined speed of sound value corresponds to the first optimal speed of sound value.

8. The system of claim 7, wherein the instructions for determining a speed of sound value corresponding to an extreme value of the total coherence factor value function comprise instructions for determining a speed of sound value corresponding to an extreme value of the total coherence factor value function by processing only an extreme portion of the total coherence factor value function.

9. The system of claim 6, wherein the plurality of time of flight maps are determined based on multi-stencil fast marching method.

10. The system of claim 1, wherein the one or more programs further comprise instructions for:
  obtaining corresponding photoacoustic imaging data representative of a corresponding photoacoustic image of the object, the photoacoustic imaging data being obtained from the system for photoacoustic imaging and ultrasound imaging; and
  wherein the instructions for performing the image reconstruction operation comprise instructions for: processing the photoacoustic imaging data based on the determined first and second optimal speed of sound values to reconstruct a photoacoustic image of the object; and
  processing the ultrasound imaging data based on the determined first and second optimal speed of sound values to reconstruct an ultrasound image of the object.

11. The system of claim 1, wherein the system further comprises:
  a display operably connected with the one or more processors, the display is arranged to display the reconstructed ultrasound image and the reconstructed photoacoustic image.

12. A method for processing photoacoustic and ultrasound imaging data, comprising:
  obtaining ultrasound imaging data representative of an ultrasound image of an object, the ultrasound imaging data being obtained from a system for photoacoustic imaging and ultrasound imaging;
  performing a speed of sound value optimization operation based on the ultrasound imaging data for facilitating image reconstruction; and
  performing an image reconstruction operation,
    wherein performing the speed of sound value optimization operation comprises:
      performing a segmentation operation on the ultrasound imaging data to obtain a plurality of subsets of ultrasound imaging data; and determining, for each respective one of the plurality of subsets of ultrasound imaging data, a respective optimal speed of sound value for use in the image reconstruction operation;

wherein performing a segmentation operation on the ultrasound imaging data comprises:

processing the ultrasound imaging data to determine a boundary between two sections of the ultrasound image; and dividing the ultrasound imaging data into, at least, a first subset of ultrasound imaging data associated with one of the two sections and a second subset of ultrasound imaging data associated with another one of the two sections;

wherein determining respective optimal speed of sound value for each respective one of the plurality of subsets of ultrasound imaging data comprises:

processing the first subset of ultrasound imaging data associated with the one of the two sections to determine a first optimal speed of sound value associated with the one of the two sections, the first optimal speed of sound value is arranged for use in the image reconstruction operation; and/or processing the second subset of ultrasound imaging data associated with another one of the two sections to determine a second optimal speed of sound value associated with another one of the two sections, the second optimal speed of sound value is arranged for use in the image reconstruction operation;

wherein processing the first subset of ultrasound imaging data associated with the one of the two sections to determine a first optimal speed of sound value associated with the one of the two sections comprises:

processing the first subset of ultrasound imaging data respectively using each of a plurality of predetermined speed of sound values to determine a plurality of total coherence factor values, each respective one of the plurality of total coherence factor values being associated with the processing of the first subset of ultrasound imaging data using a respective one of the predetermined speed of sound values; and determining, based on the plurality of total coherence factor values, a speed of sound value that corresponds to the first optimal speed of sound value.

13. A system for photoacoustic imaging and ultrasound imaging, comprising:

a laser module operable to irradiate an object with laser radiation;

a transducer unit comprising a plurality of transducer elements operable to detect ultrasound waves generated by the object in response to the laser module irradiating the object with the laser radiation, and generate electric signals that form photoacoustic imaging data based on the detected ultrasound waves; and transmit ultrasound waves towards the object and, in response, detect ultrasound waves reflected, scattered, and/or transmitted by the object, for facilitating ultrasound imaging, and generate electric signals that form ultrasound imaging data based on the detected ultrasound waves;

a control unit operably coupled with the irradiation unit and the transducer unit and for controlling operation of the transducer unit; and a system of claim 1 arranged to process the photoacoustic imaging data and the ultrasound imaging data.

\* \* \* \* \*